US012595239B2

(12) United States Patent
Huwyler et al.

(10) Patent No.: US 12,595,239 B2
(45) Date of Patent: Apr. 7, 2026

(54) SUBSTITUTED ISOXAZOLINE DERIVATIVES

(71) Applicant: BASF SE, Ludwigshafen (DE)

(72) Inventors: Nikolas Huwyler, Ludwigshafen (DE); Karsten Koerber, Ludwigshafen (DE); Erik Gilberg, Ludwigshafen (DE); Sunderraman Sambasivan, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 427 days.

(21) Appl. No.: 18/276,304

(22) PCT Filed: Jan. 31, 2022

(86) PCT No.: PCT/EP2022/052181

§ 371 (c)(1),
(2) Date: Aug. 8, 2023

(87) PCT Pub. No.: WO2022/171472

PCT Pub. Date: Aug. 18, 2022

(65) Prior Publication Data

US 2024/0140917 A1 May 2, 2024

(30) Foreign Application Priority Data

Feb. 11, 2021 (EP) .................................... 21156573
Feb. 11, 2021 (EP) .................................... 21156575

(51) Int. Cl.
*C07D 261/14* (2006.01)
*A01P 7/04* (2006.01)
*C07D 413/12* (2006.01)

(52) U.S. Cl.
CPC .............. *C07D 261/14* (2013.01); *A01P 7/04* (2021.08); *C07D 413/12* (2013.01)

(58) Field of Classification Search
CPC ........ C07D 261/14; C07D 413/12; A01P 7/04
See application file for complete search history.

(56) References Cited

U.S. PATENT DOCUMENTS 4,397,853 A 8/1983 Kawakita et al.

FOREIGN PATENT DOCUMENTS

| | | | |
|---|---|---|---|
| CN | 110483491 | A | 11/2019 |
| JP | S5677267 | A | 6/1981 |
| TW | 201528952 | A | 8/2015 |
| WO | WO-2004/022536 | A1 | 3/2004 |
| WO | WO-2010/020522 | A1 | 2/2010 |
| WO | WO-2010/135360 | A1 | 11/2010 |
| WO | WO-2011/067272 | A1 | 6/2011 |
| WO | WO-2012/007426 | A1 | 1/2012 |
| WO | WO-2013/032804 | A1 | 3/2013 |
| WO | WO-2015/066277 | A1 | 5/2015 |
| WO | 2018197466 | * | 11/2018 |
| WO | WO-2018/197466 | A1 | 11/2018 |
| WO | WO-2020/064560 | A1 | 4/2020 |
| WO | 2020164938 | * | 8/2020 |
| WO | WO-2020/164938 | A1 | 8/2020 |

OTHER PUBLICATIONS

International Application No. PCT/EP2022/052181, International Search Report and Written Opinion, mailed Mar. 9, 2022.
European Patent Application No. 21156573.4, Extended European Search Report, dated May 11, 2021.

* cited by examiner

*Primary Examiner* — D Margaret M Seaman
(74) *Attorney, Agent, or Firm* — MARSHALL, GERSTEIN & BORUN LLP

(57) ABSTRACT

The invention relates to isoxazoline compounds of formula (I) wherein the variables have the meanings as defined in the specification, to compositions comprising them, to active compound combinations comprising them, and to their use for protecting growing plants and animals from attack or infestation by invertebrate pests, furthermore, to seed comprising such compounds.

(I)

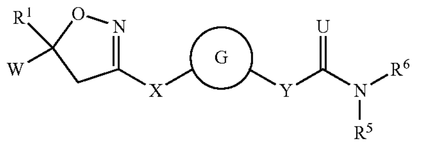

17 Claims, No Drawings

SUBSTITUTED ISOXAZOLINE DERIVATIVES

CROSS-REFERENCE TO RELATED APPLICATIONS

This is the U.S. national phase of International Application No. PCT/EP2022/052181, filed Jan. 31, 2022, which claims the benefit of European Patent Application No. 21156573.4, filed Feb. 11, 2021, and European Patent Application No. 21156575.9, filed Feb. 11, 2021.

The invention relates to isoxazoline compounds of formula I

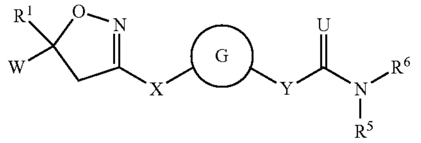

I wherein $R^1$ is $C_1$-$C_2$-haloalkyl;

W is phenyl, or 5- or 6-membered heteroaryl comprising as ring members 1, 2, or 3 heteroatoms selected from N, O, and S; wherein W is unsubstituted, partially or fully substituted with $R^2$;

$R^2$ is halogen, $OR^{21}$, $NR^{22}R^{23}$, CN, $NO_2$, $Si(CH_3)_3$, $SbF_5$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_3$-alkoxy, $C_1$-$C_3$-haloalkoxy, $C_1$-$C_3$-alkyl-$S(O)_m$, $C_1$-$C_3$-haloalkyl-$S(O)_m$, $C_1$-$C_3$-alkoxy-$C_1$-$C_4$-alkyl, $C_1$-$C_3$-haloalkoxy-$C_1$-$C_4$-alkyl, $C_1$-$C_3$-alkyl-$S(O)_m$—$C_1$-$C_4$-alkyl, $C_1$-$C_3$-haloalkyl-$S(O)_m C_1$-$C_4$-alkyl, $C_3$-$C_6$-cycloalkyl, $C_3$-$C_6$-halocycloalkyl; which groups are optionally substituted with $R^{211}$;

m is 0, 1, or 2;

$R^{21}$ H, $C_1$-$C_6$-alkyl, $C_2$-$C_6$-alkenyl, $C_2$-$C_6$-alkynyl, $C_3$-$C_8$-cycloalkyl, $C_1$-$C_4$-alkyl-$S(O)_m$, $Si(C_1$-$C_4$-alkyl$)_3$, which groups are unsubstituted, partially or fully substituted with $R^{211}$;

$R^{211}$ halogen, $C_1$-$C_4$-alkoxy, $C_1$-$C_4$-haloalkoxy, $C_3$-$C_4$-alkenyloxy, $C_3$-$C_4$-haloalkenyloxy, $C_3$-$C_4$-alkynyloxy, $C_3$-$C_4$-haloalkynyloxy, $C_1$-$C_4$-alkyl-$S(O)_m$, $C_1$-$C_4$-haloalkyl-$S(O)_m$, $C_3$-$C_4$-alkenyl-$S(O)_m$, $C_3$-$C_4$-haloalkenyl-$S(O)_m$, $C_3$-$C_4$-alkynyl-$S(O)_m$, $C_3$-$C_4$-haloalkynyl-$S(O)_m$, and oxo; $C_3$-$C_8$-cycloalkyl, $C_3$-$C_8$-halocycloalkyl, $C_3$-$C_8$-cycloalkenyl, $C_3$-$C_8$-halocycloalkenyl;

$R^{22}$, $R^{23}$ H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, which are unsubstituted or partially or fully substituted with $R^{221}$; or $C_1$-$C_6$-alkyl-C(═O)$OR^{13}$, $C_1$-$C_6$-alkyl-C(═U)N$(R^{12a})R^{12b}$, $C_1$-$C_6$-alkyl-C(═$NR^{12}$)N$(R^{12a})R^{12b}$, $S(O)_mR^{13}$, $S(O)_mN(R^{12a})R^{12b}$, C(═U)$R^{11}$, C(═O)$OR^{13}$, C(═U)N$(R^{12a})R^{12b}$, C(═S)$SR^{13}$, C(═$NR^{12}$)$R^{11}$;

$C_3$-$C_8$-cycloalkyl, $C_3$-$C_8$-halocycloalkyl;

$R^{221}$ CN, $NO_2$, OH, SH, SCN, $SF_5$, $Si(C_1$-$C_4$-alkyl$)_3$, $C_1$-$C_6$-alkoxy, $C_1$-$C_6$-haloalkoxy, $C_1$-$C_6$-alkyl-$S(O)_m$, $C_1$-$C_6$-haloalkyl-$S(O)_m$, C(═O)N$(R^{12a})R^{12b}$; $C_3$-$C_8$-cycloalkyl which is unsubstituted, partially or fully halogenated and/or partially or fully substituted with $C_1$-$C_4$-alkyl, $C_3$-$C_4$-cycloalkyl, $C_1$-$C_4$-alkoxy, $C_1$-$C_4$-haloalkoxy, and oxo; or two $R^{221}$ present on the same carbon atom of an alkyl, alkenyl, alkynyl or cycloalkyl group may together be ═O, ═CH($C_1$-$C_4$-alkyl), ═C($C_1$-$C_4$-alkyl$)_2$, ═N($C_1$-$C_6$-alkyl), or ═NO($C_1$-$C_6$-alkyl); or $R^{22}$ and $R^{23}$ form together with the nitrogen atom they are bonded to a 3-, 4-, 5-, or 6-membered fully unsaturated heterocycle, which heterocycle may additionally contain one heteroatom selected from N, O, and $S(O)_m$ as ring members, and which heterocycle is unsubstituted or partially or fully substituted with $R^{14}$; or $R^{22}$ and $R^{23}$ together form a group ═C$(R^{11})_2$, ═$S(O)_m(R^{13})_2$, ═$S(O)_mR^{13}N(R^{12a})R^{12b}$;

X is $NR^3$, O, $S(O)_m$, or $CH_2$;

$R^3$ is $OR^{21}$, or a group as defined for $R^5$;

G is phenyl, or 5- or 6-membered heteroaryl comprising as ring members 1, 2, or 3 heteroatoms selected from N, O and S; wherein G is unsubstituted, partially, or fully substituted with $R^4$;

$R^4$ is a group as defined for $R^2$;

U is O or S;

$R^5$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylthio, $C_1$-$C_6$-haloalkylthio, which are unsubstituted or partially or fully substituted with $R^{51}$; or $C_1$-$C_6$-alkyl-C(═O)$OR^{13}$, $C_1$-$C_6$-alkyl-C(═U)N$(R^{12a})R^{12b}$, $C_1$-$C_6$-alkyl-C(═$NR^{12}$)N$(R^{12a})R^{12b}$, N$(R^{12a})R^{12b}$, $S(O)_mR^{13}$, $S(O)_mN(R^{12a})R^{12b}$, C(═U)$R^{11}$, C(═O)$OR^{13}$, C(═U)N$(R^{12a})R^{12b}$ C(═S)$SR^{13}$, C(═$NR^{12}$)$R^{11}$;

$C_3$-$C_8$-cycloalkyl, $C_3$-$C_8$-halocycloalkyl, phenyl, a 3-, 4-, 5-, 6- or 7-membered saturated or partially unsaturated heterocycle comprising 1, 2, 3 or 4 heteroatoms selected from N, O, and $S(O)_m$ as ring members, or a 5- or 6-membered hetaryl comprising 1, 2, 3 or 4 heteroatoms selected from N, O, and $S(O)_m$ as ring members, which rings are unsubstituted or partially or fully substituted with $R^{52}$;

$R^{51}$ halogen, CN, $NO_2$, OH, SH, SCN, $SF_5$, $Si(C_1$-$C_4$-alkyl$)_3$, N$(R^{12a})R^{12b}$, $C_1$-$C_6$-alkoxy, $C_1$-$C_6$-haloalkoxy, $C_1$-$C_6$-alkyl-$S(O)_m$, $C_1$-$C_6$-haloalkyl-$S(O)_m$, C(═O)N$(R^{12a})R^{12b}$; $C_3$-$C_8$-cycloalkyl which is unsubstituted, partially or fully halogenated and/or partially or fully substituted with CN, $C_1$-$C_4$-alkyl, $C_3$-$C_4$-cycloalkyl, $C_1$-$C_4$-alkoxy, $C_1$-$C_4$-haloalkoxy, and oxo;

N$(R^{12a})R^{12b}$, $S(O)_mR^{13}$, $S(O)_mN(R^{12a})R^{12b}$, C(═U)$R^{11}$, C(═O)$OR^{13}$, C(═U)N$(R^{12a})R^{12b}$ C(═S)$SR^{13}$, C(═$NR^{12}$)$R^{11}$;

phenyl, benzyl, phenoxy, or 3-, 4-, 5-, 6- or 7-membered saturated, partially or fully unsaturated heterocycle containing 1, 2, or 3 heteroatoms selected from N, O, $S(O)_m$ as ring members, wherein the rings are unsubstituted or partially or fully substituted with $R^{14}$; or two $R^{51}$ present on the same carbon atom of an alkyl, alkenyl, alkynyl or cycloalkyl group may together be ═O, ═CH($C_1$-$C_4$-alkyl), ═C($C_1$-$C_4$-alkyl$)_2$, ═N($C_1$-$C_6$-alkyl), or ═NO($C_1$-$C_6$-alkyl);

$R^{52}$ is a group as defined in $R^{51}$ or selected from $C_1$-$C_6$-alkyl, $C_2$-$C_6$-alkenyl, and $C_2$-$C_6$-alkynyl, which groups are unsubstituted, partially or fully halogenated and/or substituted with one or two CN, $C_3$-$C_4$-cycloalkyl, $C_1$-$C_4$-alkoxy, $C_1$-$C_4$-haloalkoxy, or oxo;

$R^6$ is a group as defined for $R^5$; or $R^5$ and $R^6$ form together with the nitrogen atom they are bonded to a 3-, 4-, 5-, 6-, 7- or 8-membered saturated, partially or fully unsaturated heterocycle which heterocycle may additionally contain one or two heteroatoms selected from N, O, and $S(O)_m$ as ring members, and which heterocycle is unsubstituted or partially or fully substituted with $R^{14}$; or $R^5$ and $R^6$ together form a group $=C(R^{11})_2$, $=S(O)_m(R^{13})_2$, $=S(O)_mN(R^{12a})R^{12b}$, $=NR^{12}$, or $=NOR^{13}$; or $R^5$ and $R^6$ together with the nitrogen they are bound to form a mesoionic entity;

Y having at G one or two ring atoms of G between connection points of G to X and Y; Y being a direct bond or $CR^7R^8$;

$R^7$, $R^8$ are each independently selected from H, halogen, CN, $C_1$-$C_6$-alkyl, $C_3$-$C_8$-cycloalkyl, $C_2$-$C_6$-alkenyl, and $C_2$-$C_6$-alkynyl, which groups may be partially or fully halogenated and/or may be substituted by one or more $R^{81}$;

$R^{81}$ is CN, $N_3$, $NO_2$, SCN, $SF_5$, $C_3$-$C_8$-cycloalkyl, $C_3$-$C_8$-halocycloalkyl; $Si(C_1$-$C_4$-alkyl$)_3$, $OR^{13}$, $OSO_2R^{13}$, $S(O)_mR^{13}$, $NR^{22}R^{23}$, $C(=O)NR^{22}R^{23}$; or $R^7$ and $R^8$, together with the carbon atom they are bonded to, form a 3-, 4-, 5-, 6-, 7- or 8-membered saturated or partially unsaturated carbocycle or heterocycle, wherein the heterocycle comprises 1, 2, 3 or 4 heteroatoms or heteroatom groups independently selected from N, O, and $S(O)_m$ as ring members, which rings are unsubstituted or substituted with 1 or 2 groups $R^{14}$;

$R^{11}$ is CN, $NO_2$, OH, SH, SCN, $SF_5$, $C_1$-$C_6$-alkoxy, $C_1$-$C_6$-haloalkoxy, $C_1$-$C_6$-alkyl-$S(O)_m$, $C_1$-$C_6$-haloalkyl-$S(O)_m$, $Si(C_1$-$C_4$-alkyl$)_3$, $C(=O)N(R^{12a})R^{12b}$, $C_3$-$C_8$-cycloalkyl which is unsubstituted or partially or fully halogenated and/or substituted with 1 or 2 $C_1$-$C_4$-alkyl, $C_3$-$C_4$-cycloalkyl, $C_1$-$C_4$-alkoxy, $C_1$-$C_4$-haloalkoxy, and oxo; phenyl, benzyl, phenoxy, a 3-, 4-, 5-, 6- or 7-membered saturated, partially or fully unsaturated heterocycle containing 1, 2 or 3 heteroatoms N, O, and $S(O)_m$ as ring members, which rings are unsubstituted or partially or fully halogenated and/or substituted with $R^{14}$; or two $R^{11}$ present on the same carbon atom of an alkyl, alkenyl, alkynyl or cycloalkyl may together form $=O$, $=CH(C_1$-$C_4$-alkyl$)$, $=C(C_1$-$C_4$-alkyl$)C_1$-$C_4$-alkyl, $=N(C_1$-$C_6$-alkyl$)$, or $=NO(C_1$-$C_6$-alkyl$)$; and $R^{11}$ bonded to a cycloalkyl ring is additionally $C_1$-$C_6$-alkyl, $C_2$-$C_6$-alkenyl, and $C_2$-$C_6$-alkynyl, which are unsubstituted, partially or fully halogenated and/or substituted with 1 or 2 groups CN, $C_3$-$C_4$-cycloalkyl, $C_1$-$C_4$-alkoxy, $C_1$-$C_4$-haloalkoxy, and oxo; and $R^{11}$ in groups $=C(R^{11})_2$, $N=C(R^{11})_2$, $C(=U)R^{11}$, and $C(=NR^{12})R^{11}$ is additionally selected from H, halogen, $C_1$-$C_6$-alkyl, $C_2$-$C_6$-alkenyl, and $C_2$-$C_6$-alkynyl, which are unsubstituted, partially or fully halogenated and/or substituted with 1 or 2 groups CN, $C_3$-$C_4$-cycloalkyl, $C_1$-$C_4$-alkoxy, $C_1$-$C_4$-haloalkoxy, and oxo;

$R^{12}$ is H, $C_1$-$C_6$-alkoxy, $C_1$-$C_6$-haloalkoxy, $S(O)_m$—$C_1$-$C_4$-alkyl, $S(O)_m$—$C_1$-$C_4$-haloalkyl, $Si(C_1$-$C_4$-alkyl$)_3$, $C_1$-$C_6$-alkyl, $C_3$-$C_6$-alkenyl, $C_3$-$C_6$-alkynyl, which are unsubstituted or partially or fully halogenated and/or substituted with CN, $C_1$-$C_4$-alkoxy, $C_1$-$C_4$-haloalkoxy, $S(O)_m$—$C_1$-$C_4$-alkyl, $S(O)_m$—$C_1$-$C_4$-haloalkyl, $C_3$-$C_6$-cycloalkyl which is unsubstituted or substituted with 1 or 2 halogen and/or CN; and oxo;

$C_3$-$C_8$-cycloalkyl which is unsubstituted or partially or fully halogenated and/or substituted with CN, $C_1$-$C_4$-alkyl, $C_1$-$C_4$-alkoxy, $C_1$-$C_4$-haloalkoxy, $S(O)_m$—$C_1$-$C_4$-alkyl, $C_3$-$C_4$-cycloalkyl, $C_3$-$C_4$-cycloalkyl-$C_1$-$C_4$-alkyl which rings may be substituted with 1 or 2 halogen and/or CN; and oxo;

phenyl, benzyl, pyridyl, phenoxy, which are unsubstituted or partially or fully halogenated and/or substituted with halogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, and $(C_1$-$C_6$-alkoxy)carbonyl; and a 3-, 4-, 5- or 6-membered saturated, partially or fully unsaturated heterocycle comprising 1, 2 or 3 heteroatoms selected from N, O, and $S(O)_m$ as ring members, where the heterocycle is optionally substituted with one or more $R^{14}$;

$R^{12a}$ and $R^{12b}$ have the meanings given for $R^{12}$; or $R^{12a}$ and $R^{12b}$, together with the nitrogen atom to which they are bound, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from N, O, and $S(O)_m$ as ring members, which heterocycle is unsubstituted or substituted with one or more substituents halogen, $C_1$-$C_4$-alkyl, $C_1$-$C_4$-haloalkyl, $C_1$-$C_4$-alkoxy, $C_1$-$C_4$-haloalkoxy, and oxo; or $R^{12a}$ and $R^{12}$, together with the nitrogen atoms to which they are bound in the group $C(=NR^{12})N(R^{12a})R^{12b}$, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from N, O, and $S(O)_m$ as ring members, which heterocycle is unsubstituted or substituted with one or more substituents halogen, $C_1$-$C_4$-alkyl, $C_1$-$C_4$-haloalkyl, $C_1$-$C_4$-alkoxy, $C_1$-$C_4$-haloalkoxy, and oxo;

$R^{13}$ is H, $Si(C_1$-$C_4$-alkyl$)_3$, $C_1$-$C_6$-alkyl, $C_2$-$C_6$-alkenyl, $C_2$-$C_6$-alkynyl, which are unsubstituted or partially or fully halogenated and/or substituted with $C_3$-$C_4$-cycloalkyl, $C_1$-$C_4$-alkoxy, $C_1$-$C_4$-haloalkoxy, $S(O)_m$—$C_1$-$C_4$-alkyl, and oxo;

$C_3$-$C_8$-cycloalkyl which is unsubstituted or partially or fully halogenated and/or substituted with $C_1$-$C_4$-alkyl, $C_3$-$C_4$-cycloalkyl, $C_1$-$C_4$-alkoxy, $C_1$-$C_4$-haloalkoxy, $S(O)_m$—$C_1$-$C_4$-alkyl, and oxo;

phenyl, benzyl, pyridyl and phenoxy, which are unsubstituted or partially or fully halogenated and/or substituted with $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, and $(C_1$-$C_6$-alkoxy)carbonyl;

$R^{14}$ is halogen, $NO_2$, CN, OH, SH, $C_1$-$C_6$-alkoxy, $C_1$-$C_6$-haloalkoxy, $S(O)_m$—$C_1$-$C_4$-alkyl, $S(O)_mC_1$-$C_4$-haloalkyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C(=O)NR^{12a}R^{12b}$, $Si(C_1$-$C_4$-alkyl$)_3$;

$C_1$-$C_4$-alkyl, $C_2$-$C_6$-alkenyl, $C_2$-$C_6$-alkynyl, which are unsubstituted or partially or fully halogenated and/or substituted with $C_3$-$C_4$-cycloalkyl, $C_1$-$C_4$-alkoxy, $C_1$-$C_4$-haloalkoxy, $S(O)_mC_1$-$C_4$-alkyl, and oxo;

$C_3$-$C_8$-cycloalkyl which is unsubstituted or partially or fully halogenated and/or substituted with $C_1$-$C_4$-alkyl, $C_3$-$C_4$-cycloalkyl, $C_1$-$C_4$-alkoxy, $C_1$-$C_4$-haloalkoxy, $S(O)_m$—$C_1$-$C_4$-alkyl, and oxo;

phenyl, benzyl, pyridyl and phenoxy, which are unsubstituted or partially or fully halogenated and/or substituted with $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, and ($C_1$-$C_6$-alkoxy)carbonyl; or two $R^{14}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl; or two $R^{14}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, and $S(O)_m$ as ring members, and wherein the ring is optionally substituted with one or more groups $C_1$-$C_4$-alkyl, $C_1$-$C_4$-haloalkyl, $C_1$-$C_4$-alkoxy, and/or $C_1$-$C_4$-haloalkoxy;

m is independently 0, 1 or 2; and the N-oxides, stereoisomers and agriculturally or veterinarily acceptable salts thereof.

The invention also provides an agricultural composition comprising at least one compound of formula I, a stereoisomer thereof and/or an agriculturally acceptable salt thereof and at least one liquid and/or solid carrier, especially at least one inert liquid and/or solid agriculturally acceptable carrier.

The invention also provides a veterinary composition comprising at least one compound of formula I, a stereoisomer thereof and/or a veterinarily acceptable salt thereof and at least one liquid and/or solid carrier, especially at least one inert veterinarily liquid and/or solid acceptable carrier.

The invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof as defined herein.

The present invention also relates to plant propagation material, in particular seed, comprising at least one compound of formula I and/or an agriculturally acceptable salt thereof.

The invention further relates to a method for treating or protecting an animal from infestation or infection by parasites which comprises bringing the animal in contact with a parasiticidally effective amount of a compound of formula I or a veterinarily acceptable salt thereof. Bringing the animal in contact with the compound I, its salt or the veterinary composition of the invention means applying or administering it to the animal.

WO 2010/020522 and WO 2010/135360 describe structurally closely related active compounds. These compounds are mentioned to be useful for combating invertebrate pests.

Nevertheless, there remains a need for highly effective and versatile agents for combating invertebrate pests. It is therefore an object of the present invention to provide compounds having a good pesticidal activity and showing a broad activity spectrum against a large number of different invertebrate pests, especially against difficult to control pests, such as insects.

It has been found that these objects can be achieved by compounds of formula I as depicted and defined below, and by their stereoisomers, salts, tautomers and N-oxides, in particular their agriculturally acceptable salts.

Compounds of formula I wherein U is O (formula I.O) can be prepared by reacting an activated carboxylic acid derivative of formula II or the corresponding carboxylic acid IIa with a compound of formula III in an amidation reaction. R in formula II denotes a leaving group, preferably halogen such as e.g. Cl or Br, or $C_1$-$C_6$-alkoxy such as $OCH_3$ or $OC_2H_5$. Amine III is preferably used as its ammonium salt $^+HNR^5R^6$ $A^-$, wherein A is an anion, preferably a halogenide such as Cl or Br.

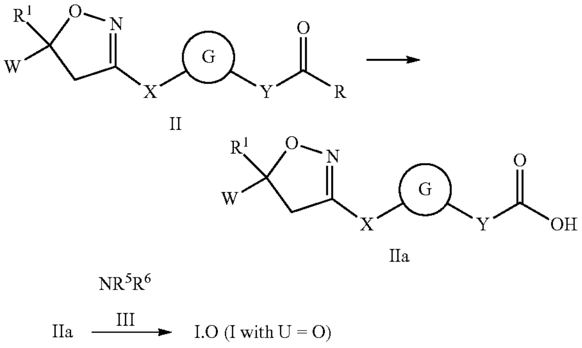

The saponification is carried out under conditions generally known in the art, e.g. dissolving the compound II in either tetrahydrofuran (THF), methanol or water or a mixture of the solvents, and adding alkali metal hydroxides, such as LiOH, NaOH, and KOH either as solid or in solution to the mixture. The reaction may proceed at room temperature (20-25° C.) or at elevated temperatures. Workup in a customary manner by aqueous extraction typically yields the compound IIa [cf. WO 2013/032804].

The amidation of compounds II is usually carried out with the acid chlorides or by prior transformation of carboxylic acids of formula IIa with oxalyl chloride [$(COCl)_2$] or thionylchloride ($SOCl_2$) to the corresponding acid chlorides, followed by reaction with the amine of formula III. Suitable reaction conditions are described in literature, e.g. in WO 2004/22536. The reaction is generally carried out in the presence of an organic base such as triethylamine ($Et_3N$), N,N-diisopropylethylamine ($iPr_2NEt$), pyridine, substituted pyridines such as collidine or lutidine, or the like. Optionally a nucleophilic catalyst such as 4-(N,N-dimethylamino)pyridine (DMAP) can be employed in the reaction. Suitable solvents are halogenated hydrocarbons such as, dichloromethane, chloroform, and chlorobenzene, or polar aprotic solvents such as THF, and N,N-dimethylformamide (DMF), or aromatic hydrocarbons such as benzene, toluene, o-, m-, and p-xylene, or mixtures thereof. The transformation is usually carried out at temperatures from −40° C. to 120° C., preferably from 0° C. to 40° C. The starting materials are generally reacted with one another in equimolar amounts. In terms of yield, it may be advantageous to employ an excess of III, based on II.

Alternatively, amidation of a carboxylic acid IIa is carried out in the presence of a coupling reagent. Suitable coupling reagents (activators) are known and are, e.g. selected from carbodiimides, such as N,N-dicyclohexylcarbodiimide (DCC) and N,N-diisopropylcarbodiimide (DCI), benzotriazole derivatives such as 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluorophosphate (HBTU), and 1-[bis(dimethylamino)methylen]-5-chlorobenzotriazolium 3-oxide hex-afluorophosphate (HCTU), or phosphonium-derived activators, such as 2,4,6-Tripropyl-1,3,5,2λ5,4λ5,6λ5-trioxatriphosphinane 2,4,6-trioxide (T3P), (Benzotriazol-1-yl-oxy)tris(dimethylamino)phosphonium hexafluorophosphate (BOP), (benzotriazol-1-yl-oxytripyrrolidinophosphonium hexafluorophosphate) (Py-BOP), bromotripyrrolidinophosphonium hexafluorophosphate (Py-BrOP). Generally, the activator is used in excess. The benzotriazole and phosphonium coupling reagents are generally used in a basic medium. Preferably, 2,4,6-tripropyl-1,3,5,2λ5,4λ5,6λ5-trioxatriphosphinane 2,4,6-trioxide (T3P) is used as the coupling reagent (activator). Suitable reaction conditions are described in the literature, e.g. in WO2015/128358. The reaction is generally carried out in the presence of a base such as a tertiary amine base like $iPr_2NEt$, $Et_3N$. Suitable solvents are e.g. halogenated hydrocarbons such as dichloromethane, chloroform, and chlorobenzene. The transformation is usually carried out at temperatures from 0° C. to 160° C., preferably from 25° C. to 100° C. The starting materials are generally reacted with one another in equimolar amounts. In terms of yield, it may be advantageous to employ an excess of Ill, based on II. Amines of formula III are commercially available or can be obtained by methods known in the art (e.g. WO 2016/168056, WO 2016/168058, WO 2016/168059, WO 2018/071327, WO 2019/194982, WO 2011/067272, WO 2005/085216).

Compounds II with X being $NR^3$ (formula II.1) can be prepared by reaction of an isoxazole amine of formula IIIA with a halogenide of formula IV, wherein $X^H$ is a halogen, preferably a bromide or iodide, in a Buchwald-Hartwig reaction (e.g. WO 2017/069980).

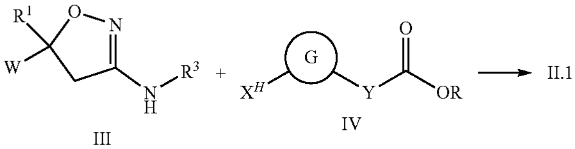

III IV II.1

This transformation is usually carried out at temperatures of from 20° C. to 180° C., preferably from 60° C. to 100° C., in an inert solvent, in the presence of a base and a palladium catalyst such as, e.g., tris(dibenzylideneacetone)dipalladium (0) $[Pd_2(dba)_3]$, 9,9-dimethyl-4,5-bis(diphenylphosphino) xanthene (XantPhos), or [2-(di-tert-butylphosphino)-2',4',6'-triisopropyl-1,1'-biphenyl][2-(2-aminoethyl)-phenyl)] palladium(II) chlorid (tBuXPhos Pd G1) [cf. WO 2017/069980].

Suitable solvents are ethers such as dioxane and THF, and the like, or alcohols such as butanol and tert-amyl alcohol, and the like, or polar aprotic solvents such as DMF, dimethylacetamide (DMA), N-methyl-2-pyrrolidon (NMP), and dimethyl sulfoxide (DMSO), and the like.

Preferably, 1,4-dioxane is employed. It is also possible to use mixtures of the solvents mentioned.

Suitable bases are, in general, inorganic compounds, such as alkali metal and alkaline earth metal carbonates, such as $Li_2CO_3$, $K_2CO_3$, $CaCO_3$, and $CSCO_3$, or organic compounds, such as alkali metal alcoholates, such as lithium tert-butylate, sodium tert-butylate, and potassium tert-butylate, and the like. Particular preference is given to $CSCO_3$. The bases are generally employed in equimolar amounts; however, they can also be used in in excess.

The starting materials are generally reacted with one another in equimolar amounts. In terms of yield, it may be advantageous to employ an excess of Ill, based on IV.

The compounds IV are commercially available or known from the literature [cf. e.g. US2011/0251247; THL 1997, 38, 1559] or can be prepared in accordance with the literature cited.

Compounds IIIA, wherein $R^3$ is H, can be prepared by oxo-Michael addition of hydroxyl amine, hydroxyurea, or a salt of either one of them (collectively compounds VA), to an acrylonitrile of formula V.

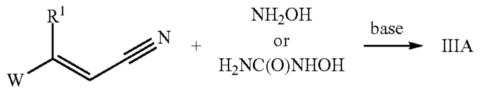

VA IIIA

The reaction of an acrylonitrile of formula V with a compound VA is usually carried out at temperatures of from −30° C. to 120° C., preferably from 25° C. to 80° C., in an inert solvent, in the presence of a base.

Suitable solvents are alcohols such as methanol, ethanol, n-propanol, isopropanol, n-butanol, tert-butanol, and the like, or halogenated hydrocarbons such as methylene chloride, chloroform, chlorobenzene, and the like, or aromatic hydrocarbons such as toluene, o-, m-, p-xylene, and the like, or ethers such as diethyl ether, methyl tert-butyl ether (MTBE), dioxane, anisole, and THF, or nitriles such as acetonitrile, and propionitrile. Moreover, DMSO, DMF, DMA, and water.

Preferably, alcohols such as methanol are used, and it is also possible to use mixtures of the solvents mentioned.

Suitable bases are, in general, inorganic compounds, such as alkali metal and alkaline earth metal hydroxides, such as LiOH, NaOH, KOH, $Ca(OH)_2$, and the like, or alkali metal and alkaline earth metal carbonates, such as $Li_2CO_3$, $K_2CO_3$, and $CaCO_3$, and the like, or alkali metal and alkaline earth metal hydrides, such as LiH, NaH, KH, $CaH_2$, and the like. Moreover, organic bases, e.g. alkali metal alcoholates, such as sodium methoxide, sodium ethoxide, lithium tert-butoxide, sodium tert-butoxide, potassium tert-butoxide, and the like, or alkali metal amide bases, such as lithium bis(trimethylsilyl)amide, sodium bis(trimethylsilyl) amide, potassium bis(trimethylsilyl)amide, and the like. Particular preference is given to alkali metal alcoholates such as sodium methoxide. The bases are generally employed in equimolar amounts; however, they can also be used in excess or, if appropriate, as solvent.

The starting materials are generally reacted with one another in equimolar amounts. In terms of yield, it may be advantageous to employ an excess of VA, based on V.

Furthermore, in certain cases it may be advantageous to employ a phase transfer catalyst in the reaction, e.g. a quaternary ammonium salt such as tetra-n-butylammonium bromide, tetra-n-butylammonium iodide, cetyl trimethylammonium chloride, cetyl trimethylammonium bromide, and the like. And, if desired, chiral phase transfer catalysts [cf. Org. Process Res. Dev. 2015, 19, 1731-1746; and references therein] can be employed in the reaction, such as cinchona derived quaternary ammonium salts like (R)-[(1S,2S,4S,5R)-1-(acridin-9-ylmethyl)-5-vinylquinuclidin-1-ium-2-yl]-

(6-methoxy-4-quinolyl)methanol bromide (CAS-No. 466639-23-6; e.g. US 2014/0350261) for the synthesis of enantiomerically enriched compounds III.

Compounds V can be prepared by Horner-Wadsworth-Emmons reaction of a ketone of formula VI with a compound VII.

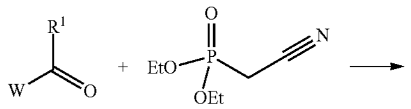

V

VI VII

This transformation is usually carried out at temperatures of from 0° C. to 120° C., preferably from 25° C. to 80° C., in an inert solvent, in the presence of a base [cf. J. Org. Chem. 1985, 50, 15, 2624, and references therein].

Suitable solvents are ethers such as THF, diethyl ether, MTBE, dimethoxy ethane (DME), dioxane and the like, or nitriles such as acetonitrile, propionitrile, and the like, or aromatic hydrocarbons such as benzene, toluene, o-, m-, p-xylene, and the like. Preferably, THF is employed, and it is also possible to use mixtures of the solvents mentioned.

Suitable bases are, in general, inorganic compounds, such as alkali metal and alkaline earth metal hydrides, such as LiH, NaH, KH, $CaH_2$, and the like.

Moreover, organic bases, e.g. alkali metal amide bases, such as lithium bis(trimethylsilyl)amide, sodium bis(trimethylsilyl)amide, potassium bis(trimethylsilyl)amide, and the like, or alkali metal alcoholates, such as lithium tert-butylate, sodium tert-butylate, and potassium tert-butylate, and the like, or tertiary amines, such as triethylamine, diisopropylethylamine and N-methylpiperidine, or amidine bases such as 1,8-diazabicyclo[5.4.0]undec-7-ene (DBU), and the like. Particular preference is given to triethylamine. The bases are generally employed in equimolar amounts; however, they can also be used in excess or, if appropriate, as solvent.

Furthermore, in certain cases, it may be advantageous to employ an alkali metal or earth alkali metal additive such as LiCl, LiBr, $MgCl_2$, $MgBr_2$, and the like, in the reaction.

The starting materials are generally reacted with one another in equimolar amounts. In terms of yield, it may be advantageous to employ an excess of VII, based on VI.

Compounds VI and VII are commercially available or known from the literature [cf. e.g. WO 2005/085216, WO 2011/067272] or can be prepared in accordance with the literature cited.

Alternatively, compounds of formula II.1 can be prepared by reaction of an isoxazoline halogen compound of formula VIII, wherein $X^H$ is a halogen, preferably a bromide or chloride, with an amine of formula IXa (X═NHR$^3$) in an acid-promoted ipso-substitution reaction:

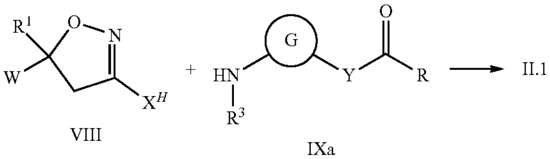

II.1

VIII IXa

This transformation is usually carried out at temperatures of from 25° C. to 200° C., preferably from 60° C. to 150° C., in an inert solvent, in the presence of an acid.

Suitable solvents are alcohols such as 2,4-dimethylpentan-3-ol, n-butanol, sec-butanol, tert-butanol, and the like, or aromatic hydrocarbons such as toluene, o-, m-, p-xylene, chlorobenzene, dichlorobenzene, and the like, moreover, DMSO, DMF, and DMA, NMP, and the like, preferably alcohols such as 2,4-dimethylpentan-3-ol are employed. It is also possible to use mixtures of the solvents mentioned.

Suitable acids and acidic catalysts are in general inorganic acids such as, HCl, HBr, $H_2SO_4$, $HClO_4$, and the like, moreover, organic acids such as toluenesulfonic acid, benzenesulfonic acid, camphor sulfonic acid, trifluoromethanesulfonic acid, trifluoroacetic acid, and the like. The acids are generally employed in catalytic amounts; however, they can also be used in equimolar amounts, in excess or, if appropriate, as solvent.

The starting materials are generally reacted with one another in equimolar amounts. In terms of yield, it may be advantageous to employ an excess of IXa, based on VIII.

Compounds IX are commercially available or known from the literature [cf. WO 2016/168056, WO 2016/168058, WO 2016/168059, WO 2018/071327, WO 2019/194982, WO 2010/135360] or can be prepared in accordance with the literature cited.

Compounds of formula VIII, on the other hand, can be prepared by reacting an olefin of formula X with a dihaloformaldoxime of formula XI in a 1,3-dipolar cycloaddition reaction:

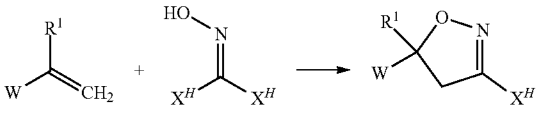

X XI VIII

This transformation is usually carried out at temperatures of from 0° C. to 100° C., preferably from 25° C. to 80° C., in an inert solvent, in the presence of a base [cf. WO 2010/135360].

Suitable solvents are esters such as ethyl acetate, and the like, or water, and it is also possible to use mixtures of the solvents mentioned. Suitable bases are, in general, inorganic compounds, such as alkali metal and alkaline earth metal carbonates, such as $Li_2CO_3$, $K_2CO_3$, and $CaCO_3$, and also alkali metal bicarbonates such as $NaHCO_3$. Particular preference is given to alkali metal bicarbonates such as $NaHCO_3$. The bases are generally employed in excess; however, they can also be used in equimolar amounts.

The starting materials are generally reacted with one another in equimolar amounts. In terms of yield, it may be advantageous to employ an excess of XI, based on X.

Compounds of formula X, in turn, can be prepared by reacting a ketone of formula VI with methyltriphenylphosphonium bromide in a Wittig reaction:

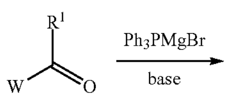

X

VI

The Wittig reaction is conducted under conditions known in the art, preferably at temperatures of from 0° C. to 60° C., in an inert solvent such as THF, in the presence of a base such as potassium tert-butoxide.

In addition, compounds of formula II can also be prepared by reaction of an isoxazoline halogen compound of formula VIII, wherein $X^H$ is a halogen, preferably a bromide or chloride, with a compound of formula IX in a base-promoted ipso-substitution reaction:

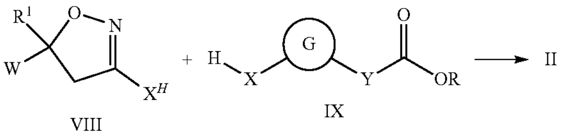

VIII IX

This transformation is usually carried out at temperatures of from 25° C. to 200° C., preferably from 60° C. to 150° C., in an inert solvent, in the presence of a base [cf. WO 2010/135360].

Suitable solvents are DMF, DMA, NMP, DMSO, and the like, preferably DMF or NMP are used. It is also possible to use mixtures of the solvents mentioned.

Suitable bases are, in general, inorganic compounds, such as alkali metal and alkaline earth metal hydroxides, such as LiOH, NaOH, KOH, $Ca(OH)_2$, and the like, or alkali metal and alkaline earth metal hydrides, such as LiH, NaH, KH, $CaH_2$, and the like, or alkali metal and alkaline earth metal carbonates, such as $Li_2CO_3$, $K_2CO_3$, and $CaCO_3$. The bases are generally employed in equimolar amounts; however, they can also be used in in excess or, if appropriate, as solvent.

Furthermore, compounds of formula II can be prepared by reaction of an olefin of formula X, with an oxime of formula XII, wherein Ar is an aromatic group, in a 1,3-dipolar cycloaddition:

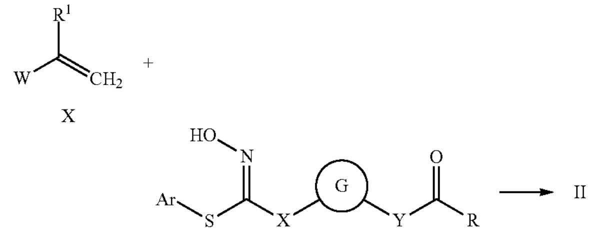

X

XII

This transformation is usually carried out at temperatures of from 0° C. to 100° C., preferably from 25° C. to 60° C., in an inert solvent, in the presence of a base and a silver(I) salt, such as e.g. silver nitrate [cf. WO 2010/135360].

Suitable solvents are nitriles such as acetonitrile, propionitrile, and the like. Suitable bases are, in general, inorganic compounds, such as alkali metal and alkaline earth metal carbonates, such as $Li_2CO_3$, $K_2CO_3$, and $CaCO_3$, and also alkali metal bicarbonates, such as $NaHCO_3$. Particular preference is given to $K_2CO_3$. The bases are generally employed in equimolar amounts; however, they can also be used in excess or, if appropriate, as solvent.

The starting materials are generally reacted with one another in equimolar amounts. In terms of yield, it may be advantageous to employ an excess of X, based on XII.

Compounds XII can be prepared as described in the literature [cf. WO 2010/135360] or can be prepared in accordance with the literature cited.

Compounds of formula I', that is compounds of formula I wherein U is S, can be prepared by reacting the corresponding oxocompound (U is O) with Lawesson's reagent (CAS 19172-47-5), see, e.g. Jesberger et al. Synthesis, 2003, 1929-1958 and references therein. Solvents such as HMPA or THF at an elevated temperature such as 60° C. to 100° C. can be used. Preferred reaction conditions are in THF at 65° C.

The starting materials required for preparing the compounds I are commercially available or known from the literature [cf. e.g. WO 2005/085216, WO 2010/135360, WO 2011/067272, WO 2016/168056, WO 2016/168058, WO 2016/168059, WO 2018/071327, WO 2019/194982] or can be prepared in accordance with the literature cited.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, purification can also be carried out by recrystallization or digestion.

If individual compounds I cannot be obtained by the routes described above, they can be prepared by derivatization of other compounds I.

However, if the synthesis yields mixtures of isomers, a separation is generally not necessarily required since in some cases the individual isomers can be interconverted during work-up for use or during application (e.g. under the action of light, acids or bases). Such conversions may also take place after use, e.g. in the treatment of plants in the treated plant, or in the pest to be controlled.

In a preferred embodiment, the compounds I are present in form of a mixture of compounds I.A and I.B, wherein compound I.A with S-configuration in the isoxazoline ring is present in an amount of more than 50% by weight, in particular of at least 70% by weight, more particularly of at least 85% by weight, specifically of at least 90% by weight, based on the total weight of compounds I.A and I.B.

I.A

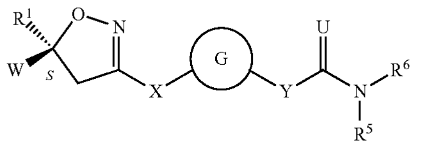

I.B

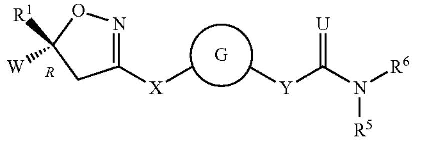

In one particularly preferred embodiment of the invention, the method comprises the step of contacting the plant, parts of it, its propagation material, the pests, their food supply, habitat or breeding grounds a pesticidally effective amount of a compound of formula I.A.

Compounds of formula IA, and I.B, resp., can be obtained in enantiopure form by known separation methods, preferably by chiral chromatography. This is preferably applied to intermediate compounds of formula III and IIIa, or to compounds of formula II and IIa.

The organic moieties groups mentioned in the above definitions of the variables are—like the term halogen— collective terms for individual listings of the individual group members. The prefix Cn-Cm indicates in each case the possible number of carbon atoms in the group.

The term "partially or fully substituted" by a radical means that in general the group is substituted with same or different radicals.

The term "halogen" denotes in each case fluorine, bromine, chlorine, or iodine, in particular fluorine, chlorine, or bromine.

The term "alkyl" as used herein and in the alkyl moieties of alkylamino, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are methyl (Me), ethyl (Et), n-propyl (n-Pr), iso-propyl, n-butyl, 2-butyl, iso-butyl, tert-butyl, n-pentyl, 1-me¬thylbutyl, 2 methylbutyl, 3 methylbutyl, 2,2-di¬methylpropyl, 1 ethylpropyl, n-hexyl, 1,1-dimethyl-propyl, 1,2-dimethylpropyl, 1-methylpentyl, 2-methylpentyl, 3-methylpentyl, 4-methylpentyl, 1,1-dimethyl¬butyl, 1,2-dimethylbutyl, 1,3-dimethyl¬butyl, 2,2-dimethylbutyl, 2,3-dimethylbutyl, 3,3-dimethyl¬butyl, 1-ethylbutyl, 2-ethylbutyl, 1,1,2-trimethylpropyl, 1,2,2-trimethylpropyl, 1-ethyl-1-methyl¬propyl, and 1-ethyl-2-methylpropyl.

The term "haloalkyl" as used herein and in the haloalkyl moieties of haloalkylcarbonyl, haloalkoxycarbonyl, haloalkylthio, haloalkylsulfonyl, haloalkylsulfinyl, haloalkoxy and haloalkoxyalkyl, denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-halo¬alkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2 difluoroethyl, 2,2,2-trifluoroethyl, pentafluoroethyl, and the like.

The term "alkoxy" as used herein denotes in each case a straight-chain or branched alkyl group which is bonded via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-prop¬oxy, n-butyloxy, 2-butyloxy, iso-butyloxy, tert-butyloxy, and the like.

The term "alkoxyalkyl" as used herein refers to alkyl usually comprising 1 to 10, frequently 1 to 4, preferably 1 to 2 carbon atoms, wherein 1 carbon atom carries an alkoxy radical usually comprising 1 to 4, preferably 1 or 2 carbon atoms as defined above. Examples are $CH_2OCH_3$, $CH_2$—$OC_2H_5$, 2-(methoxy)ethyl, and 2-(ethoxy)ethyl.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1 fluoroethoxy, 2-fluoroethoxy, 2,2 difluoroethoxy, 2,2,2-trifluoroethoxy, 2-chloro-2-fluoroethoxy, 2-chloro-2,2-difluoro-ethoxy, 2,2dichloro-2-fluorethoxy, 2,2,2-trichloroethoxy, penta¬fluoroethoxy and the like.

The term "alkylthio "(alkylsulfanyl: alkyl-S—)" as used herein refers to a straight-chain or branched saturated alkyl group having 1 to 10 carbon atoms, preferably 1 to 4 carbon atoms (═$C_1$-$C_4$-alkylthio), more preferably 1 to 3 carbon atoms, which is attached via a sulfur atom.

The term "haloalkylthio" as used herein refers to an alkylthio group as mentioned above wherein the hydrogen atoms are partially or fully substituted by fluorine, chlorine, bromine and/or iodine.

The term "alkylsulfinyl" (alkylsulfoxyl: $C_1$-$C_6$-alkyl-S(O)—), as used herein refers to a straight-chain or branched saturated alkyl group (as mentioned above) having 1 to 10 carbon atoms, preferably 1 to 4 carbon atoms (═$C_1$-$C_4$-alkylsulfinyl), more preferably 1 to 3 carbon atoms bonded through the sulfur atom of the sulfinyl group at any position in the alkyl group.

The term "haloalkylsulfinyl" as used herein refers to an alkylsulfinyl group as mentioned above wherein the hydrogen atoms are partially or fully substituted by fluorine, chlorine, bromine and/or iodine.

The term "alkylsulfonyl" (alkyl-$S(O)_2$—) as used herein refers to a straight-chain or branched saturated alkyl group having 1 to 10 carbon atoms, preferably 1 to 4 carbon atoms (═$C_1$-$C_4$-alkylsulfonyl), preferably 1 to 3 carbon atoms, which is bonded via the sulfur atom of the sulfonyl group at any position in the alkyl group.

The term "haloalkylsulfonyl" as used herein refers to an alkylsulfonyl group as mentioned above wherein the hydrogen atoms are partially or fully substituted by fluorine, chlorine, bromine and/or iodine.

The term "alkylcarbonyl" refers to an alkyl group as defined above, which is bonded via the car-bon atom of a carbonyl group (C═O) to the remainder of the molecule.

The term "haloalkylcarbonyl" refers to an alkylcarbonyl group as mentioned above, wherein the hydrogen atoms are partially or fully substituted by fluorine, chlorine, bromine and/or iodine.

The term "alkoxycarbonyl" refers to an alkylcarbonyl group as defined above, which is bonded via an oxygen atom to the remainder of the molecule.

The term "haloalkoxycarbonyl" refers to an alkoxycarbonyl group as mentioned above, wherein the hydrogen atoms are partially or fully substituted by fluorine, chlorine, bromine and/or iodine.

The term "alkenyl" as used herein denotes in each case a singly unsaturated hydrocarbon radical having usually 2 to 10, frequently 2 to 6, preferably 2 to 4 carbon atoms, e.g. vinyl, allyl (2-propen-1-yl), 1-propen-1-yl, 2 propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "haloalkenyl" as used herein refers to an alkenyl group as defined above, wherein the hydrogen atoms are partially or totally replaced with halogen atoms.

The term "alkynyl" as used herein denotes in each case a singly unsaturated hydrocarbon radical having usually 2 to 10, frequently 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "cycloalkyl" as used herein and in the cycloalkyl moieties of cycloalkoxy and cycloalkylthio denotes in each case a monocyclic cycloaliphatic radical having usually from 3 to 10 or from 3 to 6 carbon atoms, such as cyclopropyl (c-$C_3H_5$), cyclobutyl, cyclopentyl, cyclohexyl, cycloheptyl, cyclooctyl, cyclononyl and cyclodecyl or cyclopropyl, cyclobutyl, cyclopentyl and cyclo-hexyl.

The term "halocycloalkyl" as used herein and in the halocycloalkyl moieties of halocycloalkoxy and halocycloalkylthio denotes in each case a monocyclic cycloaliphatic radical having usually from 3 to 10 C atoms or 3 to 6 C atoms, wherein at least one, e.g. 1, 2, 3, 4 or 5 of the hydrogen atoms, are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "halocycloalkenyl" as used herein and in the halocycloalkenyl moieties of halocycloalkenyloxy and halocycloalkenylthio denotes in each case a monocyclic singly unsaturated non-aromatic radical having usually from 3 to 10, e.g. 3 or 4 or from 5 to 10 carbon atoms, preferably from 3- to 8 carbon atoms, wherein at least one, e.g. 1, 2, 3, 4 or 5 of the hydrogen atoms, are replaced by halogen, in particular by fluorine or chlorine. Examples are 3,3-difluorocyclopropen-1-yl and 3,3-dichlorocyclopropen-1-yl.

The term "cycloalkenylalkyl" refers to a cycloalkenyl group as defined above which is bonded via an alkyl group, such as a $C_1$-$C_6$-alkyl group or a $C_1$-$C_4$-alkyl group, in particular a methyl group (=cycloalkenylmethyl), to the remainder of the molecule.

The term "carbocycle" or "carbocyclyl" includes in general a 3- to 12-membered, preferably a 3- to 8-membered or a 5- to 8-membered, more preferably a 5- or 6-membered monocyclic, non-aromatic ring comprising 3 to 12, preferably 3 to 8 or 5 to 8, more preferably 5 or 6 carbon atoms. Preferably, the term "carbocycle" covers cycloalkyl and cycloalkenyl groups as defined above.

The term "heterocycle" or "heterocyclyl" includes in general 3- to 12-membered, preferably 3- to 6-membered, in particular 6-membered monocyclic heterocyclic non-aromatic radicals. The heterocyclic non-aromatic radicals usually comprise 1, 2, 3, 4 or 5, preferably 1, 2 or 3 hetero¬atoms selected from N, O and S as ring members, wherein S-atoms as ring members may be present as S, SO or $SO_2$. Examples of 5- or 6-membered heterocyclic radicals comprise satu¬rated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxo¬thiolanyl, dihydrothienyl, S-oxodihydrothienyl, S-dioxodihydro¬thienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothio¬pyranyl, S-oxo¬dihydrothiopyranyl, S-dioxodihydrothiopyranyl, tetrahydrothiopyranyl, S-oxotetra-hydrothiopyranyl, S-dioxotetrahydrothiopyranyl, morpholinyl, thiomorpholinyl, S-oxothio¬morpho¬linyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-only, and the like.

The term "hetaryl" includes monocyclic 5- or 6-membered heteroaromatic radicals comprising as ring members 1, 2, 3 or 4 heteroatoms selected from N, O and S. N- or S-containing hetaryl groups may be present as positively charged onium, and form together with a neighbouring atom a mesoionic entity. Examples of 5- or 6 membered heteroaromatic radicals include pyridyl, i.e. 2-, 3-, or 4 pyridyl, pyrimidinyl, i.e. 2, 4- or 5-pyrimidinyl, pyrazinyl, pyridazinyl, i.e. 3- or 4 pyridazinyl, thienyl, i.e. 2- or 3-thienyl, furyl, i.e. 2- or 3-furyl, pyrrolyl, i.e. 2- or 3 pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5 isothiazolyl, pyrazolyl, i.e. 1-, 3-, 4- or 5-pyrazolyl, i.e. 1-, 2-, 4- or 5-imidazolyl, oxadiazolyl, e.g. 2- or 5 [1,3,4] oxadiazolyl, 4- or 5-(1,2,3-oxa¬diazol)yl, 3- or 5-(1,2,4-oxadiazol)yl, 2- or 5 (1,3,4-thiadiazol)yl, thiadiazolyl, e.g. 2- or 5-(1,3,4-thia¬diazol)yl, 4- or 5 (1,2,3 thiadiazol)yl, 3- or 5-(1,2,4-thiadiazol)yl, triazolyl, e.g. 1H-, 2H- or 3H 1,2,3 triazol-4-yl, 2H-triazol-3-yl, 1H-, 2H-, or 4H-1,2,4-triazolyl and tetrazolyl, i.e. 1H- or 2H tetrazolyl. The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzo¬thienyl, indolyl, ind¬azolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2 d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "heterocyclylalkyl" and "hetarylalkyl" refer to heterocyclyl or hetaryl, respectively, as defined above which are bonded via a $C_1$-$C_6$-alkyl group or a $C_1$-$C_4$-alkyl group, in particular a methyl group (=heterocyclylmethyl or hetarylmethyl, respectively), to the remainder of the molecule.

The term "arylalkyl" and "phenylalkyl" refer to aryl as defined above and phenyl, respectively, which are bonded via $C_1$-$C_6$-alkyl group or a $C_1$-$C_4$-alkyl group, in particular a methyl group (=arylmethyl or phenylmethyl), to the remainder of the molecule, examples including benzyl, 1-phenylethyl, 2-phenylethyl, 2-phenoxyethyl etc.

The terms "alkylene", "cycloalkylene", "heterocycloalkylene", "alkenylene", "cycloalkenylene", "heterocycloalkenylene" and "alkynylene" refer to alkyl, cycloalkyl, heterocycloalkyl, alkenyl, cycloalkenyl, heterocycloalkenyl and alkynyl as defined above, respectively, which are bonded to the remainder of the molecule, via two atoms, preferably via two carbon atoms, of the respective group, so that they represent a linker between two moieties of the molecule.

In a particular embodiment, the variables of the compounds of the formula I have the following meanings, these meanings, both on their own and in combination with one another, being particular embodiments of the compounds of the formula I.

Embodiments and preferred compounds of the invention for use in pesticidal methods and for insecticidal application purposes are outlined in the following paragraphs.

With respect to the variables, the particularly preferred embodiments of the intermediates correspond to those of the compounds of the formula I.

In one embodiment W is a group WA,

WA

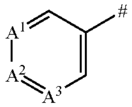

wherein $A^1$, $A^2$, $A^3$ are N or $CR^2$, provided that at least two are $CR^2$;

$R^2$ are independently from each other preferably H, halogen, $C_1$-$C_4$-haloalkyl, $C_1$-$C_4$-halocycloalkyl, $C_1$-$C_3$-haloalkoxy, $S(O)_m$—$C_1$-$C_3$-alkyl, $S(O)_m$—$C_1$-$C_3$-haloalkyl.

W is preferably a group WP:

WP

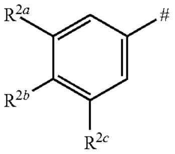

wherein $R^{2a}$, $R^{2b}$, and $R^{2c}$ are a group $R^2$.

$R^{2a}$ is preferably selected from F, Cl, Br, $CF_3$, $SCF_3$, and $OCF_3$.

$R^{2b}$ and $R^{2c}$ are independently preferably selected from H, F, Cl, Br, $CF_3$, $SCF_3$, and $OCF_3$.

Particularly preferred is each one of the following combinations of $R^{2a}$, $R^{2b}$ and $R^{2c}$ wherein each line of Table W denotes a substitution pattern of the phenyl ring ("WP") bearing the $R^{2a}$, $R^{2b}$ and $R^{2c}$ moieties.

TABLE W

| No. | $R^{2a}$ | $R^{2b}$ | $R^{2c}$ |
|---|---|---|---|
| W-1 | F | F | H |
| W-2 | F | H | F |
| W-3 | F | F | F |
| W-4 | F | Cl | F |
| W-5 | F | Br | F |
| W-6 | F | H | Cl |
| W-7 | F | H | Br |
| W-8 | Cl | F | H |
| W-9 | Cl | H | Cl |
| W-10 | Cl | Cl | Cl |
| W-11 | Cl | F | Cl |
| W-12 | Cl | Br | Cl |
| W-13 | Cl | H | Br |
| W-14 | Br | F | H |
| W-15 | Br | H | Br |
| W-16 | Br | F | Br |
| W-17 | Br | Cl | Br |
| W-18 | $CF_3$ | H | H |
| W-19 | $CF_3$ | H | F |
| W-20 | $CF_3$ | H | Cl |
| W-21 | $CF_3$ | H | Br |
| W-22 | $CF_3$ | H | $CF_3$ |
| W-23 | $CF_3$ | F | F |
| W-24 | $CF_3$ | F | Cl |
| W-25 | $CF_3$ | Cl | Cl |
| W-26 | $CF_3$ | F | H |
| W-27 | $OCF_3$ | H | F |
| W-28 | $OCF_3$ | H | Cl |
| W-29 | $OCF_3$ | F | H |
| W-30 | $OCF_3$ | H | $CF_3$ |
| W-31 | $OCF_3$ | H | H |
| W-32 | Cl | $OCF_3$ | H |
| W-33 | $SCF_3$ | H | Cl |

Groups W-8, W-9, and W-11 are more preferred patterns in formula I compounds. W-11 is particularly preferred.

Another embodiment of W is a 5- or 6-membered hetaryl, such as thiophene, pyrazole, imidazole, or pyridine, which rings are substituted with 1 or 2 groups $R^{2a}$ or $C_1$-$C_2$-alkoxy-$C_1$-$C_2$-alkyl.

$R^1$ is preferably $CF_3$.

X is preferably N—$R^3$. In another preferred embodiment X is N—$R^3$ or O.

In one embodiment of formula I compounds as defined in claim 1 $R^{21}$ is H, $C_1$-$C_6$-alkyl, $C_2$-$C_6$-alkenyl, $C_2$-$C_6$-alkynyl, $C_3$-$C_8$-cycloalkyl, or $Si(C_1$-$C_4$-$alkyl)_3$, which groups are unsubstituted, partially or fully substituted with $R^{211}$.

$R^3$ is preferably H, $C_1$-$C_4$-alkyl, unsubstituted or substituted with 1 or 2 groups CN, $C_3$-$C_4$-cycloalkyl, $C_1$-$C_2$-alkoxy, 4-membered herocyclyl comprising as ring members a hetero¬atom selected from N, O, and $S(O)_m$. $R^3$ being H or $CH_3$ is particularly preferred.

In another embodiment $R^3$ is OH, $C_1$-$C_4$-alkoxy, or $C_1$-$C_4$-alkoxycarbonyl.

In one embodiment G is a group GQ:

GQ

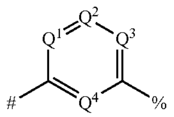

wherein $Q^1$, $Q^2$, $Q^3$, $Q^4$ are N or $CR^4$; provided that at least three are $CR^4$;

$R^4$ are independently from each other preferably H, halogen, CN, $C_1$-$C_4$-alkyl, $C_1$-$C_4$-cycloalkyl, $C_1$-$C_4$-haloalkyl, $C_1$-$C_4$-halocycloalkyl, $C_1$-$C_3$-alkoxy, $C_1$-$C_3$-haloalkoxy, $S(O)_m$—$C_1$-$C_3$-alkyl, $S(O)_mC_1$-$C_3$-haloalkyl.

G is preferably a group G1, G2, G3, or G4:

G1

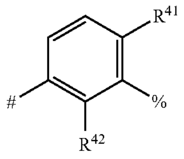

G2

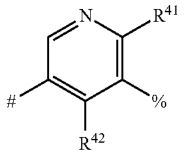

G3

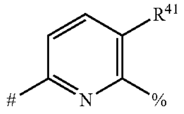

G4

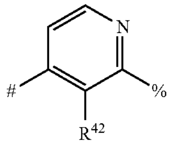

wherein # is the bond to X, % is the bond to Y which is a direct bond, and $R^{41}$ and $R^{42}$ are H or a group $R^4$, preferably H, or halogen, CN, halomethyl, halomethoxy. In a particularly preferred embodiment $R^{41}$ is halogen such as C, and $R^{42}$ is H.

Another embodiment of G is a 5-membered hetaryl, such as thiophene, or imidazole, which rings are substituted with a group $R^{2a}$ or $C_1$-$C_2$-alkoxy.

Y is preferably a direct bond.

In another embodiment Y is a spacer $CR^7R^8$. In such group $R^7$ and $R^8$ are preferably both H or halogen such as F, or both $R^7$ and $R^8$ together form a 3- or 4-membered saturated carbocycle.

Preferably $R^5$ is $C_1$-$C_4$-alkyl, $C_1$-$C_4$-haloalkyl, $C_3$-$C_4$-cycloalkyl optionally substituted, phenyl substituted with 1 or 2 halogen, $NH_2$, NHC(O)—$C_1$-$C_4$-alkyl, 6-membered hetaryl comprising as ring members 1-3 N atoms.

In another embodiment $R^5$ is cyclopropyl which is substituted with CN, $C_1$-$C_2$-alkyl, $C_1$-$C_2$-haloalkyl, or 3-, 4-, 5-, or 6-membered partially or fully unsubstituted heterocycle comprising as ring members 1 to 4 hetero¬atoms selected from N, O, and $S(O)_m$ which heterocycle is optionally substituted with halogen, CN, $C_1$-$C_4$-alkyl, cyano-$C_1$-$C_4$-alkyl, $C_1$-$C_4$-haloalkyl, $C_1$-$C_2$-alkoxy-$C_1$-$C_2$-alkyl, and/or oxo.

In another embodiment $R^5$ is phenyl which is substituted with 1 or 2 substituents halogen, CN, $C_1$-$C_4$-alkyl, $C_1$-$C_4$-haloalkyl, $NH_2$, NHC(O)—$C_1$-$C_4$-alkyl, NHC(O)—$C_1$-$C_4$-haloalkyl, NHC(O)—$C_1$-$C_4$-alkoxy, NHC(O)—$C_1$-$C_2$-alkyl-$C_3$-$C_4$-cycloalkyl.

$R^6$ is preferably H or $C_1$-$C_4$-alkyl, $C_3$-$C_4$-cycloalkyl-$C_1$-$C_2$-alkyl, $C_1$-$C_4$-alkylcarbonyl, or $C_1$-$C_4$-alkoxycarbonyl. Particularly preferred is $R^6$ is H or $C_1$-$C_2$-alkyl.

A preferred embodiment are compounds of formula I, wherein $R^1$ is $C_1$-$C_2$-haloalkyl;

W is phenyl, or 5- or 6-membered heteroaryl comprising as ring members 1, 2, or 3 heteroatoms selected from N, O, and S; wherein W is unsubstituted, partially or fully substituted with $R^2$;

$R^2$ is halogen, $OR^{21}$, $C_1$-$C_4$-haloalkyl, $C_1$-$C_3$-alkoxy, $C_1$-$C_3$-haloalkoxy, $C_1$-$C_3$-alkyl-$S(O)_m$, $C_1$-$C_3$-haloalkyl-$S(O)_m$, $C_1$-$C_3$-alkoxy-$C_1$-$C_4$-alkyl; which groups are optionally substituted with $R^{211}$; m is 0, 1, or 2;

$R^{21}$ H, $C_1$-$C_6$-alkyl, which groups are unsubstituted, partially or fully substituted with $R^{211}$; $R^{211}$ halogen;

X is $NR^3$, O, or $S(O)_m$; $R^3$ is $OR^{21}$ or a group as defined for $R^5$;

G is phenyl, or 5- or 6-membered heteroaryl comprising as ring members 1, 2, or 3 heteroatoms selected from N, O and S; wherein G is unsubstituted, partially, or fully substituted with $R^4$; $R^4$ is a group as defined for $R^2$ U is O;

$R^5$ is H, $C_1$-$C_6$-alkyl, $C_1$-$C_6$-haloalkyl, which are unsubstituted or partially or fully substituted with $R^{51}$; or $N(R^{12a})R^{12b}$, $S(O)_mR^{13}$, C(═O)$OR^{13}$, C(═U)$N(R^{12a})R^{12b}$ $C_3$-$C_8$-cycloalkyl, $C_3$-$C_8$-halocycloalkyl, phenyl, a 3-, 4-, 5-, 6- or 7-membered saturated or partially unsaturated heterocycle comprising 1, 2, 3 or 4 heteroatoms selected from N, O, and $S(O)_m$ as ring members, or a 5- or 6-membered hetaryl comprising 1, 2, 3 or 4 heteroatoms selected from N, O, and $S(O)_m$ as ring members, which rings are unsubstituted or partially or fully substituted with $R^{52}$;

$R^{51}$ halogen, CN, $N(R^{12a})R^{12b}$, C(═O)$N(R^{12a})R^{12b}$; $C_3$-$C_8$-cycloalkyl which is unsubstituted, partially halogenated and/or substituted with CN;

$S(O)_mR^{13}$, C(═U)$N(R^{12a})R^{12b}$; phenyl, or 3-, 4-, 5-, 6- or 7-membered saturated, partially or fully unsaturated heterocycle containing 1, 2, or 3 heteroatoms selected from N, O, $S(O)_m$ as ring members; or $R^{52}$ is a group as defined in $R^{51}$;

$R^6$ is a group as defined for $R^5$; or $R^5$ and $R^6$ together with the nitrogen they are bound to form a mesoionic entity;

Y having at G one or two ring atoms of G between connection points of G to X and Y; Y being a direct bond or $CR^7R^8$; $R^7$, $R^8$ are H, or halogen.

A preferred embodiment are compounds of formula I which correspond to formula I' as depicted below, wherein the variables are defined and preferred as above.

I'

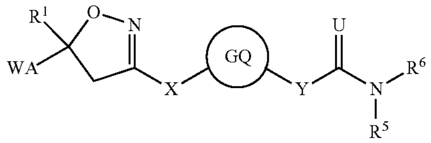

Another preferred embodiment are compounds of formula I which correspond to formula I.1 as depicted below, wherein the variables are defined and preferred as above.

I.1

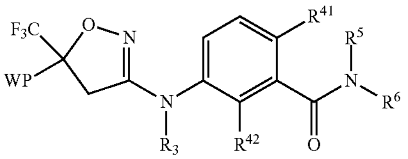

Another preferred embodiment are compounds of formula I which correspond to formula I.2 as depicted below, wherein the variables are defined and preferred as above. One embodiment relates to formula I.2 compounds wherein X is O or $S(O)_m$, particularly O.

Another preferred embodiment are compounds of formula I which correspond to formula I.3 as depicted below, wherein the variables are defined and preferred as above. One embodiment relates to formula I.3 compounds wherein X is $NR^3$, particularly NH.

I.2

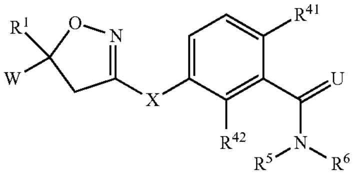

I.3

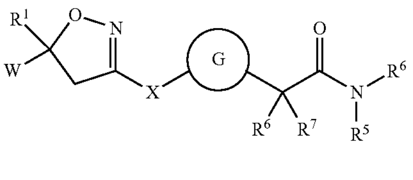

In particular with a view to their use, preference is given to the compounds of formula I compiled in the tables below, which compounds correspond to formula I.1 wherein $R^{42}$ denotes H. Each of the groups mentioned for a substituent in the tables is furthermore per se, independently of the combination in which it is mentioned, a particularly preferred aspect of the substituent in question.

Table 1: Compounds of formula I.1 in which $R^5$ is H, $R^6$ is c-$C_3H_5$, and the other variables for a compound correspond in each case to one row of Table A Table 2: Compounds of formula I.1 in which $R^5$ is $CH_3$, $R^6$ is c-$C_3H_5$, and the other variables for a compound correspond in each case to one row of Table A Table 3: Compounds of formula I.1 in which $R^5$ is $CH_2CH_3$, $R^6$ is c-$C_3H_5$, and the other variables for a compound correspond in each case to one row of Table A Table 4: Compounds of formula I.1 in which $R^5$ is H, $R^6$ is (1-CN)-c-$C_3H_4$, and the other variables for a compound correspond in each case to one row of Table A Table 5: Compounds of formula I.1 in which $R^5$ is $CH_3$, $R^6$ is (1-CN)-c-$C_3H_4$, and the other variables for a compound correspond in each case to one row of Table A Table 6: Compounds of formula I.1 in which $R^5$ is $CH_2CH_3$, $R^6$ is (1-CN)-c-$C_3H_4$, and the other variables for a compound correspond in each case to one row of Table A Table 7: Compounds of formula I.1 in which $R^5$ is H, $R^6$ is $CH_2CF_3$, and the other variables for a compound correspond in each case to one row of Table A Table 8: Compounds of formula I.1 in which $R^5$ is $CH_3$, $R^6$ is $CH_2CF_3$, and the other variables for a compound correspond in each case to one row of Table A Table 9: Compounds of formula I.1 in which $R^5$ is $CH_2CH_3$, $R^6$ is $CH_2CF_3$, and the other variables for a compound correspond in each case to one row of Table A Table 10: Compounds of formula I.1 in which $R^5$ is H, $R^6$ is 2,4-$F_2$—$C_6H_3$, and the other variables for a compound correspond in each case to one row of Table A Table 11: Compounds of formula I.1 in which $R^5$ is $CH_3$, $R^6$ is 2,4-$F_2$—$C_6H_3$, and the other variables for a compound correspond in each case to one row of Table A Table 12: Compounds of formula I.1 in which $R^5$ is $CH_2CH_3$, $R^6$ is 2,4-$F_2$—$C_6H_3$, and the other variables for a compound correspond in each case to one row of Table A Table 13: Compounds of formula I.1 in which $R^5$ is H, $R^6$ is (4R)-2-ethyl-3-oxo-isoxazolidin-4-yl, and the other variables for a compound correspond in each case to one row of Table A Table 14: Compounds of formula I.1 in which $R^5$ is $CH_3$, $R^6$ is (4R)-2-ethyl-3-oxo-isoxazolidin-4-yl, and the other variables for a compound correspond in each case to one row of Table A Table 15: Compounds of formula I.1 in which $R^5$ is $CH_2CH_3$, $R^6$ is (4R)-2-ethyl-3-oxo-isoxazolidin-4-yl, and the other variables for a compound correspond in each case to one row of Table A

TABLE A

| No. | WP | $R^3$ | $R^{41}$ |
|---|---|---|---|
| A-1 | W-8 | H | Cl |
| A-2 | W-9 | H | Cl |
| A-3 | W-10 | H | Cl |
| A-4 | W-11 | H | Cl |
| A-5 | W-18 | H | Cl |
| A-6 | W-20 | H | Cl |
| A-7 | W-26 | H | Cl |
| A-8 | W-29 | H | Cl |
| A-9 | W-8 | $CH_3$ | Cl |
| A-10 | W-9 | $CH_3$ | Cl |
| A-11 | W-10 | $CH_3$ | Cl |
| A-12 | W-11 | $CH_3$ | Cl |
| A-13 | W-18 | $CH_3$ | Cl |
| A-14 | W-20 | $CH_3$ | Cl |
| A-15 | W-26 | $CH_3$ | Cl |
| A-16 | W-29 | $CH_3$ | Cl |
| A-17 | W-8 | $CH_2CH_3$ | Cl |
| A-18 | W-9 | $CH_2CH_3$ | Cl |
| A-19 | W-10 | $CH_2CH_3$ | Cl |
| A-20 | W-11 | $CH_2CH_3$ | Cl |
| A-21 | W-18 | $CH_2CH_3$ | Cl |
| A-22 | W-20 | $CH_2CH_3$ | Cl |
| A-23 | W-26 | $CH_2CH_3$ | Cl |
| A-24 | W-29 | $CH_2CH_3$ | Cl |
| A-25 | W-8 | $CH_2OCH_3$ | Cl |
| A-26 | W-9 | $CH_2OCH_3$ | Cl |
| A-27 | W-10 | $CH_2OCH_3$ | Cl |
| A-28 | W-11 | $CH_2OCH_3$ | Cl |
| A-29 | W-18 | $CH_2OCH_3$ | Cl |
| A-30 | W-20 | $CH_2OCH_3$ | Cl |
| A-31 | W-26 | $CH_2OCH_3$ | Cl |
| A-32 | W-29 | $CH_2OCH_3$ | Cl |
| A-33 | W-8 | H | $CH_3$ |
| A-34 | W-9 | H | $CH_3$ |
| A-35 | W-10 | H | $CH_3$ |
| A-36 | W-11 | H | $CH_3$ |
| A-37 | W-18 | H | $CH_3$ |
| A-38 | W-20 | H | $CH_3$ |
| A-39 | W-26 | H | $CH_3$ |
| A-40 | W-29 | H | $CH_3$ |
| A-41 | W-8 | $CH_3$ | $CH_3$ |
| A-42 | W-9 | $CH_3$ | $CH_3$ |
| A-43 | W-10 | $CH_3$ | $CH_3$ |
| A-44 | W-11 | $CH_3$ | $CH_3$ |
| A-45 | W-18 | $CH_3$ | $CH_3$ |
| A-46 | W-20 | $CH_3$ | $CH_3$ |
| A-47 | W-26 | $CH_3$ | $CH_3$ |
| A-48 | W-29 | $CH_3$ | $CH_3$ |
| A-49 | W-8 | $CH_2CH_3$ | $CH_3$ |
| A-50 | W-9 | $CH_2CH_3$ | $CH_3$ |
| A-51 | W-10 | $CH_2CH_3$ | $CH_3$ |
| A-52 | W-11 | $CH_2CH_3$ | $CH_3$ |
| A-53 | W-18 | $CH_2CH_3$ | $CH_3$ |
| A-54 | W-20 | $CH_2CH_3$ | $CH_3$ |
| A-55 | W-26 | $CH_2CH_3$ | $CH_3$ |
| A-56 | W-29 | $CH_2CH_3$ | $CH_3$ |
| A-57 | W-8 | $CH_2OCH_3$ | $CH_3$ |
| A-58 | W-9 | $CH_2OCH_3$ | $CH_3$ |
| A-59 | W-10 | $CH_2OCH_3$ | $CH_3$ |
| A-60 | W-11 | $CH_2OCH_3$ | $CH_3$ |
| A-61 | W-18 | $CH_2OCH_3$ | $CH_3$ |
| A-62 | W-20 | $CH_2OCH_3$ | $CH_3$ |
| A-63 | W-26 | $CH_2OCH_3$ | $CH_3$ |
| A-64 | W-29 | $CH_2OCH_3$ | $CH_3$ |
| A-65 | W-8 | H | $OCF_3$ |
| A-66 | W-9 | H | $OCF_3$ |
| A-67 | W-10 | H | $OCF_3$ |
| A-68 | W-11 | H | $OCF_3$ |
| A-69 | W-18 | H | $OCF_3$ |
| A-70 | W-20 | H | $OCF_3$ |
| A-71 | W-26 | H | $OCF_3$ |
| A-72 | W-29 | H | $OCF_3$ |
| A-73 | W-8 | $CH_3$ | $OCF_3$ |
| A-74 | W-9 | $CH_3$ | $OCF_3$ |
| A-75 | W-10 | $CH_3$ | $OCF_3$ |
| A-76 | W-11 | $CH_3$ | $OCF_3$ |
| A-77 | W-18 | $CH_3$ | $OCF_3$ |
| A-78 | W-20 | $CH_3$ | $OCF_3$ |
| A-79 | W-26 | $CH_3$ | $OCF_3$ |
| A-80 | W-29 | $CH_3$ | $OCF_3$ |
| A-81 | W-8 | $CH_2CH_3$ | $OCF_3$ |
| A-82 | W-9 | $CH_2CH_3$ | $OCF_3$ |
| A-83 | W-10 | $CH_2CH_3$ | $OCF_3$ |
| A-84 | W-11 | $CH_2CH_3$ | $OCF_3$ |
| A-85 | W-18 | $CH_2CH_3$ | $OCF_3$ |
| A-86 | W-20 | $CH_2CH_3$ | $OCF_3$ |

TABLE A-continued

| No. | WP | $R^3$ | $R^{41}$ |
|---|---|---|---|
| A-87 | W-26 | $CH_2CH_3$ | $OCF_3$ |
| A-88 | W-29 | $CH_2CH_3$ | $OCF_3$ |
| A-89 | W-8 | $CH_2OCH_3$ | $OCF_3$ |
| A-90 | W-9 | $CH_2OCH_3$ | $OCF_3$ |
| A-91 | W-10 | $CH_2OCH_3$ | $OCF_3$ |
| A-92 | W-11 | $CH_2OCH_3$ | $OCF_3$ |
| A-93 | W-18 | $CH_2OCH_3$ | $OCF_3$ |
| A-94 | W-20 | $CH_2OCH_3$ | $OCF_3$ |
| A-95 | W-26 | $CH_2OCH_3$ | $OCF_3$ |
| A-96 | W-29 | $CH_2OCH_3$ | $OCF_3$ |
| A-97 | W-8 | H | CN |
| A-98 | W-9 | H | CN |
| A-99 | W-10 | H | CN |
| A-100 | W-11 | H | CN |
| A-101 | W-18 | H | CN |
| A-102 | W-20 | H | CN |
| A-103 | W-26 | H | CN |
| A-104 | W-29 | H | CN |
| A-105 | W-8 | $CH_3$ | CN |
| A-106 | W-9 | $CH_3$ | CN |
| A-107 | W-10 | $CH_3$ | CN |
| A-108 | W-11 | $CH_3$ | CN |
| A-109 | W-18 | $CH_3$ | CN |
| A-110 | W-20 | $CH_3$ | CN |
| A-111 | W-26 | $CH_3$ | CN |
| A-112 | W-29 | $CH_3$ | CN |
| A-113 | W-8 | $CH_2CH_3$ | CN |
| A-114 | W-9 | $CH_2CH_3$ | CN |
| A-115 | W-10 | $CH_2CH_3$ | CN |
| A-116 | W-11 | $CH_2CH_3$ | CN |
| A-117 | W-18 | $CH_2CH_3$ | CN |
| A-118 | W-20 | $CH_2CH_3$ | CN |
| A-119 | W-26 | $CH_2CH_3$ | CN |
| A-120 | W-29 | $CH_2CH_3$ | CN |
| A-121 | W-8 | $CH_2OCH_3$ | CN |
| A-122 | W-9 | $CH_2OCH_3$ | CN |
| A-123 | W-10 | $CH_2OCH_3$ | CN |
| A-124 | W-11 | $CH_2OCH_3$ | CN |
| A-125 | W-18 | $CH_2OCH_3$ | CN |
| A-126 | W-20 | $CH_2OCH_3$ | CN |
| A-127 | W-26 | $CH_2OCH_3$ | CN |
| A-128 | W-29 | $CH_2OCH_3$ | CN |

The term "compound(s) of the invention" refers to compound(s) of formula I, or "compound(s) I", and includes their salts, tautomers, stereoisomers, and N-oxides.

The invention also relates to agrochemical compositions comprising an auxiliary and at least one compound I.

An agrochemical composition comprises a pesticidally effective amount of a compound I.

The compounds I can be converted into customary types of agro-chemical compositions, e.g. solutions, emulsions, suspensions, dusts, powders, pastes, granules, pressings, capsules, and mixtures thereof. Examples for composition types are suspensions (e.g. SC, OD, FS), emulsifyable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials e.g. seeds (e.g. GF). These and further compositions types are defined in the "Catalogue of pesticide formulation types and international coding system", Technical Monograph No. 2, 6th Ed. May 2008, CropLife International. The compositions are prepared in a known manner, e.g. described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents. Suitable solid carriers or fillers are mineral earths.

Suitable surfactants are surface-active compounds, e.g. anionic, cationic, nonionic, and amphoteric surfactants, block polymers, polyelectrolytes. Such surfactants can be used as emulsifier, dispersant, solubilizer, wetter, penetration enhancer, protective colloid, or adjuvant. Surfactants are listed in McCutcheon's, Vol. 1: Emulsifiers & Detergents, McCutcheon's Directories, Glen Rock, USA, 2008 (International or North American Ed.). Suitable anionic surfactants are alkali, alkaline earth, or ammonium salts of sulfonates, sulfates, phosphates, carboxylates. Suitable nonionic surfactants are alkoxylates, N-substituted fatty acid amides, amine oxides, esters, sugar-based surfactants, polymeric surfactants. Suitable cationic surfactants are quaternary surfactants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100%.

Various types of oils, wetters, adjuvants, or fertilizer may be added to the active substances or the compositions comprising them as premix or, if appropriate not until immediately prior to use (tank mix). These agents can be admixed with the compositions according to the invention in a weight ratio of 1:100 to 100:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, of the ready-to-use spray liquor are applied per hectare of agricultural useful area.

The compounds I are suitable for use in protecting crops, plants, plant propagation materials, e.g. seeds, or soil or water, in which the plants are growing, from attack or infestation by animal pests. Therefore, the invention also relates to a plant protection method, which comprises contacting crops, plants, plant propagation materials, e.g. seeds, or soil or water, in which the plants are growing, to be protected from attack or infestation by animal pests, with a pesticidally effective amount of a compound I.

The compounds I are also suitable for use in combating or controlling animal pests. Therefore, the invention also relates to a method of combating or controlling animal pests, which comprises contacting the animal pests, their habitat, breeding ground, or food supply, or the crops, plants, plant propagation materials, e.g. seeds, or soil, or the area, material or environment in which the animal pests are growing or may grow, with a pesticidally effective amount of a compound I.

The compounds I are effective through both contact and ingestion to any and all developmental stages, such as egg, larva, pupa, and adult.

The compounds I can be applied as such or in form of compositions comprising them.

The application can be carried out both before and after the infestation of the crops, plants, plant propagation materials by the pests.

The term "contacting" includes both direct contact (applying the compounds/compositions directly on the animal pest or plant) and indirect contact (applying the compounds/compositions to the locus).

The term "animal pest" includes arthropods, gastropods, and nematodes. Preferred animal pests according to the invention are arthropods, preferably insects and arachnids, in particular insects.

The term "plant" includes cereals, e.g. durum and other wheat, rye, barley, triticale, oats, rice, or maize (fodder maize and sugar maize/sweet and field corn); beet, e.g. sugar beet, or fodder beet; fruits, e.g. pomes, stone fruits, or soft fruits, e.g. apples, pears, plums, peaches, nectarines, almonds, cherries, papayas, strawberries, raspberries, blackberries or gooseberries; leguminous plants, e.g. beans, lentils, peas, alfalfa, or soybeans; oil plants, e.g. rapeseed (oilseed rape), turnip rape, mustard, olives, sunflowers, coconut, cocoa beans, castor oil plants, oil palms, ground nuts, or soybeans; cucurbits, e.g. squashes, pumpkins, cucumber or melons; fiber plants, e.g. cotton, flax, hemp, or jute; citrus fruit, e.g. oranges, lemons, grape-fruits or mandarins; vegetables, e.g. eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, e.g. avocados, cinnamon, or camphor; energy and raw material plants, e.g. corn, soybean, rapeseed, sugar cane or oil palm; tobacco; nuts, e.g. walnuts; pistachios; coffee; tea; bananas; vines; hop; sweet leaf (Stevia); natural rubber plants or ornamental and forestry plants, shrubs, broad-leaved trees or evergreens, eucalyptus; turf; lawn; grass. Preferred plants include potatoes sugar beets, tobacco, wheat, rye, barley, oats, rice, corn, cotton, soybeans, rapeseed, legumes, sunflowers, coffee, or sugar cane; fruits; vines; ornamentals; or vegetables, e.g. cucumbers, tomatoes, beans or squashes.

The term "seed" embraces seeds and plant propagules including true seeds, seed pieces, suckers, corms, bulbs, fruit, tubers, grains, cuttings, cut shoots, and means preferably true seeds.

"Pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions e.g. desired pesticidal effect and duration, weather, target species, locus, mode of application.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare.

The compounds I are also suitable for use against non-crop insect pests. For use against said non-crop pests, compounds I can be used as bait composition, gel, general insect spray, aerosol, as ultra-low volume application and bed net (impregnated or surface applied).

The term "non-crop insect pest" refers to pests, which are particularly relevant for non-crop targets, e.g. ants, termites, wasps, flies, ticks, mosquitoes, bed bugs, crickets, or cockroaches, such as: *Aedes aegypti, Musca domestica*, Tribolium spp.; termites such as *Reticulitermes flavipes, Coptotermes formosanus*; roaches such as *Blatella germanica, Periplaneta Americana*; ants such as *Solenopsis invicta, Linepithema humile*, and *Camponotus pennsylvanicus.*

The bait can be a liquid, a solid or a semisolid preparation (e.g. a gel). For use in bait compositions, the typical content of active ingredient is from 0.001 wt % to 15 wt %, desirably from 0.001 wt % to 5 wt % of active compound.

The compounds I and its compositions can be used for protecting wooden materials such as trees, board fences, sleepers, frames, artistic artifacts, etc. and buildings, but also construction materials, furniture, leathers, fibers, vinyl articles, electric wires and cables etc. from ants, termites and/or wood or textile destroying beetles, and for controlling ants and termites from doing harm to crops or human beings (e.g. when the pests invade into houses and public facilities or nest in yards, orchards or parks).

Customary application rates in the protection of materials are, e.g., from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 wt %, preferably from 0.1 to 45 wt %, and more preferably from 1 to 25 wt % of at least one repellent and/or insecticide.

The compounds of the invention are especially suitable for efficiently combating animal pests e.g. arthropods, and nematodes including:

- insects from the sub-order of Auchenorrhyncha, e.g. *Amrasca biguttula, Empoasca* spp., *Nephotettix virescens, Sogatella furcifera, Mahanarva* spp., *Laodelphax striatellus, Nilaparvata lugens, Diaphorina citri;*
- Lepidoptera, e.g. *Helicoverpa* spp., *Heliothis virescens, Lobesia botrana, Ostrinia nubilalis, Plutella xylostella, Pseudoplusia includens, Scirpophaga incertulas, Spodoptera* spp., *Trichoplusia ni, Tuta absoluta, Cnaphalocrocis medialis, Cydia pomonella, Chilo suppressalis, Anticarsia gemmatalis, Agrotis ipsilon, Chrysodeixis includens;*
- True bugs, e.g. *Lygus* spp., Stink bugs such as *Euschistus* spp., *Halyomorpha halys, Nezara viridula, Piezodorus guildinii, Dichelops furcatus;*
- *Thrips*, e.g. *Frankliniella* spp., *Thrips* spp., *Dichromothrips corbettii;*
- Aphids, e.g. *Acyrthosiphon pisum, Aphis* spp., *Myzus persicae, Rhopalosiphum* spp., *Schizaphis graminum, Megoura viciae;*
- Whiteflies, e.g. *Trialeurodes vaporariorum, Bemisia* spp.;
- Coleoptera, e.g. *Phyllotreta* spp., *Melanotus* spp., *Meligethes aeneus, Leptinotarsa decimlineata, Ceutorhynchus* spp., *Diabrotica* spp., *Anthonomus grandis, Atomaria linearia, Agriotes* spp., *Epilachna* spp.;
- Flies, e.g. *Delia* spp., *Ceratitis capitate, Bactrocera* spp., *Liriomyza* spp.;
- *Coccoidea*, e.g. *Aonidiella aurantia, Ferrisia virgate;*
- Anthropods of class Arachnida (Mites), e.g. *Penthaleus major, Tetranychus* spp.;
- Nematodes, e.g. *Heterodera glycines, Meloidogyne* spp., *Pratylenchus* spp., *Caenorhabditis elegans.*

The compounds I are suitable for use in treating or protecting animals against infestation or infection by parasites. Therefore, the invention also relates to the use of a compound of the invention for the manufacture of a medicament for the treatment or protection of animals against infestation or infection by parasites. Furthermore, the invention relates to a method of treating or protecting animals against infestation and infection by parasites, which comprises orally, topically or parenterally administering or applying to the animals a parasiticidally effective amount of a compound I.

The invention also relates to the non-therapeutic use of compounds of the invention for treating or protecting animals against infestation and infection by parasites. Moreover, the invention relates to a non-therapeutic method of treating or protecting animals against infestation and infection by parasites, which comprises applying to a locus a parasiticidally effective amount of a compound I.

The compounds of the invention are further suitable for use in combating or controlling parasites in and on animals. Furthermore, the invention relates to a method of combating or controlling parasites in and on animals, which comprises contacting the parasites with a parasitically effective amount of a compound I.

The invention also relates to the non-therapeutic use of compounds I for controlling or combating parasites. Moreover, the invention relates to a non-therapeutic method of combating or controlling parasites, which comprises applying to a locus a parasiticidally effective amount of a compound I.

The compounds I can be effective through both contact (via soil, glass, wall, bed net, carpet, blankets or animal parts) and ingestion (e.g. baits). Furthermore, the compounds I can be applied to any and all developmental stages.

The compounds I can be applied as such or in form of compositions comprising them.

The term "locus" means the habitat, food supply, breeding ground, area, material or environment in which a parasite is growing or may grow outside of the animal.

As used herein, the term "parasites" includes endo- and ectoparasites. In some embodiments of the invention, endoparasites can be preferred. In other embodiments, ectoparasites can be preferred. Infestations in warm-blooded animals and fish include lice, biting lice, ticks, nasal bots, keds, biting flies, muscoid flies, flies, myiasitic fly larvae, chiggers, gnats, mosquitoes and fleas.

The compounds of the invention are especially useful for combating the following parasites: *Cimex lectularius, Rhipicephalus sanguineus*, and *Ctenocephalides felis.*

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in furbearing animals such as mink, chinchilla and raccoon, birds such as hens, geese, turkeys and ducks and fish such as fresh- and salt-water fish such as trout, carp and eels. Particularly preferred are domestic animals, such as dogs or cats.

The compounds I may be applied in total amounts of 0.5 mg/kg to 100 mg/kg per day, preferably 1 mg/kg to 50 mg/kg per day.

For oral administration to warm-blooded animals, the compounds I may be formulated as animal feeds, animal feed premixes, animal feed concentrates, pills, solutions, pastes, suspensions, drenches, gels, tablets, boluses and capsules. For oral administration, the dosage form chosen should provide the animal with 0.01 mg/kg to 100 mg/kg of animal body weight per day of the compounds I, preferably with 0.5 mg/kg to 100 mg/kg of animal body weight per day.

Alternatively, the compounds I may be administered to animals parenterally, e.g., by intraruminal, intramuscular, intravenous or subcutaneous injection. The compounds I may be dispersed or dissolved in a physiologically acceptable carrier for subcutaneous injection. Alternatively, the compounds I may be formulated into an implant for subcutaneous administration. In addition, the compounds I may be transdermally administered to animals. For parenteral administration, the dosage form chosen should provide the animal with 0.01 mg/kg to 100 mg/kg of animal body weight per day of the compounds I.

The compounds I may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compounds I. In addition, the compounds I may be formulated as ear tags for animals, particularly quadrupeds e.g. cattle and sheep.

Oral solutions are administered directly.

Solutions for use on the skin are trickled on, spread on, rubbed in, sprinkled on or sprayed on.

Gels are applied to or spread on the skin or introduced into body cavities.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures.

Emulsions can be administered orally, dermally or as injections.

Suspensions can be administered orally or topically/dermally.

Semi-solid preparations can be administered orally or topically/dermally.

For the production of solid preparations, the active compound is mixed with suitable excipients, if appropriate with addition of auxiliaries, and brought into the desired form.

The compositions which can be used in the invention can comprise generally from about 0.001 to 95% of the compound I.

Ready-to-use preparations contain the compounds acting against parasites, preferably ectoparasites, in concentrations of 10 ppm to 80% by weight, preferably from 0.1 to 65% by weight, more preferably from 1 to 50% by weight, most preferably from 5 to 40% by weight.

Preparations which are diluted before use contain the compounds acting against ectoparasites in concentrations of 0.5 to 90% by weight, preferably of 1 to 50% by weight.

Furthermore, the preparations comprise the compounds of formula I against endoparasites in concentrations of 10 ppm to 2% by weight, preferably of 0.05 to 0.9% by weight, very particularly preferably of 0.005 to 0.25% by weight.

Solid formulations which release compounds of the invention may be applied in total amounts of 10 mg/kg to 300 mg/kg, preferably 20 mg/kg to 200 mg/kg, most preferably 25 mg/kg to 160 mg/kg body weight of the treated animal in the course of three weeks.

A. PREPARATION EXAMPLES

With appropriate modification of the starting materials, the procedures given in the synthesis description were used to obtain further compounds I. The compounds obtained in this manner are listed in the table that follows, together with physical data.

The products shown below were characterized by melting point determination, by NMR spectroscopy or by the masses ([m/z]) or retention time (RT; [min.]) determined by HPLC-MS or HPLC spectrometry.

HPLC-MS=high performance liquid chromatography-coupled mass spectrometry;

HPLC method A: Shimadzu LC2010, Column: Waters XBridge C18,150 mm×4.6 mm ID×5μ; Mobile Phase: A: water+0,1% TFA; B: acetonitrile+0,1% TFA; Temperature: 40° C.; Gradient: 10% B to 100% B in 5 min; 100% B 2 min; 10% B 3 min; Flow: 1.4 ml/min; Run Time: 10 min; PDA detector.

Example 1: 2-chloro-N-(2,4-difluorophenyl)-5-[[5-(trifluoromethyl)-5-[3-(trifluoromethyl)phenyl]-4H-isoxazol-3-yl]amino]benzamide [I-38]

Step 1: To a solution of i-PrMgCl (99 mL, 0.20 mol) in THF (600 mL) at 0° C. was added n-BuLi (87.3 mL, 0.22 mol), followed by the dropwise addition of 1-bromo-3-(trifluoromethyl)benzene (45 g, 0.20 mol) in THF (50 mL), and the resulting mixture was stirred at 0° C. for 30 min, after which HPLC analysis showed the reaction was completed. 2,2,2-trifluoro-N-methoxy-N-methyl-acetamide (94.5 g, 0.60 mol) was added dropwise at 0° C., the reaction was allowed to warm to ambient temperature (20-25° C.; RT) and stirred at that temperature for 3 h. The reaction mixture was poured into $NH_4Cl$ solution (sat. aq., 600 mL), the aqueous phase was extracted with EtOAc (3×400 mL), and the combined organic extracts were washed with NaCl solution (sat. aq., 1×400 mL), dried over $Na_2SO_4$, filtered and concentrated to give 2,2,2-trifluoro-1-[3-(trifluoromethyl)phenyl]ethanone (37 g, yield 77%) as a yellow oil which could be directly used in next step without further purification.

Step 2: To a solution of 2,2,2-trifluoro-1-[3-(trifluoromethyl)phenyl]ethanone (37.0 g, 0.153 mol) in THF (400 mL) at 20-25° C. was added 2-diethoxyphosphorylacetonitrile (26.6 g, 0.153 mol), LiBr (13.3 g, 0.153 mol), and $Et_3N$(31.0 g, 0.306 mol), before the resulting reaction mixture was heated to 70° C. and stirred at that temperature for 16 h. Then the reaction mixture was allowed to cool to 20-25° C., filtered, and the filtrate was extracted with EtOAc (3×300 mL). The combined organic extracts were washed with NaCl solution (sat. aq., 1×200 mL), dried over $Na_2SO_4$, filtered and concentrated. The residue was purified by column chromatography (petroleum ether/EtOAc=5:1) to give (Z)-4,4,4-trifluoro-3-[3-(trifluoromethyl)phenyl]but-2-enenitrile (30 g, 75%) as a colorless oil.

$^1$H-NMR (400 MHz, $CDCl_3$, RT): δ 7.82 (br d, J=7.9 Hz, 1H) 7.77 (s, 1H) 7.67-7.74 (m, 1H) 7.59-7.66 (m, 1H) 5.91-6.42 (m, 1H).

Step 3: To a solution of (Z)-4,4,4-trifluoro-3-[3-(trifluoromethyl)phenyl]but-2-enenitrile (30 g, 0.11 mol) in MeOH (300 mL) was added hydroxyurea (12.0 g, 0.159 mol) and NaOMe (10.7 g, 0.204 mol) in portions at 25° C., and the resulting mixture was then heated to 80° C. and stirred at that temperature for 16 h. Then the reaction mixture was poured into $H_2O$ (100 mL), the aqueous phase was extracted with EtOAc (3×100 mL), and the combined organic extracts were washed with NaCl solution (sat. aq., 100 mL), dried over $Na_2SO_4$, filtered, and concentrated. Purification by column chromatography (petroleum ether/EtOAc=5:1) afforded 5-(trifluoromethyl)-5-[3-(trifluoromethyl)phenyl]-4H-isoxazol-3-amine (16 g, 48%) as a white solid.

$^1$H-NMR (400 MHz, DMSO-$d_6$, RT): δ 7.82 (br d, J=7.9 Hz, 1H) 7.77 (s, 1H) 7.67-7.74 (m, 1H) 7.59-7.66 (m, 1H) 5.91-6.42 (m, 1H).

Step 4: To a solution of 5-(trifluoromethyl)-5-[3-(trifluoromethyl)phenyl]-4H-isoxazol-3-amine (5.00 g, 16.8 mmol) in 1,4-dioxane (50 mL) at 20-25° C. was added $Pd_2(dba)_3$ (1.54 g, 1.68 mmol, CAS-No 51364-51-3), Xantphos (1.45 g, 2.51 mmol, CAS-No 161265-03-8), $Cs_2CO_3$ (8.21 g, 25.2 mmol) and tert-butyl 5-bromo-2-chloro-benzoate (5.38 g, 18.5 mmol), before the reaction mixture was heated to 80° C. and stirred at that temperature for 16 h. The reaction mixture was poured into water (50 mL), extracted with EtOAc (3×40 mL), and the combined organic extracts were washed with NaCl solution (40 mL), dried over $Na_2SO_4$, filtered, and concentrated. Purification by column chromatography (petroleum ether/EtOAc=3:1) afforded tert-butyl 2-chloro-5-[[5-(trifluoromethyl)-5-[3-(trifluoromethyl)phenyl]-4H-isoxazol-3-yl]amino]benzoate (7.0 g, 88%) as a brown solid.

$^1$H-NMR (400 MHz, DMSO-$d_6$, RT): δ 7.79 (br d, J=7.9 Hz, 1H), 7.82 (s, 1H), 7.70 (d, J=7.8 Hz, 1H), 7.53-7.62 (m, 3H), 7.34 (d, J=8.5 Hz, 1H), 3.93 (d, J=16.1 Hz, 1H), 3.58 (d, J=16.1 Hz, 1H), 1.61 (s, 9H).

Step 5: To a solution of tert-butyl 2-chloro-5-[[5-(trifluoromethyl)-5-[3-(trifluoromethyl)phenyl]-4H-isoxazol-3-yl]amino]benzoate (7.0 g, 13.3 mmol) in a mixture of MeCN (80 mL) and $H_2O$ (1.0 mL) at 20-25° C. was added $I_2$ (3.37 g, 13.3 mmol), before the reaction was heated to 80° C. and stirred at that temperature for 16 h. The reaction mixture was poured into $H_2O$ (100 mL), the pH adjusted to 3 with HCl solution (2.0 N in $H_2O$), the aqueous phase was extracted with EtOAc (3×80 mL), and the combined organic extracts were washed with NaCl solution (sat. aq., 80 mL), dried over $Na_2SO_4$, filtered and concentrated to give 2-chloro-5-[[5-(trifluoromethyl)-5-[3-(trifluoromethyl)phenyl]-4H-isoxazol-3-yl]amino]benzoic acid (4.0 g, 64%) as a brown solid.

$^1$H-NMR (400 MHz, DMSO-$d_6$, RT): δ 10.3 (s, 1H) 9.58 (s, 1H) 7.83-7.97 (m, 3H) 7.69-7.80 (m, 2H) 7.47 (s, 2H) 7.63 (s, 1H) 3.79-4.18 (m, 2H).

Step 6: To a solution of 2-chloro-5-[[5-(trifluoromethyl)-5-[3-(trifluoromethyl)phenyl]-4H-isoxazol-3-yl]amino]benzoic acid (1.0 g, 2.2 mmol) in DMF (10 mL) at 20-25° C. was added HATU (1.26 g, 3.31 mmol, CAS-No 148893-10-1) and $Et_3N$(672 mg, 6.63 mmol), and 2,4-difluoroaniline (200 mg, 2.43 mmol), and the reaction mixture was stirred at that temperature for 16 h. The mixture was poured into $H_2O$ (10 mL), the aqueous phase was extracted with EtOAc (3×20 mL), and the combined organic extracts were washed with NaCl solution (sat. aq., 2×10 mL), dried over $Na_2SO_4$, filtered and concentrated. Purification by column chromatography (petroleum ether/EtOAc=75:25) afforded the title compound 2-chloro-N-(2,4-difluorophenyl)-5-[[5-(trifluoromethyl)-5-[3-(trifluoromethyl)phenyl]-4H-isoxazol-3-yl]amino]benzamide [I-38] (200 mg, 16%) as a yellow solid.

$^1$H NMR (400 MHz, $CDCl_3$, RT): δ 10.3 (s, 1H) 9.59 (s, 1H) 7.85-7.98 (m, 3H) 7.70-7.82 (m, 2H) 7.64 (s, 1H) 7.48 (s, 2H) 7.32-7.41 (m, 1H) 7.14 (br t, J=7.8 Hz, 1H) 3.78-4.16 (m, 2H).

Example 2: N-(1-cyanocyclopropyl)-3-[[5-(3,5-dichlorophenyl)-5-(trifluoromethyl)-4H-isoxazol-3-yl]amino]-2,6-difluoro-benzamide [I-30]

Step 1: To a suspension of Mg(0) turnings (27.7 g, 1.15 mol) in THF (300 mL) at 20-25° C. was added a solution of 1-bromo-3,5-dichloro-benzene (250 g, 0.960 mol) in THF (1.0 L) dropwise, before the solution was heated to 70° C. and stirred at that temperature for 1 h. Then the reaction mixture was cooled to 0° C., and 2,2,2-trifluoro-N-methoxy-N-methyl-acetamide was added dropwise into the reaction at 0° C. and the mixture was stirred at that temperature for 1 h. The resulting solution was quenched with $NH_4Cl$ solution (sat. aq., 1.2 L), the aqueous phase was extracted with EtOAc (3×500 mL), and the combined organic extracts were washed with NaCl solution (sat. aq., 2×1.2 L), filtered, and concentrated. Purification by distillation at 110° C. with reduced pressure afforded 1-(3,5-dichlorophenyl)-2,2,2-trifluoro-ethanone (300 g, 64%) as a faintly yellowish oil.

$^1$H-NMR (400 MHz, $CDCl_3$, RT): δ=7.92 (d, J=1.0 Hz, 2H), 7.70 (t, J=1.9 Hz, 1H).

Step 2: To a solution of 1-(3,5-dichlorophenyl)-2,2,2-trifluoro-ethanone (25 g, 0.11 mol) and $Ph_3PMeBr$ (1.3 g, 12 mmol) in THF (400 mL) at 20-25° C. was added t-BuOK solution (1.0 M in THF, 123 mL, 0.139 mol) dropwise, and the mixture was stirred at that temperature for 2 h. Then the mixture was quenched with $H_2O$ (1.0 L), the aqueous phase was extracted with EtOAc (3×300 mL), and the combined organic extracts were washed with NaCl solution (sat. aq., 1×1.0 L), dried over $Na_2SO_4$, filtered, and concentrated. Purification by column chromatography (petroleum ether [PE]) afforded 1,3-dichloro-5-[1-(trifluoromethyl)vinyl]benzene (70 g, 73%) as a yellow oil.

$^1$H-NMR (400 MHz, $CDCl_3$, RT): δ 7.41-7.39 (m, 1H), 7.36-7.34 (m, 2H), 6.07-6.03 (m, 1H), 5.84-5.81 (m, 1H).

Step 3: To a solution of 1,3-dichloro-5-[1-(trifluoromethyl)vinyl]benzene (22.0 g, 92.8 mmol) in EtOAc (220 mL) at 20-25° C. was added 1,1-dibromoformaldoxime (22.5 g, 113 mmol), and $NaHCO_3$ (78.1 g, 0.928 mol), before the mixture was heated to 50° C. and stirred at that temperature for 12 h. The reaction mixture was quenched with $H_2O$ (300 mL), extracted with EtOAc (3×100 mL), and the combined organic extracts were washed with NaCl solution (sat. aq., 300 mL), dried over $Na_2SO_4$, filtered, and concentrated. Purification by trituration (petroleum ether) afforded 3-bromo-5-(3,5-dichlorophenyl)-5-(trifluoromethyl)-4H-isoxazole (64 g, 63%) as a white solid.

$^1$H-NMR (400 MHz, $CDCl_3$, RT): δ=7.48-7.44 (m, 1H), 7.44-7.38 (m, 2H), 3.92 (d, J=17.8 Hz, 1H), 3.57 (dd, J=0.6, 17.8 Hz, 1H).

Step 4: To a solution of 3-bromo-5-(3,5-dichlorophenyl)-5-(trifluoromethyl)-4H-isoxazole (0.50 g, 1.38 mmol) in 2,4-dimethylpentan-3-ol (5.0 mL) at 20-25° C. was added methyl 3-amino-2,6-difluoro-benzoate (0.257 g, 1.38 mmol), and TsOH (0.183 g, 0.964 mmol), before the mixture was heated to 130° C. and stirred at that temperature for 16 h. Then LCMS showed ca. 30% of the desired compound, and the reaction mixture was quenched with $H_2O$ (100 mL), the aqueous phase was extracted with EtOAc (3×30 mL), and the combined organic extracts were washed with NaCl solution (sat. aq., 100 mL), dried over $Na_2SO_4$, filtered, and concentrated. The residue was purified by trituration (petroleum ether) to give methyl 3-[[5-(3,5-dichlorophenyl)-5-(trifluoromethyl)-4H-isoxazol-3-yl]amino]-2,6-difluoro-benzoate (0.24 g, 38%) as a yellow solid.

$^1$H-NMR (400 MHz, $CDCl_3$, RT): δ 8.21 (dt, J=5.4, 9.4 Hz, 1H), 7.48 (s, 2H), 7.46-7.42 (m, 1H), 6.98 (dt, J=1.8, 9.2 Hz, 1H), 6.11 (br s, 1H), 3.94 (s, 1H), 3.59 (d, J=16.0 Hz, 1H), 1.56 (s, 3H).

Step 5: To the solution of methyl 3-[[5-(3,5-dichlorophenyl)-5-(trifluoromethyl)-4H-isoxazol-3-yl]amino]-2,6-difluoro-benzoate (1.10 g, 2.34 mmol) in THF (220 mL) at 20-25° C. was added $LiOH{\cdot}H_2O$ (0.148 g, 3.52 mmol), before the mixture was heated to 70° C. and stirred at that temperature for 5 days. The reaction mixture was quenched with $H_2O$ (200 mL), the aqueous phase was adjusted to pH=5 with aq. HCl, and then extracted with EtOAc (3×60 mL). The combined organic extracts were washed with NaCl solution (200 mL), dried over $Na_2SO_4$, filtered and concentrated. The residue was purified by Prep-HPLC ($NH_4HCO_3$) to give 3-[[5-(3,5-dichlorophenyl)-5-(trifluoromethyl)-4H-isoxazol-3-yl]amino]-2,6-difluoro-benzoic acid (0.65 g, 61%) as a white solid.

$^1$H NMR (400 MHz, $CDCl_3$, RT): δ 7.47 (s, 1H), 7.38 (s, 2H), 4.68 (br s, 2H), 3.48 (d, J=17.2 Hz, 1H), 3.19 (br d, J=17.2 Hz, 1H), 1.26 (s, 1H).

Step 6: To a solution of 3-[[5-(3,5-dichlorophenyl)-5-(trifluoromethyl)-4H-isoxazol-3-yl]amino]-2,6-difluoro-benzoic acid (0.30 g, 0.66 mmol) in MeCN (4.0 mL) at 20-25° C. was added 1-aminocyclopropanecarbonitrile (93.5 mg, 0.793 mmol), N,N,N',N'-tetramethylchloroformamidinium hexafluorophosphate ("TCFH") (0.278 g, 0.991 mmol), and N-methylimidazole ("NMI") (0.217 g, 2.64 mmol), and the reaction mixture was stirred at that temperature for 16 h. The reaction mixture was quenched with $H_2O$ (10 mL), filtered and the filtrate was extracted with EtOAc (3×3.0 mL). The combined organic extracts were washed with NaCl solution (10 mL), dried over $Na_2SO_4$, filtered and concentrated. Purification by column chromatography (petroleum ether/EtOAc=100:0 to 65:35; gradient) afforded the title compound N-(1-cyanocyclopropyl)-3-[[5-(3,5-dichlorophenyl)-5-(trifluoromethyl)-4H-isoxazol-3-yl]amino]-2,6-difluoro-benzamide [I-30](0.116 g, 34%) as a white solid.

$^1$H-NMR (400 MHz, methanol-$d_4$, RT): δ 8.12 (dt, J=5.7, 9.3 Hz, 1H), 7.56 (s, 3H), 7.04 (dt, J=1.7, 9.0 Hz, 1H), 4.86 (s, 47H), 3.98 (d, J=17.0 Hz, 1H), 3.71 (d, J=17.0 Hz, 1H), 1.63-1.57 (m, 2H), 1.34-1.31 (m, 2H).

Example 3: 3-[[5-(3,5-dichlorophenyl)-5-(trifluoromethyl)-4H-isoxazol-3-yl]amino]-N-(2,4-difluorophenyl)-2-fluoro-benzamide [I-48]

Step 1: To a solution of 3-bromo-5-(3,5-dichlorophenyl)-5-(trifluoromethyl)-4H-isoxazole (0.50 g, 1.38 mmol, synthesized as described in example 2; steps 1-3) in 2,4-dimethylpentan-3-ol (5.0 mL) at 20-25° C. was added 3-bromo-2-fluoro-aniline (0.178 g, 1.38 mmol), and TsOH (0.183 g, 0.964 mmol), before the reaction was heated to 120° C. and stirred at that temperature for 48 h. Then LCMS analysis showed ca. 20% desired product, and the reaction mixture was quenched with $H_2O$ (100 mL), filtered and the filtrate extracted with EtOAc (3×30 mL). The combined organic extracts were washed with NaCl solution (sat. aq., 100 mL), dried over $Na_2SO_4$, filtered, and concentrated. Purification by column chromatography (petroleum ether/EtOAc=100:0 to 90:10; gradient) afforded N-(3-bromo-2-fluoro-phenyl)-5-(3,5-dichlorophenyl)-5-(trifluoromethyl)-4H-isoxazol-3-amine (78 mg, 12%) as a white solid.

$^1$H-NMR (400 MHz, $CDCl_3$, RT): δ 8.04 (dt, J=1.3, 8.0 Hz, 1H), 7.54-7.48 (m, 2H), 7.47-7.40 (m, 1H), 7.23-7.13 (m, 1H), 7.09-7.00 (m, 1H), 6.19 (br s, 1H), 4.03-3.92 (m, 1H), 3.60 (br d, J=16.1 Hz, 1H).

Step 2: To a solution of N-(3-bromo-2-fluoro-phenyl)-5-(3,5-dichlorophenyl)-5-(trifluoromethyl)-4H-isoxazol-3-amine (500 mg, 1.06 mmol) in toluene (5.0 mL) was added potassium vinyltrifluoroborate (212 mg, 1.59 mmol), t-$Bu_3$P—Pd-G2 (54 mg, 0.11 mmol, CAS-No 1375325-71-5), and $K_2CO_3$ solution (0.525 mL, 2M in $H_2O$), before the reaction was heated to 80° C. and stirred at that temperature for 12 h. The mixture was quenched with $H_2O$ (20 mL), filtered and the filtrate was extracted with EtOAc (3×10 mL). The combined organic extracts were washed with NaCl solution (sat. aq., 1×20 mL), dried over $Na_2SO_4$, filtered, and concentrated. Purification by column chromatography (petroleum ether/EtOAc=100:0 to 95:5; gradient) afforded 5-(3,5-dichlorophenyl)-N-(2-fluoro-3-vinyl-phenyl)-5-(trifluoromethyl)-4H-isoxazol-3-amine (286 mg, 65%) as a white solid.

$^1H$ NMR (400 MHz, $CDCl_3$, RT): δ 7.94 (br t, J=7.1 Hz, 1H), 7.50 (s, 2H), 7.45-7.41 (m, 1H), 7.18-7.08 (m, 2H), 6.85 (dd, J=11.2, 17.7 Hz, 1H), 6.18 (br s, 1H), 5.83 (dd, J=0.8, 17.7 Hz, 1H), 5.42 (dd, J=0.8, 11.2 Hz, 1H), 3.97 (d, J=16.1 Hz, 1H), 3.59 (br d, J=16.1 Hz, 1H).

Step 3: To a solution of 5-(3,5-dichlorophenyl)-N-(2-fluoro-3-vinyl-phenyl)-5-(trifluoromethyl)-4H-isoxazol-3-amine (3.0 g, 7.2 mmol) in a mixture of THF (20 mL) and $H_2O$ (10 mL) at 0° C. was added N-methylmorpholin-N-oxid (2.01 g, 17.2 mmol), $NaIO_4$ (1.50 g, 7.02 mmol), and $K_2OsO_4$ (21 mg, 0.006 mmol), and the resulting reaction mixture was stirred at 0-2° C. for 16 h. Then the mixture was quenched with $H_2O$ (30 mL), filtered and the filtrate was extracted with EtOAc (3×10 mL). The combined organic extracts were washed with NaCl solution (sat. aq., 1×30 mL), dried over $Na_2SO_4$, filtered and concentrated to give 3-[[5-(3,5-dichlorophenyl)-5-(trifluoromethyl)-4H-isoxazol-3-yl]amino]-2-fluoro-benzaldehyde (3.0 g, crude) as a yellow solid which was used in the next step without further purification.

$^1H$ NMR (400 MHz, $CDCl_3$, RT) δ=10.3 (s, 1H), 8.37 (br t, J=8.1 Hz, 1H), 7.54-7.45 (m, 4H), 7.46-7.40 (m, 1H), 6.36 (br s, 1H), 4.05-3.97 (m, 1H), 3.64 (br d, J=16.3 Hz, 1H).

Step 4: To a solution of 3-[[5-(3,5-dichlorophenyl)-5-(trifluoromethyl)-4H-isoxazol-3-yl]amino]-2-fluoro-benzaldehyde (0.50 g, 1.2 mmol) in a mixture of 1,4-dioxane (3.6 mL) and $H_2O$ (1.2 mL) at 20-25° C. was added $NaClO_2$ (0.214 g, 2.4 mmol), and $NH_3SO_3$ (46 mg, 4.8 mmol), and the reaction mixture was stirred at that temperature for 40 min. The mixture was quenched with $H_2O$ (10 mL), filtered, and the filtrate was extracted with EtOAc (3×3 mL). The combined organic extracts were washed with NaCl solution (sat. aq., 1×10 mL), dried over $Na_2SO_4$, filtered and concentrated. Purification by Prep-HPLC (TFA) afforded 3-[[5-(3,5-dichlorophenyl)-5-(trifluoromethyl)-4H-isoxazol-3-yl]amino]-2-fluoro-benzoic acid (1.33 g, 52%) as a yellow solid.

$^1H$ NMR (400 MHz, DMSO-$d_6$, RT) δ=9.18 (d, J=1.8 Hz, 1H), 8.13 (dt, J=1.5, 7.9 Hz, 1H), 7.78 (t, J=1.8 Hz, 1H), 7.60 (d, J=1.6 Hz, 2H), 7.46-7.36 (m, 1H), 7.23 (t, J=8.0 Hz, 1H), 4.08-3.97 (m, 1H), 3.93-3.85 (m, 1H).

Step 5: To a solution of 3-[[5-(3,5-dichlorophenyl)-5-(trifluoromethyl)-4H-isoxazol-3-yl]amino]-2-fluoro-benzoic acid (0.33 g, 0.757 mmol) in MeCN (4.0 mL) at 20-25° C. was added 2,4-difluoroaniline (0.145 g, 1.135 mmol), TCFH (0.212 g, 1.14 mmol), and NMI (0.249 g, 3.03 mmol), and the reaction was stirred at that temperature for 16 h. The mixture was quenched with $H_2O$ (10 mL), filtered and the filtrate was extracted with EtOAc (3×3 mL). The combined organic extracts were washed with NaCl solution (sat. aq., 1×10 mL), dried over $Na_2SO_4$, filtered, and concentrated. Purification by Prep-HPLC ($NH_4HCO_3$) afforded the 3-[[5-(3,5-dichlorophenyl)-5-(trifluoromethyl)-4H-isoxazol-3-yl]amino]-N-(2,4-difluorophenyl)-2-fluoro-benzamide [I-48] (53 mg, 13%) as a yellow solid.

$^1H$-NMR (400 MHz, $CDCl_3$, RT): δ 8.45 (dt, J=6.0, 9.1 Hz, 1H), 8.36-8.29 (m, 1H), 7.78-7.67 (m, 1H), 7.51 (d, J=1.6 Hz, 2H), 7.48-7.43 (m, 1H), 7.39-7.30 (m, 1H), 6.99-6.88 (m, 2H), 6.30-6.23 (m, 1H), 3.99 (d, J=16.1 Hz, 1H), 3.62 (d, J=16.0 Hz, 1H).

Example 4: Synthesis of 2-chloro-5-[[5-(3,5-dichloro-4-fluoro-phenyl)-5-(trifluoromethyl)-4H-isoxazol-3-yl]amino]-N-[(4R)-3-oxo-2-(2,2,2-trifluoroethyl)isoxazolidin-4-yl]benzamide [I-114]

Synthesis of [(4R)-3-oxo-2-(2,2,2-trifluoroethyl)isoxazolidin-4-yl]ammonium chloride Step 1: To a solution of (4R)-4-aminoisoxazolidin-3-one (5.00 g, 49.0 mmol) in THF (75 mL) and water (50 mL) at 20-25° C. was added triethylamine (5.20 g, 51.4 mmol). The reaction mixture was cooled to 10° C. and a solution of di-tert-butyl carbonate (11.2 g, 51.4 mmol) in THF (25 mL) was added dropwise. The resulting mixture was stirred for 18 h at 20-25° C. Then, THF was removed under reduced pressure. The residue was treated with HCl solution (2.0 N in $H_2O$) until pH 2-3 was reached and stirred for 45 min. The resulting precipitate was filtered off, washed with $H_2O$ (2×20 mL) and cyclohexane (2×10 mL), and dried under reduced pressure at 40° C. to give tert-butyl N-[(4R)-3-oxoisoxazolidin-4-yl]carbamate (5.32 g, 52%) as a white solid.

HPLC-MS (method A): retention time=0.659 min, m/z=285 ($[M+H]^+$).

Step 2: To a solution of tert-butyl N-[(4R)-3-oxoisoxazolidin-4-yl]carbamate (2.00 g, 9.89 mmol) in THF (30 mL) at 20-25° C. was added triethylamine (3.00 g, 29.7 mmol). The reaction mixture was cooled to 0° C. and 2,2,2-trifluoroethyl-trifluoromethanesulfonate (2.98 g, 12.9 mmol) was added. The resulting mixture was stirred for 96 h at 20-25° C. The reaction was quenched into $H_2O$ (20 ml), the aqueous phase was extracted with EtOAc (3×10 mL), and the combined organic extracts were washed with $H_2O$ (2×20 ml), dried over $Na_2SO_4$, filtered and concentrated under reduced pressure. The crude residue was dissolved in MTBE (20 mL). The precipitate was filtered off and dried under reduced pressure at 30° C. to give tert-butyl N-[(4R)-3-oxo-2-(2,2,2-trifluoroethyl)isoxazolidin-4-yl]carbamate (1.32 g, 47%) as a white solid.

HPLC-MS (method A): retention time=0.948 min, m/z=229 ($[M+H]^+$).

Step 3: To a solution of tert-butyl N-[(4R)-3-oxo-2-(2,2,2-trifluoroethyl)isoxazolidin-4-yl]carbamate (1.32 g, 4.64 mmol) in dichloromethane (10 mL) at 0° C. was added HCl (4M in 1,4-dioxane, 4.64 mL, 18.6 mmol) dropwise. The reaction mixture was stirred at 20-25° C. for 19 h, and then concentrated under reduced pressure. The residue was re-dissolved in dichloromethane and concentrated under reduced pressure. The residue was re-dissolved in dichloromethane (3 mL), the precipitate was filtered off and dried under reduced pressure at 40° C. to give the title [(4R)-3-oxo-2-(2,2,2-trifluoroethyl)isoxazolidin-4-yl]ammonium chloride (906 mg, 88%).

$^1H$-NMR (400 MHz, DMSO-$d_6$, RT) δ 4.70 (d, J=8.7 Hz, 1H), 4.61 (t, J=8.7 Hz, 1H), 4.49 (q, J=9.1 Hz, 2H), 4.34 (t, J=9.0 Hz, 1H).

Synthesis of 2-chloro-5-[[5-(3,5-dichloro-4-fluoro-phenyl)-5-(trifluoromethyl)-4H-isoxazol-3-yl]amino]benzoic acid Step 1: To a solution of 5-(3,5-dichloro-4-fluoro-phenyl)-5-(trifluoromethyl)-4H-isoxazol-3-amine (1.5 g, 4.7 mmol, synthesized analogously as described above) and methyl 5-bromo-2-chloro-benzoate (1.18 g, 4.73 mmol) in 1,4-dioxane (50 mL) at 20-25° C. was added tris(dibenzylideneacetone)dipalladium(0) (216 mg, 0.23 mmol), 4,5-bis (diphenylphosphino)-9,9-dimethylxanthene (328 mg, 0.57 mmol) and $Cs_2CO_3$ (4.62 g, 14.2 mmol). The resulting mixture was heated to 80° C. and stirred at that temperature for 5 h. After cooling to 20-25° C., the reaction mixture was diluted with EtOAc (50 mL) and washed with ammonium chloride solution (sat. aq., 1×45 mL) and NaCl solution (sat. aq., 1×45 mL). The organic phase was dried over $Na_2SO_4$, filtered, and concentrated under reduced pressure. Purification by column chromatography ($SiO_2$, cyclohexane/EtOAc=100:0 to 65:35) afforded methyl 2-chloro-5-[[5-(3,5-dichloro-4-fluoro-phenyl)-5-(trifluoromethyl)-4H-isoxazol-3-yl]amino]benzoate (1.12 g, 48%).

HPLC-MS (method A): retention time=1.392 min, m/z=485 ($[M+H]^+$); $^1$H-NMR (400 MHz, $CDCl_3$, RT) δ 7.82 (d, J=2.8 Hz, 1H), 7.57-7.45 (m, 3H), 7.36 (d, J=8.8 Hz, 1H), 6.28 (s, 1H), 3.92 (s, 3H), 3.89 (d, J=16.2 Hz, 1H), 3.49 (d, J=16.1 Hz, 1H).

Step 2: To a solution of methyl 2-chloro-5-[[5-(3,5-dichloro-4-fluoro-phenyl)-5-(trifluoromethyl)-4H-isoxazol-3-yl]amino]benzoate (1.12 g, 2.31 mmol) in THF (5.0 mL) and MeOH (5.0 mL) at 20-25° C. was added a solution of LiOH (968 mg, 23.1 mmol) in $H_2O$ (5 mL) dropwise. After 4 h, HPLC-MS analysis showed that the reaction was completed. The reaction mixture was treated with HCl solution (2.0 N in $H_2O$) until pH 1 was reached. The resulting mixture was extracted with EtOAc (3×5.0 mL). The organic phase was washed with NaCl solution (sat. aq., 25 mL), dried over $Na_2SO_4$, filtered, and concentrated under reduced pressure to give 2-chloro-5-[[5-(3,5-dichloro-4-fluoro-phenyl)-5-(trifluoromethyl)-4H-isoxazol-3-yl]amino]-benzoic acid (1.10 g, quant.). The crude product was used in the next step without further purification.

HPLC-MS (method A): retention time=1.261 min, m/z=472 ($[M+H]^+$); $^1$H-NMR (400 MHz, DMSO-$d_6$, RT) δ 7.92 (d, J=2.6 Hz, 1H), 7.84 (d, J=6.3 Hz, 2H), 7.54-7.42 (m, 2H), 3.97 (d, J=17.1 Hz, 1H), 3.86 (d, J=17.2 Hz, 1H).

Synthesis of 2-chloro-5-[[5-(3,5-dichloro-4-fluoro-phenyl-5-(trifluoromethyl)-4H-isoxazol-3-yl]amino]-N-[(4R)-3-oxo-2-(2,2,2-trifluoroethyl)isoxazolidin-4-yl]benzamide [I-114]

Step 1: To a solution of the above 2-chloro-5-[[5-(3,5-dichloro-4-fluoro-phenyl)-5-(trifluoromethyl)-4H-isoxazol-3-yl]amino]-benzoic acid (100 mg, 0.21 mmol) and [(4R)-3-oxo-2-(2,2,2-trifluoroethyl)isoxazolidin-4-yl]ammonium chloride (56 mg, 0.21 mmol) in $CH_2Cl_2$ (8.0 mL) at 20-25° C. was added 2,4,6-tripropyl-1,3,5,2λ5,4λ5,6λ5-trioxatriphosphinane 2,4,6-trioxide (50% in EtOAc, 809 mg, 1.27 mmol), $iPr_2NEt$ (82 mg, 0.64 mmol) and 4-dimethylaminopyridine (26 mg, 0.21 mmol), and the resulting reaction mixture was stirred at that temperature for 3 h. Then, $CH_2Cl_2$ (5.0 mL) was added and the reaction mixture was washed with $H_2O$ (10 mL). The organic phase was separated, dried over $Na_2SO_4$, and evaporated under reduced pressure. Purification by column chromatography ($SiO_2$, cyclohexane/EtOAc=100:0 to 30:70) afforded the title 2-chloro-5-[[5-(3,5-dichloro-4-fluoro-phenyl-5-(trifluoromethyl)-4H-isoxazol-3-yl]amino]-N-[(4R)-3-oxo-2-(2,2,2-trifluoroethyl)isoxazolidin-4-yl]benzamide [I-114] (70 mg, 52%) as a white wax.

HPLC-MS (method A): retention time=1.303 min, m/z=637 ($[M+H]^+$); $^1$H-NMR (500 MHz, $CDCl_3$, RT) δ 7.62-7.56 (m, 1H), 7.43 (dd, J=6.6, 2.9 Hz, 2H), 7.25 (t, J=2.7 Hz, 1H), 7.17 (d, J=8.8 Hz, 1H), 5.02 (p, J=7.7, 6.5 Hz, 1H), 4.81 (t, J=8.6 Hz, 1H), 4.34 (t, J=10.5 Hz, 1H), 4.24 (dt, J=16.3, 8.1 Hz, 1H), 4.13 (dt, J=15.8, 8.1 Hz, 1H), 3.85 (d, J=16.5 Hz, 1H), 3.49 (d, J=16.5 Hz, 1H).

Example 5: Synthesis of 2-chloro-5-[[5-(3,5-dichloro-4-fluoro-phenyl)-5-(trifluoromethyl)-4H-isox-azol-3-yl]-methyl-amino]-N-[(4R)-2-ethyl-3-oxo-isoxazolidin-4-yl]benzamide [I-119]

Step 1: To a solution of methyl 2-chloro-5-[[5-(3,5-dichloro-4-fluoro-phenyl)-5-(trifluoromethyl)-4H-isoxazol-3-yl]amino]benzoate (200 mg, 0.41 mmol, prepared as described above) in acetonitrile (5.0 mL) at 20-25° C. was added $K_2CO_3$ (114 mg, 0.82 mmol) followed by iodomethane (88 mg, 0.62 mmol). The reaction mixture was stirred for 5 d at 20-25° C. Then HPLC-MS analysis showed that the reaction was completed. The reaction mixture was quenched with $H_2O$ (20 mL) and extracted with EtOAc (3×5 mL). The organic phase was dried over $Na_2SO_4$, filtered, and concentrated under reduced pressure. Purification by column chromatography ($SiO_2$, cyclohexane/EtOAc=100:0 to 50:50) afforded methyl 2-chloro-5-[[5-(3,5-dichloro-4-fluoro-phenyl)-5-(trifluoromethyl)-4H-isoxazol-3-yl]-methyl-amino]benzoate (100 mg, 49%) as an oil.

HPLC-MS (method A): retention time=1.426 min, m/z=500 ($[M+H]^+$); $^1$H-NMR (400 MHz, $CDCl_3$, RT) δ 7.62 (d, J=2.7 Hz, 1H), 7.52-7.46 (m, 3H), 7.24 (dd, J=8.6, 2.8 Hz, 1H), 3.95 (s, 3H), 3.65 (d, J=16.5 Hz, 1H), 3.30 (s, 3H), 3.20 (d, J=16.5 Hz, 1H).

Step 2: To a solution of methyl 2-chloro-5-[[5-(3,5-dichloro-4-fluoro-phenyl)-5-(trifluoromethyl)-4H-isoxazol-3-yl]-methyl-amino]benzoate (191 mg, 0.38 mmol) in THF (2.0 mL) and MeOH (2.0 mL) at 20-25° C. was added a solution of LiOH—$H_2O$ (160 mg, 3.80 mmol) in $H_2O$ (2.0 mL) dropwise. After 4 h, HPLC-MS analysis showed that the reaction was completed. The reaction mixture was treated with HCl solution (2.0 N in $H_2O$) until pH 1 was reached and concentrated under reduced pressure. The residue was dissolved in $H_2O$ (10 mL), the aqueous phase was extracted with EtOAc (2×5 mL), and the combined organic extracts were washed with $H_2O$ (5 mL) and NaCl solution (sat. aq., 5 mL), dried over $Na_2SO_4$, filtered and concentrated under reduced pressure to afford 2-chloro-5-[[5-(3,5-dichloro-4-fluoro-phenyl)-5-(trifluoromethyl)-4H-isoxazol-3-yl]-methyl-amino]benzoic acid (130 mg, 70%).

HPLC-MS (method A): retention time=1.267 min, m/z=485 ($[M+H]^+$); $^1$H-NMR (500 MHz, methanol-$d_4$, RT) δ 7.71 (d, J=2.5 Hz, 1H), 7.66 (d, J=6.2 Hz, 2H), 7.52 (d, J=8.6 Hz, 1H), 7.41 (dd, J=8.6, 2.6 Hz, 1H), 3.82 (d, J=17.0 Hz, 1H), 3.59 (d, J=17.0 Hz, 1H), 3.28 (s, 3H).

Step 3: To a solution of 2-chloro-5-[[5-(3,5-dichloro-4-fluoro-phenyl)-5-(trifluoromethyl)-4H-isoxazol-3-yl]-methyl-amino]benzoic acid (40 mg, 0.08 mmol) and (4R)-4-amino-2-ethyl-isoxazolidin-3-one hydrochloride (16 mg, 0.1 mmol) in $CH_2Cl_2$ (8.0 mL) at 20-25° C. was added 2,4,6-tripropyl-1,3,5,2λ5,4λ5,6λ5-trioxatriphosphinane 2,4,6-trioxide (50% in EtOAc, 414 mg, 0.49 mmol), followed by $iPr_2NEt$ (32 mg, 0.25 mmol) and 4-dimethylaminopyridine (10 mg, 0.08 mmol). The resulting reaction mixture was stirred at 20-25° C. for 2 h. Then, $CH_2Cl_2$ (5 ml) was added and the reaction mixture was washed with $H_2O$ (10 ml). The organic phase was dried over $Na_2SO_4$ and evaporated under reduced pressure. Purification by column chromatography ($SiO_2$, cyclohexane/EtOAc=100:0 to 0:100) afforded 2-chloro-5-[[5-(3,5-dichloro-4-fluoro-phenyl)-5-(trifluoromethyl)-4H-isoxazol-3-yl]-methyl-amino]-N-[(4R)-2-ethyl-3-oxo-isoxazolidin-4-yl]benzamide [I-119](34 mg, 69%).

HPLC-MS (method A): retention time=1.268 min, m/z=597 ($[M+H]^+$); $^1$H-NMR (500 MHz, $CDCl_3$, RT) δ 7.52 (t, J=2.6 Hz, 1H), 7.49 (d, J=5.9 Hz, 2H), 7.45 (d, J=8.6 Hz, 1H), 7.19 (dd, J=8.6, 2.7 Hz, 1H), 4.96 (t, J=8.3 Hz, 1H), 4.88 (dddd, J=10.3, 8.0, 4.3, 2.0 Hz, 1H), 4.07 (dd, J=10.6, 8.6 Hz, 1H), 3.74-3.60 (m, 2H), 3.29 (s, 3H), 3.18 (dd, J=16.5, 3.3 Hz, 1H), 1.27 (t, J=7.1 Hz, 3H).

Example 6: Synthesis of 2-chloro-N-(1-cyano-1-methyl-ethyl)-5-[[5-(3,5-dichloro-4-fluoro-phenyl)-5-(trifluoromethyl)-4H-isoxazol-3-yl]amino]benzamide [I-58]

Step 1: To a solution of 2-chloro-5-[[5-(3,5-dichloro-4-fluoro-phenyl)-5-(trifluoromethyl)-4H-isoxazol-3-yl]amino]benzoic acid (100 mg, 0.21 mmol, prepared as described above) and 2-amino-2-methyl-propanenitrile (22 mg, 0.25 mmol) in $CH_2Cl_2$ (8.0 mL) at 20-25° C. was added 2,4,6-tripropyl-1,3,5,2λ5,4λ5,6λ5-trioxatriphosphinane 2,4,6-trioxide (50% in EtOAc, 810 mg, 1.27 mmol), followed by 4-dimethylaminopyridine (78 mg, 0.64 mmol). The reaction mixture was heated to 100° C. in a microwave for 45 min. Then HPLC-MS analysis showed that the reaction was completed. The reaction mixture was allowed to cool to 20-25° C., filtered and the filtrate was concentrated under reduced pressure. The crude product was purified by column chromatography ($SiO_2$, cyclohexane/EtOAc=100:0 to 0:100, gradient) afforded 2-chloro-N-(1-cyano-1-methyl-ethyl)-5-[[5-(3,5-dichloro-4-fluoro-phenyl)-5-(trifluoromethyl)-4H-isoxazol-3-yl]amino]benzamide [I-58] (53 mg, 46%).

HPLC-MS (method A): retention time=1.295 min, m/z=538 ($[M+H]^+$); $^1$H-NMR (400 MHz, methanol-$d_4$, RT) δ 7.71 (d, J=6.2 Hz, 2H), 7.55 (d, J=2.5 Hz, 1H), 7.44 (dd, J=8.8, 2.7 Hz, 1H), 7.36 (d, J=8.8 Hz, 1H), 3.95 (d, J=16.8 Hz, 1H), 3.70 (d, J=16.8 Hz, 1H), 2.15 (s, 3H), 1.75 (s, 3H).

Example 7: Synthesis 2-chloro-5-[[5-(3,5-dichloro-4-fluoro-phenyl)-5-(trifluoromethyl)-4H-isoxazol-3-yl]amino]-N-(4-fluoro-3-pyridyl)benzamide [I-62]

Step 1: To a solution of 2-chloro-5-[[5-(3,5-dichloro-4-fluoro-phenyl)-5-(trifluoromethyl)-4H-isoxazol-3-yl]amino]benzoic acid (100 mg, 0.21 mmol, prepared as described above) and (4-fluoro-3-pyridyl)ammonium chloride (38 mg, 0.25 mmol) in $CH_2Cl_2$ (6.0 mL) at 20-25° C. was added 2,4,6-tripropyl-1,3,5,2λ5,4λ5,6λ5-trioxatriphosphinane 2,4,6-trioxide (50% in EtOAc, 810 mg, 1.27 mmol), followed by $iPr_2NEt$ (82 mg, 0.64 mmol) and 4-dimethylaminopyridine (78 mg, 0.64 mmol). The reaction mixture was heated to 40° C. in a microwave for 30 min. Then HPLC-MS analysis showed that the reaction was completed. The reaction mixture was diluted with EtOAc (10 mL) and washed with $H_2O$ (3×5 mL). The organic phase was dried over $Na_2SO_4$, filtered, and concentrated under reduced pressure. The crude product was purified by column chromatography (RP, $MeCN/H_2O$=0:100 to 100:0, gradient) afforded 2-chloro-5-[[5-(3,5-dichloro-4-fluorophenyl)-5-(trifluoromethyl)-4H-isoxazol-3-yl]amino]-N-(4-fluoro-3-pyridyl)benzamide [I-62](16 mg, 13%).

HPLC-MS (method A): retention time=1.205 min, m/z=566.9 ($[M+H]^+$); $^1$H-NMR (400 MHz, methanol-$d_4$, RT) δ 9.13 (d, J=9.4 Hz, 1H), 8.46-8.38 (m, 1H), 7.74-7.67 (m, 3H), 7.50 (dd, J=8.8, 2.7 Hz, 1H), 7.45-7.32 (m, 2H), 3.97 (d, J=16.8 Hz, 1H), 3.72 (d, J=16.8 Hz, 1H).

Example 8: Synthesis of 2-chloro-5-[[5-(3,5-dichloro-4-fluoro-phenyl)-5-(trifluoromethyl)-4H-isoxazol-3-yl]amino]-N-[1-(difluoromethylsulfonyl)azetidin-3-yl]benzamide [I-41]

Step 1: To a solution of tert-butyl N-(azetidin-3-yl)carbamate (1.00 g, 5.81 mmol) and $iPr_2NEt$ (1.88 g, 14.5 mmol) in $CH_2Cl_2$ (10 mL) at 0° C. under an atmosphere of argon was added a solution of difluoromethanesulfonyl chloride (1.75 g, 11.6 mmol) in $CH_2Cl_2$ (5.0 mL) dropwise, and the resulting mixture was stirred at that temperature for 1 h. Then the reaction mixture was warmed up to 20-25° C., stirred at that temperature for 1 h, and then quenched with water (20 mL). The organic phase was separated, dried over $Na_2SO_4$, filtered, and concentrated under reduced pressure. Purification by column chromatography ($NH_2$—Column, cyclohexane/EtOAc=100:0 to 50:50, gradient) afforded tert-butyl N-[1-(difluoromethylsulfonyl)azetidin-3-yl]carbamate (386 mg, 23%).

HPLC-MS (method A): retention time=0.889 min, m/z=256 ($[M+H]^+$); $^1$H-NMR (400 MHz, $CDCl_3$, RT) δ 4.97 (s, 1H), 4.58 (s, 1H), 4.39 (t, J=8.1 Hz, 2H), 4.15-4.07 (m, 2H), 1.45 (s, 9H).

Step 2: [1-(difluoromethylsulfonyl)azetidin-3-yl]ammonium chloride: tert-butyl N-[1-(difluoromethylsulfonyl)azetidin-3-yl]carbamate (386 mg, 1.35 mmol) was dissolved in HCl solution (4 N in 1,4-dioxane, 15 mL) and stirred at 20-25° C. for 17 h. The reaction mixture was concentrated under reduced pressure, the residue re-dissolved in $CH_2Cl_2$ and concentrated under reduced pressure (3×) to give [1-(difluoromethylsulfonyl)azetidin-3-yl]ammonium chloride (367 mg, quant.). The crude product was used in the next step without further purification.

$^1$H-NMR (400 MHz, methanol-$d_4$, RT) δ 4.46 (t, J=7.8 Hz, 2H), 4.25-4.18 (m, 2H).

Step 3: To a solution of 2-chloro-5-[[5-(3,5-dichloro-4-fluoro-phenyl)-5-(trifluoromethyl)-4H-isoxazol-3-yl]amino]benzoic acid (100 mg, 0.21 mmol, prepared as described in the examples above) and [1-(difluoromethylsulfonyl)azetidin-3-yl]ammonium chloride (59 mg, 0.27 mmol) in $CH_2Cl_2$ (6.0 mL) at 20-25° C. was added bromo(tripyrrolidin-1-yl)phosphonium hexafluorophosphate (124 mg, 0.27 mmol) and $iPr_2NEt$ (110 mg, 0.85 mmol). The resulting reaction mixture was stirred at that temperature for 17 h, and then concentrated under reduced pressure. Purification by column chromatography (RP, $MeCN/H_2O$=0:100 to 100:0, gradient) afforded 2-chloro-5-[[5-(3,5-dichloro-4-fluoro-phenyl)-5-(trifluoromethyl)-4H-isoxazol-3-yl]amino]-N-[1-(difluoromethylsulfonyl)azetidin-3-yl]benzamide [I-41] as a beige solid (69 mg, 43%).

HPLC-MS (method A): retention time=1.304 min, m/z=641 ($[M+H]^+$); $^1$H-NMR (500 MHz, methanol-$d_4$, RT) δ 7.69 (d, J=6.1 Hz, 2H), 7.59 (d, J=2.7 Hz, 1H), 7.40 (dd, J=8.8, 2.7 Hz, 1H), 7.35 (d, J=8.8 Hz, 1H), 4.45 (t, J=8.1 Hz, 2H), 4.28-4.22 (m, 2H), 3.95 (d, J=16.7 Hz, 1H), 3.70 (d, J=16.8 Hz, 1H).

Example 9: Synthesis of 2-chloro-5-[[5-(3,5-dichloro-4-fluoro-phenyl)-5-(trifluoromethyl)-4H-isoxazol-3-yl]amino]-N-[1-(trifluoromethylsulfonyl)azetidin-3-yl]benzamide [I-77]

Step 1: To a solution of tert-butyl N-(azetidin-3-yl)carbamate (500 mg, 2.90 mmol) and $iPr_2NEt$ (938 mg, 7.26 mmol) in $CH_2Cl_2$ (10 mL) at 0° C. under an atmosphere of argon was added a solution of trifluoromethanesulfonyl chloride (979 mg, 5.81 mmol) in $CH_2Cl_2$ (5.0 mL) dropwise, and the resulting mixture was stirred at that temperature for 1 h. Then the reaction mixture was warmed to 20-25° C., stirred at that temperature for 1.5 h, and then quenched with $H_2O$ (10 mL). The organic phase was separated, dried over $Na_2SO_4$, filtered and concentrated under reduced pressure to give tert-butyl N-[1-(trifluoromethylsulfonyl)azetidin-3-yl] carbamate (806 mg, 91%) as a white solid.

$^1$H-NMR (400 MHz, $CDCl_3$, RT): δ 5.09 (s, 1H), 4.60 (s, 1H), 4.42 (t, J=8.1 Hz, 2H), 4.17-4.09 (m, 2H), 1.45 (s, 9H).

Step 2: tert-butyl N-[1-(trifluoromethylsulfonyl)azetidin-3-yl]carbamate (806 mg, 2.65 mmol) was dissolved in HCl (4N in 1,4-dioxane, 20 mL) and stirred at 20-25° C. overnight. The resulting precipitate was filtered off, washed with 1,4-dioxane and dried under reduced pressure to afford [1-(trifluoromethylsulfonyl)azetidin-3-yl]ammonium chloride (483 mg, 76%) as a withe solid.

$^1$H-NMR (400 MHz, DMSO-$d_6$, RT): δ 8.87 (s, 3H), 4.46-4.31 (m, 4H), 4.27-4.16 (m, 1H).

Step 3: To a solution of 2-chloro-5-[[5-(3,5-dichloro-4-fluoro-phenyl)-5-(trifluoromethyl)-4H-isoxazol-3-yl] amino]benzoic acid (50 mg, 0.11 mmol) and [1-(trifluoromethylsulfonyl)azetidin-3-yl]ammonium chloride (51 mg, 0.21 mmol) in $CH_2Cl_2$ (6.0 mL) at 20-25° C. was added 2,4,6-tripropyl-1,3,5,2λ5,4λ5,6λ5-trioxatriphosphinane 2,4,6-trioxide (405 mg, 0.64 mmol) followed by $iPr_2NEt$ (55 mg, 0.42 mmol) and 4-dimethylaminopyridine (13 mg, 0.11 mmol). The resulting reaction mixture was stirred for 2 h at 20-25° C. Then $CH_2Cl_2$ (5.0 ml) was added and the reaction mixture was washed with water (10 mL). The organic phase was dried over $Na_2SO_4$ and concentrated under reduced pressure. Purification by column chromatography ($SiO_2$, cyclohexane/EtOAc=100:0 to 60:40, gradient) afforded 2-chloro-5-[[5-(3,5-dichloro-4-fluoro-phenyl)-5-(trifluoromethyl)-4H-isoxazol-3-yl]amino]-N-[1-(trifluoromethylsulfonyl)azetidin-3-yl]benzamide [I-77] (34 mg, 49%) as a beige wax.

HPLC-MS (method A): retention time=1.365 min, m/z=658 ($[M+H]^+$); $^1$H-NMR (400 MHz, $CDCl_3$, RT) δ 7.52-7.44 (m, 2H), 7.37-7.28 (m, 2H), 7.15 (d, J=8.9 Hz, 1H), 4.85-4.74 (m, 1H), 4.47 (t, J=8.3 Hz, 2H), 4.33 (dd, J=10.4, 3.9 Hz, 2H), 3.84 (d, J=16.5 Hz, 1H), 3.49 (d, J=16.5 Hz, 1H), 1.91 (s, 1H), 1.43 (s, 1H).

Example 10: Synthesis of 2-chloro-N-(1-cyanocyclopropyl)-5-[cyclopropylmethyl-[5-(3,5-dichlorophenyl)-5-(trifluoromethyl)-4H-isoxazol-3-yl]amino] benzamide [I-60]

Step 1: To a solution of 1-(3,5-dichlorophenyl)-2,2,2-trifluoro-ethanone (30.0 g, 0.123 mol) in THF (400 mL) at 20-25° C. was added 2-diethoxyphosphorylacetonitrile (21.7 g, 0.125 mmol), $Et_3N$(34.8 g, 246 mmol) and LiBr (10.8 g, 0.123 mol), before the resulting reaction mixture was heated to 70° C. and stirred at that temperature for 16 h. The reaction mixture was poured into $H_2O$ (300 mL), the aqueous phase was extracted with EtOAc (3×150 mL), and the combined organic extracts were washed with NaCl solution (2×150 mL), dried over $Na_2SO_4$, filtered, and concentrated. Purification by column chromatography (petroleum ether/EtOAc=10:1) afforded (Z)-3-(3,5-dichlorophenyl)-4,4,4-trifluoro-but-2-enenitrile (29.0 g, 88%) as a brown oil.

$^1$H-NMR (400 MHz, $CDCl_3$, RT): δ 7.49-7.55 (m, 1H), 7.40 (d, J=1.4 Hz, 1H), 7.33 (s, 1H), 5.96-6.31 (m, 1H).

Step 2: To a solution of (Z)-3-(3,5-dichlorophenyl)-4,4,4-trifluoro-but-2-enenitrile (29.0 g, 0.104 mol) in MeOH (300 mL) at 20-25° C. was added NaOMe (8.16 g, 0.155 mol) and hydroxyurea (8.61 g, 0.114 mol), before the reaction was heated to 80° C. and stirred at that temperature for 16 h. Then the mixture was poured into $H_2O$ (100 mL), the aqueous phase was extracted with EtOAc (3×100 mL), and the combined organic extracts were washed with NaCl solution (sat. aq., 100 mL), dried over $Na_2SO_4$, filtered, and concentrated to give 5-(3,5-dichlorophenyl)-5-(trifluoromethyl)-4H-isoxazol-3-amine (22 g, 70%) as white solid.

$^1$H-NMR (400 MHz, $CDCl_3$, RT): δ 7.45 (s, 2H), 7.40-7.43 (m, 1H), 4.07 (br s, 2H), 3.68-3.74 (m, 1H), 3.34 (d, J=16.4 Hz, 1H).

Step 3: To a solution of 5-(3,5-dichlorophenyl)-5-(trifluoromethyl)-4H-isoxazol-3-amine (10.0 g, 33.4 mmol) in 1,4-dioxane (100 mL) at 20-25° C. was added $Pd_2(dba)_3$ (3.06 g, 3.34 mmol, CAS-No 51364-51-3), Xantphos (2.90 g, 5.02 mmol, CAS-No 161265-03-8), $Cs_2CO_3$ (16.4 g, 50.2 mmol) and tert-butyl 5-bromo-2-chloro-benzoate (10.7 g, 36.7 mmol), before the reaction was heated to 80° C. and stirred at that temperature for 16 h. The mixture was poured into $H_2O$ (80 mL), extracted with EtOAc (3×100 mL), and the combined organic extracts were washed with NaCl solution (sat. aq., 80 mL), dried over $Na_2SO_4$, filtered, and concentrated. Purification by column chromatography (petroleum ether/EtOAc=3:1) afforded tert-butyl 2-chloro-5-[[5-(3,5-dichlorophenyl)-5-(trifluoromethyl)-4H-isoxazol-3-yl] amino]benzoate (12.0 g, 71%) as a brown solid.

$^1$H-NMR (400 MHz, DMSO-$d_6$, RT): δ 9.61 (s, 1H), 7.76 (d, J=2.43 Hz, 2H), 7.65 (s, 2H), 7.44-7.48 (m, 2H), 3.74-3.98 (m, 2H), 1.54 (s, 9H).

Step 4: To a solution of tert-butyl 2-chloro-5-[[5-(3,5-dichlorophenyl)-5-(trifluoromethyl)-4H-isoxazol-3-yl] amino]benzoate (1.00 g, 1.96 mmol) in DMF (10 mL) at 0° C. was added NaH (0.157 g, 3.92 mmol) in portions, and the mixture was stirred at that temperature for 0.5 h. Bromomethylcyclopropane (0.397 g, 2.94 mmol) was added, the reaction was allowed to warm to 20-25° C. and was stirred at that temperature for 16 h. The mixture was poured into $H_2O$ (10 mL), the aqueous phase was extracted with EtOAc (3×10 mL), and the combined organic extracts were washed NaCl solution (sat. aq., 1×20 mL), dried over $Na_2SO_4$, filtered, and concentrated. Purification by column chromatography (petroleum ether/EtOAc=1:1) and Prep-HPLC afforded tert-butyl 2-chloro-5-[cyclopropylmethyl-[5-(3,5-dichlorophenyl)-5-(trifluoromethyl)-4H-isoxazol-3-yl] amino]-benzoate (700 mg, 59%) as a brown solid.

$^1$H-NMR (400 MHz, $CDCl_3$, RT): δ 7.44-7.56 (m, 2H), 7.39 (s, 3H), 7.16-7.26 (m, 1H), 3.75 (ddd, J=6.62, 4.17, 2.51 Hz, 1H), 3.47-3.55 (m, 2H), 3.08-3.18 (m, 1H), 1.62 (s, 9H), 1.01-1.13 (m, 1H), 0.47 (d, J=7.91 Hz, 2H), −0.01-0.21 (m, 2H).

Step 5: To a solution of tert-butyl 2-chloro-5-[cyclopropylmethyl-[5-(3,5-dichlorophenyl)-5-(trifluoromethyl)-4H-isoxazol-3-yl]amino]-benzoate (700 mg, 1.25 mmol) in MeCN (8.0 mL) and $H_2O$ (1.0 mL) at 20-25° C. was added $I_2$ (316 mg, 1.25 mmol), before the reaction mixture was heated to 80° C. and stirred at that temperature for 16 h. The mixture was poured into $H_2O$ (10 mL), the pH of the aqueous phase was adjusted to 3 with HCl (2.0 N in $H_2O$) and extracted with EtOAc (3×20 mL). The combined organic phases were washed with NaCl solution (sat. aq., 1×10 mL), dried over $Na_2SO_4$, filtered, and concentrated to give 2-chloro-5-[cyclopropylmethyl-[5-(3,5-dichlorophenyl)-5-(trifluoromethyl)-4H-isoxazol-3-yl]amino]benzoic acid (0.30 g, 47%) as a brown solid.

$^1$H-NMR (400 MHz, DMSO-$d_6$, RT) δ 7.64-7.68 (m, 1H), 7.39-7.59 (m, 3H), 7.12-7.21 (m, 1H), 6.96-7.03 (m, 1H), 3.44-3.64 (m, 4H), 0.43-0.59 (m, 1H), 0.30 (br d, J=8.00 Hz, 2H), 0.00 (br s, 2H).

Step 6: To the solution of 2-chloro-5-[cyclopropylmethyl-[5-(3,5-dichlorophenyl)-5-(trifluoromethyl)-4H-isoxazol-3-yl]amino]benzoic acid (300 mg, 0.592 mmol) in MeCN (5.0 mL) at 20-25° C. was added NMI (195 mg, 4.70 mmol), TCFH (301 mg, 0.892 mmol), and 1-aminocyclopropanecarbonitrile (134 mg, 2.10 mmol), and the resulting reaction mixture was stirred at that temperature for 18 h. The reaction mixture was quenched into $H_2O$ (10 mL), the aqueous phase was extracted with EtOAc (2×20 mL), and the combined organic extracts were washed with NaCl solution (40 mL, sat. aq.), dried over $Na_2SO_4$, filtered, and concentrated. Purification by column chromatography (petroleum ether/EtOAc=1:1) afforded the title 2-chloro-N-(1-cyanocyclopropyl)-5-[cyclopropylmethyl-[5-(3,5-dichlorophenyl)-5-(trifluoromethyl)-4H-isoxazol-3-yl]amino]benzamide [I-60] (220 mg, 65%) as a white solid.

$^1$H-NMR (400 MHz, DMSO-$d_6$, RT): δ 9.34 (s, 1H), 7.70-7.83 (m, 1H), 7.51-7.61 (m, 3H), 7.41-7.48 (m, 2H), 3.51 (d, J=6.88 Hz, 2H), 1.54-1.60 (m, 2H), 1.23-1.32 (m, 2H), 0.91-1.04 (m, 1H), 0.32-0.43 (m, 2H), 0.02-0.13 (m, 2H).

Example 11: Synthesis of 2-chloro-5-[[5-(3,5-dichloro-4-fluoro-phenyl)-5-(trifluoromethyl)-4H-isoxazol-3-yl]amino]-N-(1-oxothietan-3-yl)benzamide [I-61]

Step 1: To a solution of 2-chloro-5-[[5-(3,5-dichloro-4-fluoro-phenyl)-5-(trifluoromethyl)-4H-isoxazol-3-yl]amino]-N-(thietan-3-yl)benzamide (161 mg, 0.3 mmol; synthesized analogously as described in the examples above) in $CH_2Cl_2$ (10 mL) at −78° C. was added 3-chloroperoxybenzoic acid (66 mg, 0.3 mmol). The cooling bath was removed, and the resulting mixture was allowed to warm to −20° C. over 30 min. The reaction mixture was quenched with $Na_2S_2O_3$ solution (sat. aq., 2.0 mL) and $NaHCO_3$ solution (sat. aq., 10 mL), the aqueous phase was extracted with EtOAc (2×15 ml), and the combined organic extracts were dried over $Na_2SO_4$, filtered, and concentrated. The crude residue was recrystallized from $CH_2Cl_2$ to give 2-chloro-5-[[5-(3,5-dichloro-4-fluoro-phenyl)-5-(trifluoromethyl)-4H-isoxazol-3-yl]amino]-N-(1-oxothietan-3-yl)benzamide [I-61](102 mg, 62%) as a white solid.

HPLC-MS (method A): retention time=1.090 min, m/z=519 ([M+H]$^+$); $^1$H-NMR (400 MHz, methanol-d4, RT) δ 7.70 (d, J=6.2 Hz, 2H), 7.60 (d, J=2.5 Hz, 1H), 7.42-7.35 (m, 2H), 4.56 (tt, J=10.2, 7.5 Hz, 1H), 4.22 (ddt, J=11.7, 7.4, 2.6 Hz, 2H), 3.95 (d, J=16.8 Hz, 1H), 3.82-3.66 (m, 2H), 3.35 (d, J=3.1 Hz, 1H).

Example 12: Synthesis of N-(3-amino-2,4-difluoro-phenyl)-2-chloro-5-[[5-(3,5-dichlorophenyl)-5-(trifluoromethyl)-4H-isoxazol-3-yl]amino]benzamide [I-4]

Step 1: To a solution of 2-chloro-5-[[5-(3,5-dichlorophenyl)-5-(trifluoromethyl)-4H-isoxazol-3-yl]amino]benzoic acid (18.0 g, 39.6 mmol, prepared analogously as described in the above examples) and tert-butyl N-(3-amino-2,6-difluoro-phenyl)-N-tert-butoxycarbonyl-carbamate (12.0 g, 34.8 mmol, prepared as described in WO2016/168059) in MeCN (100 mL) was added TFCH (14.7 g, 52.3 mmol) and NMI (3.79 g, 69.8 mmol), and the resulting reaction mixture was stirred at 50° C. for 16 h. The mixture was poured into $H_2O$ (200 mL), the aqueous phase was extracted with EtOAc (2×20 mL), and the combined organic extracts were washed with $H_2O$ (3×20 mL) and NaCl solution (sat. aq., 2×20 mL), dried over $Na_2SO_4$, filtered, and concentrated. The residue was purified by column chromatography (petroleum ether/EtOAc=3:1) to give tert-butyl N-tertbutoxycarbonyl-N-[3-[[2-chloro-5-[[5-(3,5-dichlorophenyl)-5-(trifluoromethyl)-4H-isoxazol-3-yl]amino]benzoyl]amino]-2,6-difluoro-phenyl]carbamate (12.5 g, 46%).

$^1$H-NMR (400 MHz, DMSO-$d_6$, RT): δ 10.4 (1H, s), 9.58 (1H, s), 7.75-7.62 (1H, m), 7.62 (3H, m), 7.44 (2H, s), 7.25-7.20 (1H, s), 6.73-6.67 (1H, t, J=8.8 Hz) 3.93 (2H, q, J=17.2, 27.2 Hz) 1.37 (18H, m).

Step 2: To a solution of tert-butyl N-tert-butoxycarbonyl-N-[3-[[2-chloro-5-[[5-(3,5-dichlorophenyl)-5-(trifluoromethyl)-4H-isoxazol-3-yl]amino]benzoyl]amino]-2,6-difluoro-phenyl]carbamate (24 g, 31 mmol) in EtOAc (50 mL) was added EtOAc/HCl (300 mL), and the reaction was stirred at 20-25° C. for 3 h. The mixture was filtered, and the filtrate was concentrated. The residue was recrystallized from MTBE (10 mL) to give N-(3-amino-2,4-difluoro-phenyl)-2-chloro-5-[[5-(3,5-dichlorophenyl)-5-(trifluoromethyl)-4H-isoxazol-3-yl]amino]benzamide [I-4] (13.0 g, 73%).

$^1$H-NMR (400 MHz, DMSO-$d_6$, RT): δ 10.1 (1H, s), 9.51 (1H, s), 7.79-7.65 (2H, m), 7.61 (3H, m), 7.40 (1H, s), 6.92-6.87 (1H, m), 6.87-6.75 (1H, m), 5.30 (2H, s), 3.99-3.33 (2H, m).

Example 13: Synthesis of 2-chloro-5-[[5-(3,5-dichlorophenyl)-5-(trifluoromethyl)-4H-isoxazol-3-yl]amino]-N-[3-[(2,2-difluoroacetyl)amino]-2,4-difluoro-phenyl]benzamide [I-6]

Step 1: To a solution of N-(3-amino-2,4-difluoro-phenyl)-2-chloro-5-[[5-(3,5-dichlorophenyl)-5-(trifluoromethyl)-4H-isoxazol-3-yl]amino]benzamide (700 mg, 1.20 mmol, prepared as described above) and 2,2-difluoroacetic acid (190 mg, 1.98 mmol) in MeCN (10 mL) was added NMI (380 mg, 4.63 mmol) and TFCH(556 mg, 1.98 mmol), the resulting reaction was heated to 80° C. and stirred at that temperature for 16 hours. The mixture was poured into $H_2O$ (20 mL), the aqueous phase was extracted with EtOAc (2×20 mL), and the combined organic extracts were washed with $H_2O$ (3×20 mL) and NaCl solution (sat. aq., 1×20 mL), dried over $Na_2SO_4$, filtered, and concentrated. The residue was purified by column chromatography (petroleum ether/EtOAc=3:1) and Prep-HPLC to give 2-chloro-5-[[5-(3,5-dichlorophenyl)-5-(trifluoromethyl)-4H-isoxazol-3-yl]amino]-N-[3-[(2,2-difluoroacetyl)amino]-2,4-difluoro-phenyl]benzamide [I-6](90 mg, 23%).

$^1$H-NMR (400 MHz, DMSO-$d_6$, RT) δ10.8 (1H, s), 10.45 (1H, s), 9.63 (1H, s), 7.79-7.78 (1H, s), 7.71-7.69 (1H, s), 7.65 (3H, m), 7.48-7.48 (2H, m), 7.27-7.24 (1H, s), 6.68-6.41 (1H, m), 3.99-3.86 (2H, m).

Example 14: Synthesis of 2-chloro-5-[[5-(3,5-dichlorophenyl)-5-(trifluoromethyl)-4H-isoxazol-3-yl]-methyl-amino]-N-[1-(1-methylpyrazol-4-yl)cyclopropyl]benzamide [I-125]

Step 1: To a solution of 5-(3,5-dichlorophenyl)-5-(trifluoromethyl)-4H-isoxazol-3-amine (8.00 g, 26.8 mmol, synthesized analogously as described in the examples above) and $Et_3N$(11.0 g, 107 mmol) in THF (80 mL) was added $Boc_2O$ (17.6 g, 80.5 mmol) and DMAP (654 mg, 5.36 mmol), and the resulting reaction mixture was stirred at 20° C. for 16 h. The mixture was poured into $H_2O$ (120 mL), extracted with EtOAc (2×30 mL), and the combined organic extracts were washed with NaCl solution (sat. aq., 1×30 mL), dried over $Na_2SO_4$, filtered, and concentrated under reduced pressure. Purification by column chromatography (petroleum ether/EtOAc=3:1) gave tert-butyl N-tert-butoxycarbonyl-N-[5-(3,5-dichlorophenyl)-5-(trifluoromethyl)-4H-isoxazol-3-yl] carbamate (12.7 g, 96%) as white solid.

Step 2: To a solution of tert-butyl N-tert-butoxycarbonyl-N-[5-(3,5-dichlorophenyl)-5-(trifluoromethyl)-4H-isoxazol-3-yl]carbamate (15.0 g, 30.1 mmol) in EtOH (150 mL) at 20-25° C. was added $N_2H_4{\cdot}H_2O$ (3.80 g, 75.3 mmol), and the reaction mixture was stirred at that temperature for 3 h.

The mixture was concentrated, and the residue was poured into $H_2O$ (40 mL), the aqueous phase was extracted with EtOAc (2×15 mL), and the combined organic phases were washed with NaCl solution (sat. aq., 1×30 mL), dried over $Na_2SO_4$, filtered, and concentrated. Purification by column chromatography (petroleum ether/EtOAc=3:1) afforded tert-butyl N-[5-(3,5-dichlorophenyl)-5-(trifluoromethyl)-4H-isoxazol-3-yl]carbamate (9.08 g, 75%).

Step 3: To a solution of tert-butyl N-[5-(3,5-dichlorophenyl)-5-(trifluoromethyl)-4H-isoxazol-3-yl]carbamate (6.00 g, 15.1 mmol) in MeCN (60 mL) was added $K_2CO_3$ (6.30 g, 45.3 mmol) and MeI (4.40 g, 30.1 mmol), before the reaction mixture was heated to 60° C. and stirred at that temperature for 16 h. The mixture was poured into $H_2O$ (100 mL), the aqueous phase was extracted with EtOAc (3×20 mL), and the combined organic phases were washed with NaCl solution (sat. aq., 1×30 mL), dried over $Na_2SO_4$, filtered, and concentrated. Purification by column chromatography (petroleum ether/EtOAc=3:1) afforded tert-butyl N-[5-(3,5-dichlorophenyl)-5-(trifluoromethyl)-4H-isoxazol-3-yl]-N-methyl-carbamate (5.58 g, 94%) as brown solid.

Step 4: To a solution of tert-butyl N-[5-(3,5-dichlorophenyl)-5-(trifluoromethyl)-4H-isoxazol-3-yl]-N-methyl-carbamate (8.55 g, 2.08 mmol) in EtOAc (30 mL) at 0° C. was added HCl solution (4.0M in EtOAc, 200 mL), before the reaction mixture was allowed to warm to 20-25° C. and stirred at that temperature for 16 h. The mixture was concentrated, and the crude product was purified by column chromatography (petroleum ether/EtOAc=3:1) to give 5-(3,5-dichlorophenyl)N-methyl-5-(trifluoromethyl)-4H-isoxazol-3-amine (5.55 g, 85%) as a white solid.

$^1$H-NMR (400 MHz, $CDCl_3$, RT) δ 7.47 (br s, 2H), 7.40 (s, 1H), 3.75 (br s, 1H), 3.36 (br s, 1H), 2.93 (br s, 3H).

Step 5: To a solution of 5-(3,5-dichlorophenyl)-N-methyl-5-(trifluoromethyl)-4H-isoxazol-3-amine (2.00 g, 6.39 mmol) and methyl 5-bromo-2-chloro-benzoate (1.59 g, 6.39 mmol) in 1,4-dioxane (40 mL) under an atmosphere of argon at 20-25° C. was added $Cs_2CO_3$ (6.24 g, 19.2 mmol) followed by 4,6-bis(diphenylphosphino)-9,9-dimethylxanthene (443 mg, 0.77 mmol) and tris(dibenzylideneacetone) dipalladium(0) (292 mg, 0.32 mmol). The reaction mixture was heated to 80° C. and stirred at that temperature overnight. The mixture was cooled to 20-25° C., diluted with EtOAc (50 mL), and the organic phase was washed with $NH_4Cl$ solution (sat. aq., 1×40 mL), NaCl solution (sat. aq., 1×40 mL), dried over $Na_2SO_4$, filtered and concentrated. Purification by column chromatography ($SiO_2$, cyclohexane/EtOAc=100:0 to 65:35) afforded methyl 2-chloro-5-[[5-(3,5-dichlorophenyl)-5-(trifluoromethyl)-4H-isoxazol-3-yl]-methyl-amino]benzoate (3.17 g, quantitative).

HPLC-MS (method A): retention time=1.413 min, m/z=481 ($[M+H]^+$); $^1$H-NMR (400 MHz, $CDCl_3$, RT) δ 7.61 (d, J=2.7 Hz, 1H), 7.48 (d, J=8.6 Hz, 1H), 7.40 (q, J=1.6 Hz, 3H), 7.29-7.19 (m, 1H), 3.95 (s, 3H), 3.63 (d, J=16.5 Hz, 1H), 3.29 (s, 3H), 3.20 (d, J=16.6 Hz, 1H).

Step 6: To a solution of methyl 2-chloro-5-[[5-(3,5-dichlorophenyl)-5-(trifluoromethyl)-4H-isoxazol-3-yl]-methyl-amino]benzoate (3.17 g, 6.58 mmol) in THF (20 mL) and MeOH (20 mL) at 20-25° C. was added a solution of LiOH (2.76 g, 65.81 mmol) in $H_2O$ (10 mL) dropwise. After 4 hours, HPLC-MS analysis showed that the reaction was complete. The reaction mixture was treated with HCl solution (2.0 N in $H_2O$) until pH=1 was reached and concentrated. The residue was dissolved in $H_2O$ (5.0 mL), and the aqueous phase was extracted with ethyl acetate (3×5 mL). The combined organic extracts were washed with $H_2O$ (1×5 mL) and NaCl solution (sat. aq., 1×5 mL), dried over $Na_2SO_4$, filtered and concentrated under reduced pressure to give 2-chloro-5-[[5-(3,5-dichlorophenyl)-5-(trifluoromethyl)-4H-isoxazol-3-yl]-methyl-amino]benzoic acid (2.52 g, 82%) as a yellow solid.

HPLC-MS (method A): retention time=1.266 min, m/z=467 ($[M+H]^+$); $^1$H-NMR (400 MHz, methanol-$d_4$, RT) δ 7.71 (d, J=2.7 Hz, 1H), 7.52 (d, J=8.2 Hz, 4H), 7.40 (dd, J=8.6, 2.8 Hz, 1H), 3.82 (d, J=17.0 Hz, 1H), 3.58 (d, J=17.0 Hz, 1H), 3.28 (s, 3H).

Step 7: To a solution of 2-chloro-5-[[5-(3,5-dichlorophenyl)-5-(trifluoromethyl)-4H-isoxazol-3-yl]-methyl-amino] benzoic acid (100 mg, 0.21 mmol) and 1-(1-methyl-1H-pyrazol-4-yl)cyclopropanamine (35 mg, 0.26 mmol) in $CH_2Cl_2$ (6.0 mL) at 20-25° C. was added 2,4,6-tripropyl-1,3,5,2λ5,4λ5,6λ5-trioxatriphosphinane 2,4,6-trioxide (50% in EtOAc, 816 mg, 1.28 mmol) and DMAP (78 mg, 0.64 mmol), and the resulting reaction mixture was stirred at that temperature for 3 h. Then $CH_2Cl_2$ (5 mL) was added, the organic phase was washed with $H_2O$ (1×10 mL), dried over $Na_2SO_4$, filtered, and concentrated under reduced pressure. Purification by column chromatography ($SiO_2$, cyclohexane/EtOAc=100:0 to 0:100) afforded 2-chloro-5-[[5-(3,5-dichlorophenyl)-5-(trifluoromethyl)-4H-isoxazol-3-yl]-methyl-amino]-N-[1-(1-methylpyrazol-4-yl)cyclopropyl] benzamide [I-125] (96 mg, 77%).

HPLC-MS (method A): retention time=1.260 min, m/z=588 ($[M+H]^+$)

$^1$H-NMR (500 MHz, $CDCl_3$, RT) δ 7.47-7.41 (m, 2H), 7.39 (s, 4H), 7.15 (dd, J=8.6, 2.8 Hz, 1H), 7.06 (s, 1H), 3.83 (s, 3H), 3.64 (d, J=16.6 Hz, 1H), 3.26 (s, 3H), 3.21 (d, J=16.6 Hz, 1H), 2.00 (s, 1H), 1.30-1.24 (m, 2H), 1.21-1.15 (m, 2H).

Example 15: Synthesis of ethyl N-[4-chloro-3-[(1-cyanocyclopropyl)carbamoyl]phenyl]-N-[5-(3,5-dichlorophenyl)-5-(trifluoromethyl)-4H-isoxazol-3-yl]carbamate [I-111] and ethyl N-[4-chloro-3-[(1-cyanocyclopropyl)-ethoxycarbonyl-carbamoyl]-phenyl]-N-[5-(3,5-dichlorophenyl)-5-(trifluoromethyl)-4H-isoxazol-3-yl]carbamate [I-100]

Step 1: To a solution of 2-chloro-N-(1-cyanocyclopropyl)-5-[[5-(3,5-dichlorophenyl)-5-(trifluoromethyl)-4H-isoxazol-3-yl]amino]benzamide (1.00 g, 1.98 mmol, synthesized analogously as described in the examples above) in DMF (10 mL) at 0° C. was added NaH (93.0 mg, 3.88 mmol) in portions, and the reaction mixture was stirred at that temperature for 0.5 h. Ethyl chloroformate (413 mg, 3.88 mmol) was added dropwise at 0° C., before the reaction was allowed to warm to 20-25° C. and stirred at that temperature for 16 h. The mixture was poured into $H_2O$ (10 mL), the aqueous phase was extracted with EtOAc (3×10 mL), and the combined organic extracts were washed with NaCl solution (sat. aq., 1×10 mL), dried over $Na_2SO_4$, filtered, and concentrated under reduced pressure. Separation and purification by column chromatography (petroleum ether/EtOAc=1:1) and preparative HPLC afforded ethyl N-[4-chloro-3-[(1-cyanocyclopropyl)carbamoyl]phenyl]-N-[5-(3,5-dichlorophenyl)-5-(trifluoromethyl)-4H-isoxazol-3-yl]carbamate [I-111](140 mg, 28%) as white solid and ethyl N-[4-chloro-3-[(1-cyanocyclopropyl)-ethoxycarbonyl-carbamoyl]-phenyl]-N-[5-(3,5-dichlorophenyl)-5-(trifluoromethyl)-4H-isoxazol-3-yl]carbamate [I-100](166 mg, 29%).

Ethyl N-[4-chloro-3-[(1-cyanocyclopropyl)carbamoyl]phenyl]-N-[5-(3,5-dichlorophenyl)-5-(trifluoromethyl)-4H-isoxazol-3-yl]carbamate [I-111]

$^1$H-NMR (400 MHz, DMSO-$d_6$, RT) δ 9.51 (s, 1H) 7.80 (t, J=1.88 Hz, 1H) 7.56-7.69 (m, 3H) 7.40-7.55 (m, 2H) 4.50 (d, J=18.51 Hz, 1H) 4.26 (d, J=18.51 Hz, 1H) 4.11-4.18 (m, 2H) 1.50-1.62 (m, 2H) 1.20-1.32 (m, 2H) 1.16 (t, J=7.07 Hz, 3H).

Ethyl N-[4-chloro-3-[(1-cyanocyclopropyl)-ethoxycarbonyl-carbamoyl]-phenyl]-N-[5-(3,5-dichlorophenyl)-5-(trifluoromethyl)-4H-isoxazol-3-yl]carbamate [I-100]

$^1$H-NMR (400 MHz, DMSO-$d_6$, RT) b ppm 7.79 (t, J=1.81 Hz, 1H) 7.63 (d, J=1.50 Hz, 2H) 7.56-7.60 (m, 2H) 7.48-7.52 (m, 1H) 4.47 (d, J=18.51 Hz, 1H) 4.23 (d, J=18.51 Hz, 1H) 4.14 (q, J=7.00 Hz, 2H) 4.05 (q, J=7.21 Hz, 2H) 1.85-1.90 (m, 2H) 1.47-1.58 (m, 2H) 1.14 (t, J=7.07 Hz, 3H) 0.93 (t, J=7.13 Hz, 3H).

Example 16: Synthesis of 2-chloro-5-[[5-[chloro(difluoro)methyl]-5-(3,5-dichlorophenyl)-4H-isoxazol-3-yl]amino]-N-(2,4-difluorophenyl)benzamide [I-131]

Step 1: To a solution 1,3-dichloro-5-iodo-benzene (40.0 g, 0.147 mol) in MTBE (600 mL) at −20° C. was added iPrMgCl·LiCl solution (1.3M in THF, 150 mL, 0.191 mol) dropwise, and the resulting mixture was stirred at that temperature for 2 h. Then, methyl 2-chloro-2,2-difluoro-acetate (32.0 g, 0.220 mol) was added dropwise to the above mixture, the cooling bath was removed, and stirring was continued at 20-25° C. for 16 h. The resulting mixture was poured in $H_2O$ (500 mL), the aqueous phase was extracted with MTBE (2×200 mL), and the combined organic extracts were washed with $H_2O$ (1×300 mL) and NaCl solution (sat. aq., 1×300 mL), dried over $Na_2SO_4$, filtered, and concentrated. Purification by column chromatography ($SiO_2$, petroleum ether/EtOAc=100:1) afforded 2-chloro-1-(3,5-dichlorophenyl)-2,2-difluoro-ethanone (10 g, 26%) as a yellow oil.

$^1$H NMR (400 MHz, $CDCl_3$, RT): δ ppm 7.97 (s, 2H), 7.67-7.71 (m, 1H)

Step 2: To a mixture of 2-chloro-1-(3,5-dichlorophenyl)-2,2-difluoroethanone (10 g, 38.6 mmol) and $Ph_3PMeBr$ (20 g, 57.9 mmol) in THF (200 mL) at 0° C. under an atmosphere of $N_2$ was slowly added t-BuOK (6.4 g, 58 mmol), the cooling bath was removed, and the reaction mixture stirred at 20-25° C. for 16 h. The reaction mixture was poured into $H_2O$ (500 mL), the aqueous phase was extracted with MTBE (2×200 mL), and the combined organic extracts were washed with $H_2O$ (1×300 mL) and NaCl solution (sat. aq., 1×300 mL), dried over $Na_2SO_4$, filtered, and concentrated. Purification by column chromatography ($SiO_2$, petroleum ether/EtOAc=100:1) afforded 1,3-dichloro-5-[1-[chloro(difluoro)methyl]vinyl]benzene (18 g, 61%) as yellow oil.

$^1$H-NMR (400 MHz, $CDCl_3$, RT): δ ppm 7.41 (t, J=1.8 Hz, 1H) 7.36 (d, J=1.8 Hz, 2H) 6.00 (s, 1H) 5.66 (t, J=1.6 Hz, 1H).

Step 3: To a solution of 1,3-dichloro-5-[1-[chloro(difluoro)methyl]vinyl]benzene (5.0 g, 19 mmol) in EtOAc (100 mL) at 20-25° C. under an atmosphere of $N_2$ was added $NaHCO_3$ (2.5 g, 29 mmol) and ethyl 2-chloro-2-hydroxyimino-acetate (4.4 g, 29 mmol) in one portion, before the reaction mixture was heated to 50° C. and the stirred at that temperature for 16 h. The reaction mixture was poured in water (500 mL), the aqueous phase was extracted with MTBE (2×200 mL), and the combined organic extracts were washed with water (300 mL) and NaCl solution (sat. aq., 1×300 mL), dried over $Na_2SO_4$, filtered and concentrated under reduced pressure. Purification by column chromatography ($SiO_2$, petroleum ether/EtOAc=10:1) afforded ethyl 5-[chloro(difluoro)methyl]-5-(3,5-dichlorophenyl)-4H-isoxazole-3-carboxylate (4.07 g, 56%) as yellow solid.

$^1$H-NMR (400 MHz, $CDCl_3$, RT): δ ppm 7.41-7.52 (m, 3H) 4.37 (q, J=7.1 Hz, 2H) 4.01 (d, J=18.5 Hz, 1H) 3.60 (d, J=18.5 Hz, 1H) 1.38 (t, J=7.1 Hz, 3H).

Step 4: To a solution of ethyl 5-[chloro(difluoro)methyl]-5-(3,5-dichlorophenyl)-4H-isoxazole-3-carboxylate (10 g, 22 mol) in THF (150 mL) at 0° C. was added $LiOH \cdot H_2O$ (4.3 g, 107 mmol) in $H_2O$ (40 mL) dropwise, and stirring was continued for 4 h. The resulting mixture was poured into $H_2O$ (30 mL), and the THF was removed under reduced pressure at 35° C. The pH of the residue was adjusted to ca. 2-3 with HCl solution (2.0 N in $H_2O$, 50 mL) at 0° C., the aqueous phase was extracted with EtOAc (2×200 mL), and the combined organic extracts were washed with NaCl solution (sat. aq., 1×50 mL), dried over $Na_2SO_4$, filtered, and concentrated under reduced pressure to give 5-[chloro(difluoro)methyl]-5-(3,5-dichlorophenyl)-4H-isoxazole-3-carboxylic acid (crude) as a yellow solid, which could be used in the next step without further purification.

$^1$H-NMR (400 MHz, DMSO-$d_6$, RT): δ 8.01 (s, 1H) 7.74 (s, 3H) 3.93-4.01 (m, 1H) 3.36 (br d, J=16.9 Hz, 1H).

Step 5: To a solution of 5-[chloro(difluoro)methyl]-5-(3,5-dichlorophenyl)-4H-isoxazole-3-carboxylic acid (3.0 g, 8.1 mmol) in THF (60 mL) at 20-25° C. was added $iPr_2NEt$ (2.25 g, 17.4 mmol), 2,4,6-tripropyl-1,3,5,2λ5,4λ5,6λ5-trioxatriphosphinane 2,4,6-trioxide ("T3P") (7.2 g, 11 mmol), and $(H_3C)_3SiN_3$ (1.3 g, 11 mmol) in one portion, and the reaction mixture was stirred at that temperature for 30 min. Then, t-BuOH (2.5 g, 34.8 mmol) was added and the mixture was heated to 70° C. and stirred at that temperature for 16 h. The resulting mixture was poured into $H_2O$ (500 mL), the aqueous phase was extracted with EtOAc (2×200 mL), and the combined organic extracts were washed with $H_2O$ (1×300 mL) and NaCl solution (sat. aq., 1×300 mL), dried over $Na_2SO_4$, filtered and concentrated to under reduced pressure. Purification by column chromatography ($SiO_2$, petroleum ether/EtOAc=5:1) afforded tert-butyl N-[5-[chloro-(difluoro)methyl]-5-(3,5-dichlorophenyl)-4H-isoxazol-3-yl]carbamate (1.9 g, 56%) as a yellow solid.

$^1$H-NMR (400 MHz, $CDCl_3$, RT): δ 7.48 (s, 2H) 7.41 (s, 1H) 7.11 (br s, 1H) 4.28 (d, J=18.4 Hz, 1H) 3.88 (d, J=18.5 Hz, 1H) 1.50 (s, 9H).

Step 6: To a solution of tert-butyl N-[5-[chloro-(difluoro)methyl]-5-(3,5-dichlorophenyl)-4H-isoxazol-3-yl]carbamate (5.0 g, 12 mmol) in EtOAc (50 mL) at 20-25° C. was added HCl/EtOAc (100 mL) in one portion, and the reaction mixture was stirred at that temperature for 4 h. The reaction mixture was concentrated under reduced pressure and the residue was poured in $NaHCO_3$ solution (sat. aq., 1×50 mL), the aqueous phase was extracted with EtOAc (2×100 mL), and the combined organic extracts were washed with $H_2O$ (300 mL) and NaCl solution (sat. aq., 1×300 mL), dried over $Na_2SO_4$, filtered, and concentrated. The residue was triturated by n-hexane (50 mL), filtered, and the filter cake concentrated to afford 5-[chloro(difluoro)methyl]-5-(3,5-dichlorophenyl)-4H-isoxazol-3-amine (2.5 g, 67%) as a light-yellow solid.

$^1$H-NMR (400 MHz, DMSO-$d_6$, RT): δ 7.74 (s, 1H) 7.58 (s, 2H) 6.00 (s, 2H) 3.61-3.69 (m, 1H) 3.48-3.55 (m, 1H).

This product could then be transformed further into e.g. the compound I-131, analogously to the above examples.

Example 17: Synthesis of tert-Butyl 5-bromo-2-(trifluoromethoxy)benzoate

Step 1: To $(iPr)_2NLi$ solution (2.0M in THF, 24.9 mL) at −60° C. under an atmosphere of $N_2$ was added a solution of 1-bromo-4-(trifluoromethoxy)benzene (10.0 g, 41.5 mmol) in THF (60.0 mL) slowly, and the resulting mixture was stirred at that temperature for 2 h. Then, solid $CO_2$ (18.3 g, 415 mmol) was added, the mixture was allowed to warm to 20-25° C. and stirred at that temperature for 16 h. The solvent was distilled off, the crude product was dissolved in NaOH solution (1.0 N in $H_2O$, 15.0 mL), the aqueous phase was washed with $CH_2Cl_2$ (3×20 mL), and the pH adjusted to ca. 3-4 with HCl solution (4.0M in $H_2O$). The resulting suspension was filtered, the filter cake washed with $H_2O$ (2×5.0 mL), and dried in vacuo to give 5-bromo-2-(trifluoromethoxy)benzoic acid (5.70 g, 48%) as a white solid.

$^1$H-NMR (400 MHz, DMSO-$d_6$, RT) δ 8.04 (d, J=2.80 Hz, 1H), 7.92 (dd, J=2.40 Hz, 1H), 7.47-7.45 (m, 1H).

Step 2: To a suspension of $MgSO_4$ (8.78 g, 73.0 mmol) in $CH_2Cl_2$ (30 mL) at 20-25° C. was added $H_2SO_4$ (1.79 g, 18.2 mmol, 973 μL), followed after 10 min by 5-bromo-2-(trifluoromethoxy)benzoic acid (5.20 g, 18.2 mmol) and t-BuOH (6.76 g, 91.2 mmol, 8.72 mL). The resulting mixture was stirred at 20-25° C. for 48 h. The mixture was quenched with $NaHCO_3$ solution (sat. aq., 50 mL), extracted with EtOAc (3×25 mL), and the combined organic extracts were dried over $Na_2SO_4$, filtered, and concentrated. Purification by column chromatography ($SiO_2$, petroleum ether/EtOAc=50:1 to 3:1) afforded tert-butyl 5-bromo-2-(trifluoromethoxy)benzoate (4.20 g, 68%) as a light yellow oil.

$^1$H-NMR (400 MHz, $CDCl_3$, RT): δ 8.00 (d, J=2.40 Hz, 1H), 7.64 (dd, J=2.40 Hz, 1H), 7.18 (d, J=8.40 Hz, 1H), 1.59 (s, 9H).

This product could then be transformed further into e.g. the compounds I-70, I-71, I-72, I-87, and I-103, analogously to the above examples.

Example 18: Synthesis of 2-cyano-3-[[5-(3,5-dichlorophenyl)-5-(trifluoromethyl)-4H-isoxazol-3-yl]amino]benzoic acid Step 1: To a solution of methyl 3-bromo-2-iodo-benzoate (30.0 g, 124 mmol) in THF (60.0 mL) and $H_2O$ (60.0 mL) at 20-25° C. was added $LiOH{\cdot}H_2O$ (5.24 g, 124 mmol), and the resulting mixture was stirred at that temperature for 12 h. Then the pH of the mixture was adjusted to 1-2 with HCl solution (1.0 N in $H_2O$), the aqueous phase was exacted with EtOAc (2×200 mL), and the combined organic extracts were dried over $Na_2SO_4$, filtered, and concentrated to give 3-bromo-2-iodo-benzoic acid (27.0 g, 91%) as a yellow oil.

$^1$H-NMR (400 MHz, $CDCl_3$, RT): δ 7.84-7.82 (m, 1H), 7.74-7.72 (m, 1H), 7.33-7.30 (m, 1H).

Step 2: To a suspension of $MgSO_4$ (39.7 g, 330 mmol) in $CH_2Cl_2$ (190 mL) at 20-25° C. was added $H_2SO_4$ (8.10 g, 82.5 mmol), followed after 15 min by 3-bromo-2-iodo-benzoic acid (27.0 g, 82.5 mmol) and t-BuOH (30.6 g, 412 mmol), and the resulting mixture was stirred at that temperature for 16 h. The mixture was poured into $NaHCO_3$ solution (sat. aq., 150 mL), the aqueous phase was exacted with EtOAc (2×100 mL), and the combined organic extracts were dried over $Na_2SO_4$, filtered, and concentrated under reduce pressure. Purification by column chromatography ($SiO_2$, petroleum ether/EtOAc=100:1 to 1:1) afforded tert-butyl 3-bromo-2-iodo-benzoate (29.0 g, 91%) as a white solid.

$^1$H-NMR (400 MHz, $CDCl_3$, RT): δ 7.70-7.67 (m, 1H), 7.37-7.34 (m, 1H), 7.24 (d, J=8.0 Hz, 1H), 1.62 (s, 9H).

Step 3: To a solution of tert-butyl 3-bromo-2-iodo-benzoate (29.0 g, 75.7 mmol) in N-methyl-2-pyrrolidone (300 mL) at 20-25° C. was added CuCN (8.14 g, 90.8 mmol), and the resulting mixture was heated to 60° C. and stirred at that temperature for 5 h. Then the reaction mixture was filtered, the filter cake was washed with EtOAc (3×70 mL), and the combined filtrates were concentrated under reduce pressure. Purification by column chromatography ($SiO_2$, petroleum ether/EtOAc=100/1 to 3/1) afforded tert-butyl 3-bromo-2-cyano-benzoate (18.0 g, 83%) as a white solid.

$^1$H-NMR (400 MHz, $CDCl_3$, RT): δ 8.01-7.99 (m, 1H), 7.87-7.85 (m, 1H), 7.52-7.48 (m, 1H), 1.65 (s, 9H).

Step 4: To a solution of 5-(3,5-dichlorophenyl)-5-(trifluoromethyl)-4H-isoxazol-3-amine (10.0 g, 33.4 mmol) and tert-butyl 3-bromo-2-cyano-benzoate (9.91 g, 35.1 mmol) in 1,4-dioxane (60.0 mL) at 20-25° C. under an atmosphere of $N_2$ was added Xantphos (2.90 g, 5.02 mmol), $Cs_2CO_3$ (16.3 g, 50.1 mmol) and $Pd_2(dba)_3$ (3.06 g, 3.34 mmol), and the resulting mixture was heated to 80° C. and stirred at that temperature for 18 h. The reaction mixture was filtered, the filter cake was washed with EtOAc (2×80 mL), and the combined filtrates were concentrated. Purification column chromatography ($SiO_2$, petroleum ether/ethyl acetate=50/1 to 1/1) afforded tert-butyl 2-cyano-3-[[5-(3,5-dichlorophenyl)-5-(trifluoromethyl)-4H-isoxazol-3-yl]amino]benzoate (6.00 g, 36%) as a white solid.

$^1$H-NMR (400 MHz, $CDCl_3$, RT): δ 9.14 (s, 1H), 8.19 (d, J=12.0 Hz, 1H), 7.78-7.73 (m, 2H), 7.64-7.62 (m, 3H), 4.23-3.93 (m, 2H), 1.54 (s, 9H).

This product could then be transformed further into e.g. the compounds I-82, I-86, I-93, and I94, analogously to the above examples.

Example 19: Synthesis of 3-chloro-6-[[5-(3,5-dichlorophenyl)-5-(trifluoromethyl)-4H-isoxazol-3-yl]amino]pyridine-2-carboxylic acid Step 1: To a suspension of $MgSO_4$ (25.1 g, 208 mmol) and $H_2SO_4$ (5.11 g, 52.1 mmol, 2.78 mL) in $CH_2Cl_2$ (70 mL) at 20-25° C. was added after 15 min, 3,6-dichloropyridine-2-carboxylic acid (10.0 g, 52.1 mmol) and t-BuOH (19.3 g, 260 mmol, 24.9 mL), and the resulting reaction mixture was stirred at that temperature for 24 h. The reaction mixture was quenched by the addition of $NaHCO_3$ solution (sat. aq., 50 mL), the aqueous phase was extracted with EtOAc (2×50 mL), and the combined organic extracts were dried over $Na_2SO_4$, filtered, and concentrated under reduced pressure. Purification by column chromatography ($SiO_2$, petroleum ether/EtOAc=30:1 to 3:1) afforded tert-butyl 3,6-dichloro-pyridine-2-carboxylate (9.60 g, 74%) as a yellow solid.

$^1$H-NMR (400 MHz, $CDCl_3$, RT) δ 7.70 (d, J=8.4 Hz, 1H) 7.35 (d, J=8.8 Hz, 1H) 6.84 (d, J=8.8 Hz, 1H) 1.63 (s, 9H).

Step 2: To a solution of 5-(3,5-dichlorophenyl)-5-(trifluoromethyl)-4H-isoxazol-3-amine (10.0 g, 33.4 mmol) and tert-butyl 3,6-dichloropyridine-2-carboxylate (8.30 g, 33.4 mmol) in 1,4-dioxane (200 mL) under an atmosphere of $N_2$ was added $Cs_2CO_3$ (16.4 g, 50.2 mmol), Xantphos (2.90 g, 5.02 mmol) and $Pd_2(dba)_3$ (3.06 g, 3.34 mmol), before the reaction mixture was heated to 80° C. and stirred at that temperature for 24 h. Then the mixture was filtered and concentrated. Purification by column chromatography ($SiO_2$, petroleum ether/EtOAc=100:1 to 1:1) afforded tert-butyl 3-chloro-6-[[5-(3,5-dichlorophenyl)-5-(trifluoromethyl)-4H-isoxazol-3-yl]amino]pyridine-2-carboxylate (9.60 g, 74%) as a yellow solid.

$^1$H-NMR (400 MHz, CDCl3, RT): δ 7.55 (d, J=2.0 Hz, 4H), 7.28 (d, J=2.0 Hz, 1H), 3.78-3.71 (m, 2H), 1.69 (s, 9H).

Step 3: tert-Butyl 3-chloro-6-[[5-(3,5-dichlorophenyl)-5-(trifluoromethyl)-4H-isoxazol-3-yl]amino]pyridine-2-carboxylate (7.00 g, 13.7 mmol) was dissolved in $F_3CCO_2H$ (35.0 mL), heated to 40° C., and stirred at that temperature for 12 h. Then the mixture was poured into water (10 mL), the obtained solid washed with water (2×15 mL), and dried. Purification by reversed-phase HPLC (neutral condition) afforded 3-chloro-6-[[5-(3,5-dichlorophenyl)-5-(trifluoromethyl)-4H-isoxazol-3-yl]amino]pyridine-2-carboxylic acid (2.25 g, 45%) as a pink solid.

$^1$H-NMR (400 MHz, $CDCl_3$, RT) δ 7.83-7.75 (m, 2H), 7.64-7.59 (m, 3H), 7.30 (s, 1H), 4.01-3.59-3.76 (m, 2H).

This product could then be transformed further into e.g. the compounds I-80, I-83, and I-96, analogously to the above examples.

Example 20: Synthesis of methyl 5-bromo-2-(difluoromethoxy)benzoate

Step 1: To a solution of methyl 5-bromo-2-hydroxybenzoate (100 g, 432 mmol) and $Na_2CO_3$ (55.0 g, 518 mmol) in DMF (1.0 L) at 20-25° C. was added sodium chlorodifluoroacetate (79.1 g, 519 mmol), before the mixture was heated to 90° C. and stirred at that temperature for 14 hours. Then, the reaction mixture was allowed to cool to 20-25° C., the pH was adjusted to 6-7 with HCl solution (1.0 M in $H_2O$), and the aqueous phase was extracted with EtOAc (2×500 mL). The combined organic extracts were dried over $Na_2SO_4$, filtered, and concentrated. Purification by column chromatography ($SiO_2$, petroleum ether/EtOAc=100:1 to 1:1) afforded methyl 5-bromo-2-(difluoromethoxy)benzoate (15.0 g, 6%) as a yellow oil.

$^1$H-NMR (400 MHz, $CDCl_3$): δ 8.00 (d, J=4.0 Hz, 1H), 7.64-7.61 (m, H), 7.15 (d, J=4.0 Hz, 1H), 6.55-6.36 (m, 1H), 3.92 (s, 1H).

This product could then be transformed further into e.g. the compounds I-65, I-67, I-74, I-95, and I-105, analogously to the above examples.

Example 21: Synthesis of methyl 5-bromo-2-(trifluoromethyl)benzoate

Step 1: A mixture of methyl 5-bromo-2-iodo-benzoate (20.0 g, 58.6 mmol), methyl 2,2-difluoro-2-fluorosulfonyl-acetate (16.9 g, 87.9 mmol), and CuBr (1.01 g, 7.04 mmol) in N-methyl-2-pyrrolidone (120 mL) at 20-25° C. was degassed and purged with $N_2$ (3×), before the mixture was heated to 100° C. and stirred at that temperature for 18 h. Then the reaction mixture was allowed to cool to 20-25° C., filtered, and the filter cake was washed with EtOAc (3×100 mL). The combined filtrates were diluted with $H_2O$ (100 mL), the phases were separated, and the aqueous phase extracted with EtOAc (3×100 mL). The combined organic extracts were dried over $Na_2SO_4$, filtered, and concentrated. Purification by column chromatography ($SiO_2$, petroleum ether/EtOAc=50:1 to 3:1) afforded methyl 5-bromo-2-(trifluoromethyl)benzoate (15.0 g, 72%) as a light-yellow oil.

$^1$H-NMR (400 MHz, $CDCl_3$, RT): δ 7.93 (s, 1H), 7.74-7.72 (m, 1H), 7.60 (d, J=8.0 Hz, 1H), 3.94 (s, 3H).

This product could then be transformed further into e.g. the compounds I-66, I-79, and I-107, analogously to the above examples.

Example 22: Synthesis of (1-isoxazol-4-ylcyclopropyl)ammonium chloride

Step 1: To a solution of isoxazole-4-carbonitrile (200 mg, 2.13 mmol), and $Ti(Oi\text{-}Pr)_4$ (665 mg, 2.34 mmol) in $Et_2O$ (10 mL) at −70° C. under an atmosphere of $N_2$ was added EtMgBr solution (3.0M in $Et_2O$, 1.49 mL, 4.46 mmol) dropwise. The mixture was stirred at that temperature for 10 min before it was allowed to warm to 20-25° C. and stirred at that temperature for an additional 0.5 h. Then $BF_3{\cdot}Et_2O$ (604 mg, 4.25 mmol) was added, and the mixture was stirred at 20-25° C. for another 1 h. The reaction mixture was quenched with ice-water (10 mL) and filtered to afford 1-isoxazol-4-ylcyclopropanamine as a yellow solution, which was directly used in the next step.

Step 2: To a solution of 1-isoxazol-4-ylcyclopropanamine (550 mg, 4.43 mmol, theoretical yield from prior reaction) in THF (10 mL) and $H_2O$ (10 mL) was added NaOH (6.0 M in $H_2O$, 3.69 mL), and $Boc_2O$ (4.83 g, 22.2 mmol), and the resulting mixture was stirred at 20-25° C. for 15 h. Then the reaction mixture was extracted with EtOAc (3×10 mL), and the combined organic extracts were washed with NaCl solution (sat. aq., 1×10 mL), dried over $Na_2SO_4$, filtered, and concentrated under reduced pressure. Purification by column chromatography ($SiO_2$, petroleum ether/EtOAc=99:1 to 66:33; gradient) afforded tert-butyl N-(1-isoxazol-4-ylcyclopropyl)carbamate (0.6 g, 60%) as a light yellow solid.

$^1$H NMR (400 MHz, $CDCl_3$, RT): δ 8.28 (brs, 1H), 8.19 (brs, 1H), 5.31-5.07 (m, 1H), 1.44 (s, 9H), 1.24-1.18 (m, 2H), 1.11-1.02 (m, 2H).

Step 3: A solution of tert-butyl N-(1-isoxazol-4-ylcyclopropyl)carbamate in HCl/dioxane (4.0 N, 2.0 mL) was stirred at 20-25° C. for 15 h. Then MTBE (50 mL) was added, the mixture was stirred for 10 min, and then filtered. The filter cake was dried under reduced pressure to give (1-isoxazol-4-ylcyclopropyl)ammonium chloride (240 mg, 57%) as a light yellow solid.

$^1$H-NMR (400 MHz, DMSO-d6, RT): δ 9.18 (br s, 3H), 9.06 (s, 1H), 8.80 (s, 1H), 1.51-1.30 (m, 2H), 1.22-1.02 (m, 2H).

This product could then be transformed further into e.g. the compounds I-163, and I-164 analogously to the above examples.

Example 23: Synthesis of (1-oxazol-4-ylcyclopropyl)ammonium chloride

Step 1: To a solution of oxazole-4-carbonitrile (500 mg, 5.30 mmol), and $Ti(Oi\text{-}Pr)_4$ (1.66 g, 5.83 mmol) in $Et_2O$ (25 mL) at −70° C. under an atmosphere of $N_2$ was added EtMgBr solution (3.0 M in $Et_2O$, 3.70 mL, 11.1 mmol) dropwise. The mixture was stirred for 10 min at that temperature, and then warmed to 20-25° C., and stirred at that temperature for an additional 1 h. The mixture was cooled to 0° C., $BF_3{\cdot}Et_2O$ (1.51 g, 10.6 mmol) was added, and the mixture was stirred at 20-25° C. for 1 h. Then the reaction mixture was quenched by ice-water (25 mL) at 0°

C. and filtered to give 1-oxazol-4-ylcyclopropanamine as a yellow solution, which was directly used in the next step.

Step 2: To a solution of 1-oxazol-4-ylcyclopropanamine (660 mg, 5.32 mmol) in MeCN (25 mL) and $H_2O$ (25 mL) was added NaOH (6.0 M in $H_2O$, 4.43 mL), and $Boc_2O$ (5.8 g, 26.6 mmol). The mixture was stirred at 20-25° C. for 15 h. Then the mixture was extracted with EtOAc (3×50 mL), and the combined organic extracts were washed with NaCl solution (sat. aq., 1×50 mL), dried over $Na_2SO_4$, filtered, and concentrated under reduced pressure. Purification by column chromatography ($SiO_2$, petroleum ether/EtOAc=99:1 to 50:50) afforded tert-butyl N-(1-oxazol-4-ylcyclopropyl)carbamate (360 mg, 30%) as yellow solid.

$^1$H-NMR (400 MHz, DMSO-d6, RT): δ 8.20 (s, 1H), 7.65 (br d, J=12.8 Hz, 2H), 1.44-1.33 (m, 9H), 1.17-1.07 (m, 2H), 1.04-0.93 (m, 2H).

Step 3: A solution of tert-butyl N-(1-oxazol-4-ylcyclopropyl)carbamate (360 mg, 1.62 mmol) in HCl/dioxane (4.0M, 4.0 mL) was stirred at 20-25° C. for 15 h. Then MTBE (50 mL) was added, the mixture was stirred for another 10 min, and then filtered. The filter cake was dried under reduced pressure to give (1-oxazol-4-ylcyclopropyl)ammonium chloride (260 mg, crude) as a light red solid.

$^1$H-NMR (400 MHz, DMSO-d6, RT) δ 11.5 (brs, 1H), 9.23 (brs, 3H), 8.42 (d, J=0.9 Hz, 1H), 8.17 (d, J=0.9 Hz, 1H), 1.50-1.35 (m, 2H), 1.25-1.04 (m, 2H).

This product could then be transformed further into e.g. the compounds I-152, and I-155 analogously to the above examples.

Example 24: Synthesis of 1-[1-(ethoxymethyl)pyrazol-4-yl]cyclopropanamine

Step 1: To a solution of 1H-pyrazole-4-carbonitrile (2.00 g, 21.5 mmol) in DMF (20 mL) at 0° C. and under an atmosphere of $N_2$, was added NaH (60 wt % in mineral oil, 1.03 g, 25.8 mmol) in portions. The mixture was stirred at that temperature for 30 min before chloromethoxyethane (2.40 g, 25.8 mmol) in DMF (20 mL) was added dropwise. The mixture was gradually warmed to 20-25° C. and stirred at that temperature for 15 h. Then the reaction mixture was poured into ice-water (100 mL), extracted with MTBE (3×20 mL), and the combined organic extracts were washed with NaCl solution (sat. aq., 1×20 mL), dried over $Na_2SO_4$, filtered, and concentrated under reduced pressure. Purification by column chromatography ($SiO_2$, petroleum ether/EtOAc=99:1 to 33:66) afforded 1-(ethoxymethyl)pyrazole-4-carbonitrile (2.10 g, 65%) as a white solid.

$^1$H-NMR (400 MHz, $CDCl_3$, RT): δ 8.01 (s, 1H), 7.83 (s, 1H), 5.47 (s, 2H), 3.57 (q, J=7.1 Hz, 2H), 1.20 (t, J=7.1 Hz, 3H).

Step 2: To a solution of 1-(ethoxymethyl)pyrazole-4-carbonitrile (1.00 g, 6.62 mmol), $Ti(Oi\text{-}Pr)_4$ (2.07 g, 7.28 mmol) in $Et_2O$ (30 mL) at −70° C. under $N_2$ was added EtMgBr solution (3.0 M in $Et_2O$, 4.60 mL, 13.9 mmol) dropwise. The mixture was stirred at that temperature for 10 min, then warmed to 20° C., and stirred at that temperature for 1 h. The mixture was cooled to 0° C., $BF_3{\cdot}Et_2O$ (1.88 g, 13.2 mmol) was added, and the mixture was stirred at 20° C. for 1 h. Then the reaction mixture was quenched with ice-water (60 mL), filtered to give the crude, and purified by prep-HPLC to give 1-[1-(ethoxymethyl)pyrazol-4-yl]cyclopropanamine (320 mg, 27%) as a light yellow solid.

$^1$H-NMR (400 MHz, DMSO-d6, RT): δ 7.63 (s, 1H), 7.29 (s, 1H), 5.30 (s, 2H), 3.46-3.41 (m, 2H), 2.24 (br s, 2H), 1.05 (t, J=7.0 Hz, 3H), 0.86-0.78 (m, 2H), 0.73-0.66 (m, 2H).

This product could then be transformed further into e.g. the compound I-149, analogously to the above examples.

Example 25: Synthesis of [1-[1-(ethoxymethyl)pyrazol-3-yl]cyclopropyl]ammonium chloride Step 1: To a solution of 1H-pyrazole-3-carbonitrile (2.00 g, 21.5 mmol) in DMF (20 mL) at 0° C. under $N_2$ was added NaH (60 wt % in mineral oil, 1.03 g, 25.8 mmol) in portions, and the mixture was stirred at that temperature for 30 min. Chloromethoxyethane (2.40 g, 25.8 mmol) in DMF (20 mL) was added dropwise, before the mixture was gradually warmed to 25° C. and stirred at that temperature for 15 h. Then the reaction mixture was poured into ice-water (100 mL), the aqueous phase extracted with MTBE (3×20 mL), and the combined organic extracts were washed with NaCl solution (sat. aq., 1×20 mL), dried over $Na_2SO_4$, filtered, and concentrated under reduced pressure. Purification by column chromatography ($SiO_2$, petroleum ether/EtOAc=99:1 to 33:66) afforded 1-(ethoxymethyl)pyrazole-3-carbonitrile (1.20 g, 37%) as a colourless oil.

$^1$H-NMR (400 MHz, $CDCl_3$, RT): δ 7.67 (d, J=2.4 Hz, 1H), 6.74 (d, J=2.4 Hz, 1H), 5.47 (s, 2H), 3.54 (q, J=7.0 Hz, 2H), 1.18 (t, J=7.1 Hz, 3H).

Step 2: To a solution of 1-(ethoxymethyl)pyrazole-3-carbonitrile (1.20 g, 7.92 mmol), and $Ti(Oi\text{-}Pr)_4$ (2.48 g, 8.71 mmol) in $Et_2O$ (60 mL) at −70° C. under $N_2$ was added EtMgBr solution (3.0M in $Et_2O$, 5.50 mL, 16.6 mmol) dropwise. The mixture was stirred at that temperature for 10 min, then warmed to 20° C., and stirred at that temperature for 1 h. The mixture was cooled to 0° C., $BF_3{\cdot}Et_2O$ (2.26 g, 15.8 mmol) was added, and the mixture was stirred at 20° C. for 1 h. Then the reaction mixture was quenched by ice-water (60 mL), and filtered to give 1-[1-(ethoxymethyl)pyrazol-3-yl]cyclopropanamine (1.4 g, crude) as a yellow solution, which was directly used in the next step.

Step 3: To a solution of 1-[1-(ethoxymethyl)pyrazol-3-yl]cyclopropanamine (1.32 g, 7.28 mmol) in MeCN (60 mL) and $H_2O$ (60 mL) was added aq. NaOH (6M, 6.1 mL), and $Boc_2O$ (7.95 g, 36.4 mmol), and the resulting mixture was stirred at 20° C. for 15 h. Then the mixture was extracted with EtOAc (3×50 mL), and the combined organic extracts were washed with NaCl solution (sat. aq., 1×50 mL), dried over $Na_2SO_4$, filtered, and concentrated under reduced pressure. Purification by column chromatography ($SiO_2$, petroleum ether/EtOAc=99:1 to 50:50) afforded tert-butyl N-[1-[1-(ethoxymethyl)pyrazol-3-yl]cyclopropyl]carbamate (630 mg, 31%) as a white solid.

$^1$H-NMR (400 MHz, DMSO-d6, RT): δ 7.69 (s, 1H), 7.58 (s, 1H), 6.05 (s, 1H), 5.27 (s, 2H), 3.44 (q, J=6.7 Hz, 2H), 1.38 (s, 8H), 1.14-0.88 (m, 7H).

Step 4: A solution of tert-butyl N-[1-[1-(ethoxymethyl)pyrazol-3-yl]cyclopropyl]carbamate (630 mg, 2.24 mmol) in HCl/dioxane (4M, 5.6 mL) was stirred at 25° C. for 15 h. Then MTBE (6 mL) was added, the mixture was stirred for 10 min, and then filtered. The filter cake was dried under reduced pressure to give [1-[1-(ethoxymethyl)pyrazol-3-yl]cyclopropyl]ammonium chloride (400 mg, 81%) as a white solid.

$^1$H-NMR (400 MHz, DMSO-d6, RT): δ 8.98 (br s, 3H), 7.91 (d, J=2.4 Hz, 1H), 6.33 (d, J=2.4 Hz, 1H), 5.36 (s, 2H), 3.48 (q, J=7.1 Hz, 2H), 1.47-1.37 (m, 2H), 1.19-1.12 (m, 2H), 1.07 (t, J=7.0 Hz, 3H).

This product could then be transformed further into e.g. the compound I-153, analogously to the above examples.

Example 26: Synthesis of [1-[1-(ethoxymethyl)imidazol-4-yl]cyclopropyl]ammonium chloride Step 1: To a solution of 1H-imidazole-4-carbonitrile (12.0 g, 128 mmol) in DMF (150 mL) at 0° C. under an atmosphere of $N_2$ was added NaH (60 wt % in mineral oil, 6.15 g, 155 mmol) in portions.

The resulting mixture was stirred at that temperature for 30 min, before chloromethoxyethane (14.6 g, 155 mmol) in DMF (50 mL) was added dropwise. The mixture was gradually warmed to 25° C. and stirred for 15 h. Then the reaction mixture was poured into ice-water (500 mL), the aqueous phase was extracted with MTBE (3×100 mL), and the combined organic extracts were washed with NaCl solution (sat. aq., 1×100 mL), dried over $Na_2SO_4$, filtered, and concentrated under reduced pressure. Purification by column chromatography ($SiO_2$, petroleum ether/EtOAc=99:1 to 50:50) afforded 1-(ethoxymethyl)pyrazole-3-carbonitrile (2.0 g, 11%) as a yellow oil.

Step 2: To a solution of 1-(ethoxymethyl)pyrazole-3-carbonitrile (0.50 g, 3.3 mmol), and $Ti(Oi\text{-}Pr)_4$ (1.03 g, 3.64 mmol) in $Et_2O$ (15 mL) at −70° C. under $N_2$ was added EtMgBr solution (3.0 M in $Et_2O$, 2.2 mL, 6.6 mmol) dropwise. The mixture was stirred at that temperature for 10 min, then warmed to 20° C., and stirred at that temperature for 1 h. The mixture was cooled to 0° C., $BF_3{\cdot}Et_2O$ (0.94 g, 6.6 mmol) was added, and the mixture was stirred at 20° C. for 1 h. Then the reaction mixture was quenched by ice-water (15 mL), and then filtered to give 1-[1-(ethoxymethyl)imidazol-4-yl]cyclopropanamine (0.60 g, crude) as a yellow solution, which was directly used in the next step.

Step 3: To a solution of 1-[1-(ethoxymethyl)imidazol-4-yl]cyclopropanamine (0.60 g, 3.3 mmol) in MeCN (15 mL) and $H_2O$ (15 mL) was added aq. NaOH (6.0M, 2.8 mL), and $Boc_2O$ (3.61 g, 16.6 mmol), and the mixture was stirred at 20° C. for 15 h. Then the mixture was extracted with EtOAc (3×10 mL), and the combined organic extracts were washed with NaCl solution (sat. aq., 1×10 mL), dried over $Na_2SO_4$, filtered, and concentrated under reduced pressure. Purification by column chromatography ($SiO_2$, petroleum ether/EtOAc=99:1 to 50:50) afforded tert-butyl N-[1-[1-(ethoxymethyl)imidazol-4-yl]cyclopropyl]carbamate (390 mg, 41%) as a light yellow solid.

Step 4: A solution of tert-butyl N-[1-[1-(ethoxymethyl)imidazol-4-yl]cyclopropyl]carbamate (390 mg, 1.38 mmol) in HCl/dioxane (4.0M, 10 mL) was stirred at 25° C. for 15 h. Then MTBE (6 mL) was added, the mixture was stirred for 10 min, and then filtered. The filter cake was dried under reduced pressure to give [1-[1-(ethoxymethyl)imidazol-4-yl]cyclopropyl]ammonium chloride (230 mg, 90%) as a white solid.

$^1$H-NMR (400 MHz, DMSO-d6, RT): δ 7.58 (d, J=1.3 Hz, 1H), 7.08 (d, J=1.4 Hz, 1H), 5.24 (s, 2H), 3.40 (d, J=7.1 Hz, 2H), 1.09-1.06 (m, 3H), 0.90-0.85 (m, 2H), 0.78-0.70 (m, 2H).

This product could then be transformed further into e.g. the compound I-161, analogously to the above examples.

Example 27: Synthesis of 2-chloro-5-[[5-(3,5-dichlorophenyl)-5-(trifluoromethyl)-4H-isoxazol-3-yl]amino]-N-(1-pyridazin-4-ylcyclopropyl)benzamide [I-162]

Step 1: A solution of 2-chloro-5-[[5-(3,5-dichlorophenyl)-5-(trifluoromethyl)-4H-isoxazol-3-yl]-amino]-N-(1-ethynylcyclopropyl)benzamide (600 mg, 1.16 mmol, synthesized analogously as described above), and 1,2,4,5-tetraazine (480 mg, 5.80 mmol), in toluene (20 mL) was stirred at 110° C. for 5 d. Then the mixture was filtered, the filter cake was triturated with EtOAc (50 mL), and then filtered again to give 2-chloro-5-[[5-(3,5-dichlorophenyl)-5-(trifluoromethyl)-4H-isoxazol-3-yl]amino]-N-(1-pyridazin-4-ylcyclopropyl)benzamide [I-162] (300 mg, 45%) as a light yellow solid.

$^1$H-NMR (400 MHz, DMSO-d6, RT): δ 9.59 (s, 1H), 9.34 (s, 1H), 9.19-8.98 (m, 2H), 7.79 (s, 1H), 7.66 (s, 2H), 7.53 (d, J=2.3 Hz, 1H), 7.52-7.46 (m, 2H), 7.43 (dd, J=2.6, 5.6 Hz, 1H), 4.00-3.85 (m, 2H), 1.62-1.50 (m, 2H), 1.45-1.36 (m, 2H).

Example 28: Synthesis of 5-(2,6-dichloro-4-pyridyl)-5-(trifluoromethyl)-4H-isoxazol-3-amine Step 1: To a solution of 4-bromo-2,6-dichloro-pyridine (5.00 g, 22.0 mmol) in DMF (60 mL) at 20-25° C. under an atmosphere of $N_2$ was added bis(pinacolato)diboron (6.69 g, 26.4 mmol), KOAc (6.69 g, 26.4 mmol), and $Pd(dppf)Cl_2$ (1.5 g, 2.2 mmol). The reaction was heated to 100° C. and stirred at that temperature for 1 h. Then the reaction mixture was quenched with $H_2O$ (50 mL), the aqueous phase was extracted with EtOAc (3×60 mL), and the combined organic extracts were washed with NaCl solution (sat. aq., 2×20 mL), dried over $Na_2SO_4$, filtered, and concentrated to give 2,6-dichloro-4-(4,4,5,5-tetramethyl-1,3,2-dioxaborolan-2-yl)pyridine (7.2 g) as a yellow solid, which was used for the next step directly without further purification.

Step 2: To a solution of 2,6-dichloro-4-(4,4,5,5-tetramethyl-1,3,2-dioxaborolan-2-yl)pyridine (5.00 g, 18.2 mmol) in dioxane (50 mL) and $H_2O$ (10 mL) at 20-25° C. under an atmosphere of $N_2$ was added 2-bromo-3,3,3-trifluoro-prop-1-ene (6.38 g, 36.5 mmol), $K_2CO_3$ (4.72 g, 36.5 mmol), and $Pd(PPh_3)_2Cl_2$ (1.28 g, 1.82 mmol). The mixture was heated to 80° C. and stirred at that temperature for 12 h in sealed vessel. Then the reaction mixture was quenched with $H_2O$ (50 mL), the aqueous phase was extracted with EtOAc (3×60 mL), and the combined organic extracts were washed with NaCl solution (sat. aq., 1×20 mL), dried over $Na_2SO_4$, filtered and concentrated. Purification by column chromatography ($SiO_2$, petroleum ether/EtOAc=100:0 to 15:85) afforded 2,6-dichloro-4-[1-(trifluoromethyl)vinyl]pyridine (2.20 g, 50%) as a colourless oil.

$^1$H-NMR (400 MHz, $CDCl_3$, RT): δ 7.32-7.32 (m, 1H) 7.34 (s, 1H) 6.22 (s, 1H) 6.03 (d, J=0.88 Hz, 1H).

Step 3: To a solution of 1,1-dibromoformaldoxime (1.00 g, 38.6 mmol) in THF (100 mL) at −70° C. under an atmosphere of $N_2$ was added bis(4-methoxybenzyl)amine (0.940 g, 46.7 mmol), and $iPr_2NEt$ (0.500 g, 38.6 mmol) dropwise. The mixture was stirred at that temperature for additional 10 min, before a solution of 6-dichloro-4-[1-(trifluoromethyl)vinyl]pyridine (1.47 g, 38.6 mmol) and $iPr_2NEt$ (1.00 g, 77.2 mmol) in THF (10 mL) was added dropwise to the above reaction solution at −70° C. The reaction mixture was allowed to warm to 20-25° C. and then stirred at that temperature for 12 h. The reaction mixture was quenched with $H_2O$ (50 mL), the aqueous phase was extracted with EtOAc (3×50 mL), and the combined organic extracts were washed with NaCl solution (sat. aq., 1×100 mL), dried over $Na_2SO_4$, filtered, and concentrated. Purification by column chromatography ($SiO_2$, petroleum ether/EtOAc=100:0 to 18:82) afforded 5-(2,6-dichloro-4-pyridyl)-N,N-bis[(4-methoxyphenyl)methyl]-5-(trifluoromethyl)-4H-isoxazol-3-amine (1.50 g, 46%) as a yellow solid.

$^1$H-NMR (400 MHz, $CDCl_3$, RT): δ 7.45 (s, 2H) 7.06 (d, J=8.6 Hz, 4H) 6.82-6.89 (m, 4H) 4.27 (s, 4H) 3.81 (s, 6H).

Step 4: 5-(2,6-dichloro-4-pyridyl)-N,N-bis[(4-methoxyphenyl)methyl]-5-(trifluoromethyl)-4H-isoxazol-3-amine (200 mg, 0.370 mmol) was dissolved in $F_3CCO_2H$ (5.0 mL) and the resulting mixture was stirred at 20-25° C. for 12 h. Then the reaction mixture was quenched with $H_2O$ (10 mL), the aqueous phase was extracted with EtOAc (3×3 mL), and the combined organic extracts were washed with NaCl solution (sat. aq., 1×10 mL), dried over $Na_2SO_4$, filtered, and concentrated. Purification by column chromatography ($SiO_2$, petroleum ether/EtOAc=100:0 to 35:75, gradient) afforded 5-(2,6-dichloro-4-pyridyl)-5-(trifluoromethyl)-4H-isoxazol-3-amine (30 mg, 27%) as a white solid.

$^1$H-NMR (400 MHz, $CDCl_3$, RT): δ 7.47 (s, 2H) 3.74 (d, J=16.5 Hz, 1H) 3.29 (d, J=16.9 Hz, 1H).

This product could then be transformed further into e.g. the compound I-173, analogously to the above examples.

Example 29: Synthesis of 5-(4-bromo-2-thienyl)-5-(trifluoromethyl)-4H-isoxazol-3-amine Step 1: To a solution of 4-bromothiophene-2-carbaldehyde (10.0 g, 52.3 mmol) in THF (100 mL) at 0° C. was added CsF (1.60 g, 10. mmol), and $Me_3Si—CF_3$ (9.00 g, 52.3 mmol) dropwise, and the resulting mixture was stirred at that temperature for 2 h. Then the reaction mixture was carefully quenched by the dropwise addition of HCl solution (2N in $H_2O$, 90 mL) and then stirred at 0° C. for additional 2 h. The aqueous phase was extracted with EtOAc (3×50 mL), and the combined organic extracts were washed with NaCl solution (sat. aq., 1×50 mL), dried over $Na_2SO_4$, filtered, and concentrated to give 1-(4-bromo-2-thienyl)-2,2,2-trifluoro-ethanol (16.3 g, crude) as yellow oil.

Step 2: To a mixture of 1-(4-bromo-2-thienyl)-2,2,2-trifluoro-ethanol (10.3 g, 39.5 mmol) in $CH_2Cl_2$ (100 mL) at 0° C. was added 3-oxo-1λ5,2-benziodoxole-1,1,1(3H)-triyl triacetate ("Dess-Martin Periodinane") (25.1 g, 59.2 mmol) in portions, and the reaction was then stirred at 20-25° C. for 3 h. Then the reaction mixture was quenched with $NaHCO_3$ solution (sat. aq., 300 mL), the aqueous phase was extracted with $CH_2Cl_2$ (3×200 mL), and the combined organic extracts were washed with $Na_2S_2O_3$ (sat. aq., 1×200 mL) and NaCl solution (sat. aq., 1×200 mL), dried over $Na_2SO_4$, filtered, and concentrated. Purification by column chromatography (petroleum ether=100%) afforded 1-(4-bromo-2-thienyl)-2,2,2-trifluoro-ethanone (6.10 g, 60%) as yellow oil.

$^1$H-NMR (400 MHz, $CDCl_3$, RT): δ 7.86 (s, 1H), 7.80 (s, 1H).

Step 3: To a mixture of 1-(4-bromo-2-thienyl)-2,2,2-trifluoro-ethanone (7.50 g, 29.0 mmol) and $MePPh_3Br$ (12.4 g, 34.7 mmol) in THF (80 mL) at 0° C. was added t-BuOK solution (35 mL, 1.0 M in THF) dropwise, and the resulting mixture was stirred at that temperature for 3 h. Then the mixture was poured into $NH_4Cl$ solution (sat aq., 50 mL), the aqueous phase was extracted with EtOAc (3×100 mL), and the combined organic extracts were washed with NaCl solution (sat. aq., 1×60 mL), dried over $Na_2SO_4$, filtered, and concentrated. Purification by column chromatography (petroleum ether=100%) afforded 4-bromo-2-[1-(trifluoromethyl)vinyl]thiophene (4.70 g, 63%) as red oil.

$^1$H-NMR (400 MHz, $CDCl_3$, RT): δ 7.22 (d, J=1.1 Hz, 1H), 7.13 (s, 1H), 5.90-5.84 (m, 2H).

Step 4: To a solution of bis(4-methoxybenzyl)amine (5.00 g, 19.4 mmol) in THF (30 mL) at −70° C. was added a solution of 1,1-dibromoformaldoxime (4.73 g, 23.3 mmol) in THF (10 mL) and $iPr_2NEt$ (2.50 g, 19.4 mmol) dropwise, and the mixture was stirred at that temperature for 30 min. Then, 4-bromo-2-[1-(trifluoromethyl)vinyl]thiophene (5.00 g, 19.4 mmol) was added slowly at −78° C., the mixture was allowed to warm to 20-25° C., and stirred at that temperature for 16 h. Then the mixture was poured into $H_2O$ (20 mL), the aqueous phase was extracted with EtOAc (3×50 mL), and the combined organic extracts were washed with NaCl solution (sat. aq., 1×50 mL), dried over $Na_2SO_4$, filtered, and concentrated. Purification by column chromatography ($SiO_2$, EtOAc/petroleum ether=15:85) afforded 5-(4-bromo-2-thienyl)-N,N-bis[(4-methoxyphenyl)methyl]-5-(trifluoromethyl)-4H-isoxazol-3-amine (4.90 g, 46%) as yellow solid.

$^1$H-NMR (400 MHz, $CDCl_3$, RT): δ 7.30 (s, 1H), 7.08 (d, J=8.6 Hz, 5H), 6.91-6.81 (m, 4H), 4.25 (s, 4H), 3.82 (s, 6H), 3.78 (d, J=16.0 Hz, 1H), 3.44 (d, J=16.0 Hz, 1H).

Step 5: A mixture of 5-(4-bromo-2-thienyl)-N,N-bis[(4-methoxyphenyl)methyl]-5-(trifluoromethyl)-4H-isoxazol-3-amine (2.25 g, 4.05 mmol) in $F_3CCO_2H$ (15 mL) was stirred at 50° C. for 16 h. Then the mixture was quenched with $NaHCO_3$ solution (sat. aq., 100 mL), the aqueous phase was extracted with EtOAc (3×30 mL), and the combined organic extracts were washed with NaCl solution (sat. aq., 1×30 mL), dried over $Na_2SO_4$, filtered, and concentrated. Purification by column chromatography (EtOAc/petroleum ether=36:74) afforded 5-(4-bromo-2-thienyl)-5-(trifluoromethyl)-4H-isoxazol-3-amine (1.10 g, 86%) as yellow oil.

$^1$H-NMR (400 MHz, $CDCl_3$, RT): δ 7.30 (d, J=1.4 Hz, 1H), 7.11 (s, 1H), 3.72 (d, J=16.3 Hz, 1H), 3.40-3.33 (m, 1H).

This product could then be transformed further into e.g. the compound I-175, analogously to the above examples.

Example 30: Synthesis of N,N-bis[(4-methoxyphenyl)methyl]-5-(trifluoromethyl)-5-[4-(trifluoromethyl)-2-thienyl]-4H-isoxazol-3-amine Step 1: To a mixture of 5-(4-bromo-2-thienyl)-N,N-bis[(4-methoxyphenyl)methyl]-5-(trifluoromethyl)-4H-isoxazol-3-amine (6.30 g, 11.3 mmol, synthesized as described above) and trans-N,N'-dimethyl-1,2-cyclohexanediamine (161 mg, 1.13 mmol) in 1,4-dioxane (60 mL) was added CuI (108 mg, 0.56 mmol) and NaI (3.4 g, 22.7 mmol) at 20° C. and purged with $N_2$ for 3 min. The vial was sealed, and the mixture stirred at 120° C. for 16 h. Then the mixture was filtered through diatomite, and the filter cake was washed with EtOAc (200 mL). The filtrate was mixed with $H_2O$ (50 mL), the aqueous phase was extracted with EtOAc (3×50 mL), and the combined organic extracts were washed with NaCl solution (sat. aq., 1×50 mL), dried over $Na_2SO_4$, filtered, and concentrated. Purification by column chromatography (EtOAc in PE=15%) afforded 5-(4-iodo-2-thienyl)-N,N-bis[(4-methoxyphenyl)methyl]-5-(trifluoromethyl)-4H-isoxazol-3-amine (5.90 g, 87%) as a yellow solid.

$^1$H-NMR (400 MHz, $CDCl_3$, RT): δ 7.46 (d, J=1.1 Hz, 1H), 7.12 (s, 1H), 7.07 (d, J=8.5 Hz, 4H), 6.86 (d, J=8.6 Hz, 4H), 4.25 (s, 4H), 3.82 (s, 6H), 3.78 (d, J=16.0 Hz, 1H), 3.45 (d, J=16.0 Hz, 1H).

Step 2: To a mixture of 5-(4-iodo-2-thienyl)-N,N-bis[(4-methoxyphenyl)methyl]-5-(trifluoromethyl)-4H-isoxazol-3-amine (5.90 g, 9.80 mmol) in NMP (60 mL) was added CuI (5.60 g, 29.4 mmol) at 20-25° C. and purged with $N_2$ for 3 min, before methyl 2,2-difluoro-2-(fluorosulfonyl)acetate (9.4 g, 49 mmol) was added. The vial was sealed, and the reaction mixture stirred at 130° C. for 1 h. Then the mixture was filtered, and the filter cake was washed with EtOAc (200 mL). The filtrate was mixed with $H_2O$ (100 mL), the aqueous phase was extracted with EtOAc (3×80 mL), and the combined organic extracts washed with NaCl solution (sat. aq., 1×100 mL), dried over $Na_2SO_4$, filtered, and concentrated. Purification by column chromatography (EtOAc in PE=19%) afforded N,N-bis[(4-methoxyphenyl)methyl]-5-(trifluoromethyl)-5-[4-(trifluoromethyl)-2-thienyl]-4H-isoxazol-3-amine (4.00 g, 75%) as a yellow solid.

$^1$H-NMR (400 MHz, $CDCl_3$, RT): δ 7.80-7.76 (m, 1H), 7.14-7.02 (m, 5H), 6.90-6.81 (m, 4H), 4.29-4.24 (m, 4H), 3.84-3.78 (m, 7H), 3.51-3.42 (m, 1H).

This product could then be transformed further into e.g. the compound I-177, analogously to the above examples.

Example 31: Synthesis of 1-[2-(ethoxymethyl)-5-(trifluoromethyl)pyrazol-3-yl]-2,2,2-trifluoro-ethanone Step 1: To a solution of 3-(trifluoromethyl)-1H-pyrazole (50.0 g, 367 mmol) in THF (500 mL) at 0° C. was added NaH (11.5 g, 286 mmol), and the mixture was stirred at that temperature for an additional 0.5 h. Then, chloromethoxyethane (42 g, 441 mmol) was added, and the reaction was stirred at 0° C. for 2 h. The mixture was quenched with $H_2O$ (200 mL), the aqueous phase was extracted with EtOAc (3×200 mL), and the combined organic phases were washed with NaCl solution (sat. aq., 1×100 mL), dried over $Na_2SO_4$, filtered, and concentrated. Purification by column chromatography (MTBE in petroleum ether=3%) afforded 1-(ethoxymethyl)-3-(trifluoromethyl)pyrazole (22.0 g, 31%) as a yellow oil.

$^1$H-NMR (400 MHz, $CDCl_3$, RT): δ 7.64 (s, 1H), 6.61 (d, J=2.4 Hz, 1H), 5.49 (s, 2H), 3.56 (q, J=7.0 Hz, 2H), 1.19 (t, J=7.0 Hz, 3H).

Step 2: To a solution of n-BuLi (2.5M in THF, 21.0 mL, 54.1 mmol) at −78° C. was carefully added 1-(ethoxymethyl)-3-(trifluoromethyl)pyrazole (7.00 g, 36.1 mmol) in THF (20 mL), and the mixture was stirred at that temperature for 0.5 h. Then, 2,2,2-trifluoro-N-methoxy-N-methyl-acetamide (16.8 g, 108 mmol) was added at −78° C. and the reaction was stirred at that temperature for 4 h. Then the mixture was quenched with $H_2O$ (100 mL), the aqueous phase was extracted with EtOAc (3×100 mL), and the combined organic extracts were washed with NaCl solution (sat. aq., 1×10 mL), dried over $Na_2SO_4$, filtered, and concentrated. Purification by column chromatography (EtOAc in petroleum ether=31%) afforded (4.90 g, 47%) as a yellow oil.

$^1$H-NMR (400 MHz, $CDCl_3$, RT): δ 7.37 (d, J=1.4 Hz, 1H), 5.91 (s, 2H), 3.63-3.57 (m, 2H), 1.18 (t, J=7.0 Hz, 3H).

This product could then be transformed further into e.g. the compound I-178, analogously to the above examples.

Example 32: Synthesis of 3-chloro-5-(trifluoromethylsulfanyl)benzaldehyde

Step 1: To a solution of 4-(trifluoromethylsulfanyl)aniline (25.0 g, 129 mmol) in DMF (250 mL) at 20-25° C. was added N-bromosuccinimide (23.0 g, 129 mmol) in portions, and the resulting reaction mixture was stirred at that temperature for 16 h. Then the mixture was poured into $H_2O$ (100 mL), the aqueous phase was extracted with EtOAc (2×200 mL), and the combined organic extracts were washed with $H_2O$ (100 mL) and NaCl solution (sat. aq., 2×50 mL), dried over $Na_2SO_4$, filtered, and concentrated. Purification by column chromatography (petroleum ether/EtOAc=10:1) afforded 2-bromo-4-(trifluoromethylsulfanyl)aniline (24.5 g, 70%) as a brown solid.

$^1$H-NMR (400 MHz, $CDCl_3$, RT): δ 7.71 (d, J=1.8 Hz, 1H) 7.38 (dd, J=8.4, 1.8 Hz, 1H) 6.76 (d, J=8.3 Hz, 1H) 4.21-4.71 (m, 2H).

Step 2: To a solution of 2-bromo-4-(trifluoromethylsulfanyl)aniline (30.0 g, 144 mmol) in DMF (300 mL) at 20-25° C. was added N-chlorosuccinimide (29.6 g, 221 mmol) in portions, and the reaction mixture was stirred at that temperature for 16 h. Then the mixture was poured into $H_2O$ (200 mL), the aqueous phase was extracted with EtOAc (2×200 mL), the combined organic extracts were washed with $H_2O$ (100 mL) and NaCl solution (sat. aq., 2×80 mL), dried over $Na_2SO_4$, filtered, and concentrated. Purification by column chromatography (petroleum ether/EtOAc=10:1) to give 2-bromo-6-chloro-4-(trifluoromethylsulfanyl)aniline (26.0 g, 88%) as a brown solid.

$^1$H NMR (400 MHz, $CDCl_3$, RT): δ 7.65 (d, J=1.9 Hz, 1H) 7.53 (d, J=1.9 Hz, 1H) 4.86 (br s, 2H).

Step 3: To a solution of 2-bromo-6-chloro-4-(trifluoromethylsulfanyl)aniline (20.0 g, 65.6 mmol) in DMF (250 mL) at 0° C. was added ONOtBu (8.00 g, 78.8 mmol), and the reaction mixture was then stirred at 20-25° C. for 16 h. Then the mixture was poured into $H_2O$ (100 mL), the aqueous phase was extracted with EtOAc (2×200 mL), and the combined organic extracts were washed with $H_2O$ (1×80 mL) and NaCl solution (sat. aq., 2×60 mL), dried over $Na_2SO_4$, filtered, and concentrated. Purification by column chromatography (petroleum ether/EtOAc=10:1) afforded 1-bromo-3-chloro-5-(trifluoromethylsulfanyl)benzene (14.0 g, 74%) as a brown oil.

$^1$H-NMR (400 MHz, $CDCl_3$, RT): δ ppm 7.71 (s, 1H) 7.63-7.67 (m, 1H) 7.60 (d, J=1.5 Hz, 1H).

Step 4: To a solution of 1-bromo-3-chloro-5-(trifluoromethylsulfanyl)benzene (10.0 g, 34.3 mmol) in DMF (120 mL) at 20-25° C. was added $Et_3N$(10 g, 0.10 mol), Pd(dppf)$Cl_2$ (1.22 g, 1.70 mmol), and $HSiEt_3$ (7.95 g, 68.5 mmol), before the reaction mixture was stirred at 50° C. under CO gas (50 Psi) for 1 h. Then the reaction mixture was poured into water (100 mL), the aqueous phase was extracted with EtOAc (3×100 mL), and the combined organic extracts were washed with NaCl solution (sat. aq., 3×50 mL), dried over $Na_2SO_4$, filtered, and concentrated. Purification by column chromatography (petroleum ether/EtOAc=10:1) afforded 3-chloro-5-(trifluoromethylsulfanyl)benzaldehyde (3.0 g, 36%) as a colourless oil.

$^1$H-NMR (400 MHz, $CDCl_3$, RT): δ 10.0 (s, 1H) 8.04 (s, 1H) 7.98 (s, 1H) 7.90 (s, 1H).

This product could then be transformed further into e.g. the compound I-165, analogously to the above examples.

Example 33: Chiral Separation of N-(3-bromo-2-fluoro-phenyl)-5-(3,5-dichlorophenyl)-5-(trifluoromethyl)-4H-isoxazol-3-amine into the corresponding (S)- and (R)-enantiomer Step 1: N-(3-bromo-2-fluoro-phenyl)-5-(3,5-dichlorophenyl)-5-(trifluoromethyl)-4H-isoxazol-3-amine (6.00 g, 20.1 mmol) was separated by chiral SFC (column: DAICEL CHIRALPAK IC (250 mm×30 mm, 10 μm); mobile phase: [0.1% $NH_3H_2O$ MeOH]; B %: 23%-23%, 2.8 min) to give:

(5S)-5-(3,5-dichlorophenyl)-5-(trifluoromethyl)-4H-isoxazol-3-amine (2.58 g, 43%) as a white solid. $^1$H NMR (400 MHz, $CDCl_3$, RT): δ 7.45 (s, 2H), 7.39-7.43 (m, 1H), 4.06 (s, 2H), 3.71 (d, J=16.4 Hz, 1H), 3.34 (d, J=16.8 Hz, 1H); Analytical SFC (CHIRALPAK IC-3 100 mm×4.6 mm I.D. 3 μm, $CO_2$/MeOH (0.05% DEA), 3.4 mL·min$^{-1}$, 1800 psi, 35° C., gradient from 5% to 40% in 2 min and hold 40% for 1 min then from 40% to 5% of B for 1 min): $t_R$=1.64 min, er=99.5:0.5. This product could then be transformed further into e.g. the compounds I-137, I-140, I-145, I-146, I-147, and I-174, analogously to the above examples;

and (5R)-5-(3,5-dichlorophenyl)-5-(trifluoromethyl)-4H-isoxazol-3-amine (2.56 g, 43%) as a white solid. $^1$H-NMR (400 MHz, $CDCl_3$, RT): δ 7.45 (s, 2H), 7.39-7.43 (m, 1H), 4.05 (s, 2H), 3.71 (d, J=16.2 Hz, 1H), 3.34 (d, J=16.4 Hz, 1H); Analytical SFC (CHIRALPAK IC-3 100 mm×4.6 mm I.D. 3 μm, $CO_2$/MeOH (0.05% DEA), 3.4 mL·min$^{-1}$, 1800 psi, 35° C., gradient from 5% to 40% in 2 min and hold 40% for 1 min then from 40% to 5% of B for 1 min): $t_R$=1.44 min, er>99.5:0.5. This product could then be transformed further into e.g. the compounds I-136, I-139, I-141, I-143, and I-144, analogously to the above examples.

Example 34: Synthesis of 2-bromo-5-[[5-(3,5-dichlorophenyl)-5-(trifluoromethyl)-4H-isoxazol-3-yl]-methyl-amino]benzoic acid Step 1: To a solution of 5-(3,5-dichlorophenyl)-5-(trifluoromethyl)-4H-isoxazol-3-amine (662 mg, 2.21 mmol, synthesized as described in the above examples) in 1,4-dioxane (20 mL) at 20-25° C. under an atmosphere of $N_2$ was added methyl 2-bromo-5-iodo-benzoate (830 mg, 2.43 mmol), $Cs_2CO_3$ (1.45 g, 4.42 mmol), $Pd_2(dba)_3$ (200 mg, 0.22 mmol), and Xantphos (256 mg, 0.44 mmol). The resulting reaction mixture was heated to 80° C. and stirred at that temperature for 16 h. Then the reaction mixture was filtered, the filtrate was concentrated, and the residue was purified by column chromatography ($SiO_2$, petroleum ether/EtOAc=100:0 to 92:8) to give methyl 2-bromo-5-[[5-(3,5-dichlorophenyl)-5-(trifluoromethyl)-4H-isoxazol-3-yl]amino]benzoate (900 mg, 80%) as a yellow solid.

$^1$H-NMR (400 MHz, $CDCl_3$, RT): δ 7.81 (d, J=2.8 Hz, 1H), 7.58 (d, J=8.8 Hz, 1H), 7.48 (s, 2H), 7.45-7.40 (m, 2H), 6.12 (s, 1H), 3.94 (s, 3H), 3.90 (d, J=16.1 Hz, 1H), 3.53 (d, J=16.3 Hz, 1H).

Step 2: To the solution of methyl 2-bromo-5-[[5-(3,5-dichlorophenyl)-5-(trifluoromethyl)-4H-isoxazol-3-yl]amino]benzoate (800 mg, 1.57 mmol) in DMF (10 mL) at 0° C. was added NaH (75 mg, 1.88 mmol) in portions, and the resulting mixture was stirred at that temperature for 0.5 h. MeI (268 mg, 1.88 mmol) was added to the reaction mixture and the reaction was stirred for 3 h at 20-25° C. The reaction mixture was quenched with $H_2O$ (20 mL), the aqueous phase was extracted with EtOAc (3×10 mL), and the combined organic extracts were washed with NaCl solution (sat. aq., 1×20 mL), dried over $Na_2SO_4$, filtered, and concentrated to afford crude methyl 2-bromo-5-[[5-(3,5-dichlorophenyl)-5-(trifluoromethyl)-4H-isoxazol-3-yl]-methyl-amino]benzoate (850 mg, 92%) as a yellow solid.

Step 3: To a solution of methyl 2-bromo-5-[[5-(3,5-dichlorophenyl)-5-(trifluoromethyl)-4H-isoxazol-3-yl]-methyl-amino]benzoate (800 mg, 1.53 mmol) in THF (10 mL) and $H_2O$ (3.0 mL) at 20-25° C. was added LiOH·$H_2O$ (96 mg, 2.3 mmol), and the reaction was stirred at that temperature for 48 h. The reaction solution was adjusted to pH=4 with HCl solution (1N in $H_2O$), the aqueous phase was extracted with EtOAc (3×20 mL), and the combined organic extracts were dried over $Na_2SO_4$, filtered, and concentrated to give 2-bromo-5-[[5-(3,5-dichlorophenyl)-5-(trifluoromethyl)-4H-isoxazol-3-yl]-methyl-amino]benzoic acid (700 mg, 90%) as a yellow solid.

$^1$H-NMR (400 MHz, DMSO-d6, RT): δ 14.1-13.0 (m, 1H), 7.76 (t, J=1.9 Hz, 1H), 7.72-7.67 (m, 2H), 7.59 (d, J=1.5 Hz, 2H), 7.42 (dd, J=2.7, 8.7 Hz, 1H), 3.97-3.76 (m, 2H), 3.23 (s, 3H).

This product could then be transformed further into e.g. the compound I-148, analogously as described in the above examples.

Example 35: Synthesis of 2-chloro-N-(1-cyanocyclopropyl)-5-[[5-(3,5-dichlorophenyl)-5-(trifluoromethyl)-4H-isoxazol-3-yl]sulfanyl]benzamide [II-2]

Step 1: To a solution of 3-bromo-4-chloro-benzenethiol (11.8 g, 49.3 mmol), and 1,1-dibromoformaldoxime (5.00 g, 24.7 mmol) in THF (240 mL) at 0° C. was added NaH (60 wt % in mineral oil, 1.97 g, 49.3 mmol) in portions, and the resulting mixture was stirred at that temperature for 1 h. Then the reaction mixture was quenched with ice-water (200 mL), the aqueous phase was extracted with EtOAc (3×50 mL), and the combined organic extracts were washed with NaCl solution (sat. aq., 1×50 mL), dried over $Na_2SO_4$, filtered, and concentrated. Purification by column chromatography (petroleum ether/EtOAc=99:1 to 85:15) afforded bis[(3-bromo-4-chloro-phenyl)sulfanyl]methanone oxime (2.40 g, 20%) as a light yellow solid.

$^1$H-NMR (400 MHz, DMSO-d6, RT): δ=12.7 (s, 1H), 7.58 (d, J=8.3 Hz, 1H), 7.54 (d, J=8.4 Hz, 1H), 7.51 (d, J=2.1 Hz, 1H), 7.44 (dd, J=2.1, 8.3 Hz, 1H), 7.27 (d, J=2.1 Hz, 1H), 7.13 (dd, J=2.2, 8.4 Hz, 1H).

Step 2: To a solution of bis[(3-bromo-4-chloro-phenyl)sulfanyl]methanone oxime (400 mg, 0.82 mmol), and 1,3-dichloro-5-[1-(trifluoromethyl)vinyl]benzene (474 mg, 1.97 mmol) in THF (10 mL) were added $AgNO_3$ (209 mg, 0.82 mmol) and $K_2CO_3$ (113 mg, 0.82 mmol), and the resulting mixture was stirred at 50° C. for 15 h. Then the reaction mixture was filtered, the filtrate was concentrated, and the residue purified by column chromatography (petroleum ether/EtOAc=99:1 to 90:10; gradient) to afford 3-(3-bromo-4-chloro-phenyl)sulfanyl-5-(3,5-dichlorophenyl)-5-(trifluoromethyl)-4H-isoxazole (75 mg, 18%) as a light-yellow oil.

$^1$H-NMR (400 MHz, $CDCl_3$, RT): δ 7.82 (d, J=2.0 Hz, 1H), 7.54-7.47 (m, 1H), 7.47-7.41 (m, 2H), 7.39 (d, J=1.1 Hz, 2H), 3.75 (d, J=17.3 Hz, 1H), 3.38 (d, J=17.3 Hz, 1H).

Step 3: To a solution of 3-(3-bromo-4-chloro-phenyl)sulfanyl-5-(3,5-dichlorophenyl)-5-(trifluoromethyl)-4H-isoxazole (200 mg, 0.396 mmol) in THF (5 mL) at 0° C. under an atmosphere of $N_2$ was added iPrMgCl·LiCl (1.3M, 0.609 mL, 0.791 mmol) dropwise. The mixture was stirred at that temperature for 0.5 h, before $CO_2$ (dry ice, 2.0 g) was added, and the mixture was allowed to gradually warm to 20-25° C. Stirring was continued at 20-25° C. for 1 h, before the reaction mixture was poured into HCl solution (0.5N in $H_2O$, 10 mL), the aqueous phase was extracted with EtOAc (3×20 mL), and the combined organic extracts were dried over $Na_2SO_4$, filtered, and concentrated. Purification by preparative HPLC (TFA) afforded 2-chloro-5-[[5-(3,5-dichlorophenyl)-5-(trifluoromethyl)-4H-isoxazol-3-yl]sulfanyl]benzoic acid (150 mg, 80%) as a white solid.

$^1$H-NMR (400 MHz, DMSO-d6, RT) δ=7.77 (t, J=1.7 Hz, 1H), 7.68 (brs, 1H), 7.55 (d, J=1.1 Hz, 2H), 7.51-7.40 (m, 2H), 3.92 (br d, J=2.3 Hz, 2H).

Step 4: To a solution of 2-chloro-5-[[5-(3,5-dichlorophenyl)-5-(trifluoromethyl)-4H-isoxazol-3-yl]sulfanyl]benzoic acid (300 mg, 0.637 mmol) in MeCN (6.0 mL) at 20-25° C. was added NMI (157 mg, 1.91 mmol), and TCFH (215 mg, 0.765 mmol), and the mixture was stirred at that temperature for 0.5 h. Then 1-aminocyclopropanecarbonitrile (90.7 mg, 0.765 mmol) was added, and the reaction mixture was stirred at 20-25° C. for 15 h. Then the reaction mixture was poured into $H_2O$ (50 mL), the aqueous phase was extracted with EtOAc (3×20 mL), and the combined organic extracts were washed with NaCl solution (sat. aq., 1×10 mL), dried over $Na_2SO_4$, filtered, and concentrated. Purification by column chromatography (petroleum ether/EtOAc=99:1 to 50:50) afforded 2-chloro-N-(1-cyanocyclopropyl)-5-[[5-(3,5-dichlorophenyl)-5-(trifluoromethyl)-4H-isoxazol-3-yl]sulfanyl]benzamide [II-2] (120 mg, 32%) as a white solid.

$^1$H-NMR (400 MHz, DMSO-d6, RT): δ 9.47 (s, 1H), 7.80 (t, J=1.8 Hz, 1H), 7.73 (s, 1H), 7.72-7.68 (m, 1H), 7.66-7.62 (m, 1H), 7.55 (d, J=1.6 Hz, 2H), 3.97 (s, 2H), 3.31 (br s, 2H), 1.57 (br d, J=2.8 Hz, 2H), 1.27 (br d, J=2.6 Hz, 2H).

Example 36: Synthesis of 2-chloro-N-(1-cyanocyclopropyl)-5-[[5-(3,5-dichlorophenyl)-5-(trifluoromethyl)-4H-isoxazol-3-yl]sulfonyl]benzamide [II-3]

Step 1: To a solution of 2-chloro-N-(1-cyanocyclopropyl)-5-[[5-(3,5-dichlorophenyl)-5-(trifluoromethyl)-4H-isoxazol-3-yl]sulfanyl]benzamide [II-2] (220 mg, 0.411 mmol, synthesized as described in the examples above) in THF (4.0 mL) at 0° C. was added meta-chloroperoxybenzoic acid (85 wt %, 418 mg, 2.06 mmol) in portions, and the resulting mixture was stirred at 20-25° C. for 15 h. Then the reaction mixture was poured into a solution of 20 mL $NaHCO_3$ (sat. aq.) and $Na_2SO_3$ (sat. aq.), the aqueous phase was extracted with EtOAc (3×20 mL), and the combined organic extracts were washed with NaCl solution (sat. aq., 1×10 mL), dried over $Na_2SO_4$, filtered, and concentrated. Purification by column chromatography (petroleum ether/EtOAc=99:1 to 50:50) afforded Synthesis of 2-chloro-N-(1-cyanocyclopropyl)-5-[[5-(3,5-dichlorophenyl)-5-(trifluoromethyl)-4H-isoxazol-3-yl]sulfonyl]benzamide [II-3] (145 mg, 62%) as a colourless syrup.

$^1$H-NMR (400 MHz, Methanol-d4, RT): δ 8.12-8.10 (m, 1H), 8.10-8.07 (m, 1H), 7.84 (d, J=9.3 Hz, 1H), 7.63-7.55 (m, 1H), 7.51 (d, J=1.4 Hz, 2H), 4.27 (d, J=18.6 Hz, 1H), 4.01 (d, J=18.6 Hz, 1H), 1.64-1.56 (m, 2H), 1.44-1.35 (m, 2H).

Example 37: Synthesis of 2-chloro-5-[[5-(3,5-dichloro-4-fluoro-phenyl)-5-(trifluoromethyl)-4H-isoxazol-3-yl]oxy]-N-(3,5-difluoro-2-pyridyl)benzamide [II-8]

Step 1: To a solution of 1,3-dichloro-2-fluoro-5-[1-(trifluoromethyl)vinyl]benzene (16.0 g, 61.8 mmol, synthesized as described in the examples above), and 1,1-dibromoformaldoxime (15.0 g, 74.1 mmol) in EtOAc (160 mL) was added $NaHCO_3$ (51.9 g, 617 mmol) in portions, and the resulting mixture was stirred at 50° C. for 15 h. Then the reaction mixture was poured into $H_2O$ (100 mL), the aqueous phase was extracted with EtOAc (3×100 mL), and the combined organic extracts were washed with NaCl solution (sat. aq., 1×100 mL), dried over $Na_2SO_4$, filtered, and concentrated. Purification by column chromatography (petroleum ether/EtOAc=99:1 to 90:10) afforded 3-bromo-5-(3,5-dichloro-4-fluoro-phenyl)-5-(trifluoromethyl)-4H-isoxazole (16.5 g, 70%) as a yellow solid.

$^1$H-NMR (400 MHz, $CDCl_3$, RT): δ 7.49 (d, J=5.9 Hz, 2H), 3.93 (d, J=17.8 Hz, 1H), 3.56 (dd, J=0.8, 17.8 Hz, 1H).

Step 2: To a solution of 2-chloro-5-hydroxy-benzoic acid (1.09 g, 6.30 mmol) in N-methyl-2-pyrrolidone (20 mL) at 20-25° C. was added NaOH (504 mg, 12.6 mmol) and pyridine (15 mL), and the mixture was then stirred at 90° C. for 20 min. Then, 3-bromo-5-(3,5-dichloro-4-fluoro-phenyl)-5-(trifluoromethyl)-4H-isoxazole (2.0 g, 5.25 mmol) was added. After TLC-analysis (petroleum ether/EtOAc=5:1) showed that the reaction was complete, the mixture was poured into $H_2O$ (100 mL), and the water adjusted to pH=4 with 2.0 M aq. HCl. The aqueous phase was extracted with EtOAc (3×30 mL), and the combined organic extracts were washed with NaCl solution (sat. aq., 1×10 mL), dried over $Na_2SO_4$, filtered, and concentrated to give 2-chloro-5-[[5-(3,5-dichloro-4-fluoro-phenyl)-5-(trifluoromethyl)-4H-isoxazol-3-yl]oxy]benzoic acid (2.7 g, crude) as black oil, which was used directly in the next step without further purification.

Step 3: A solution of 2-chloro-5-[[5-(3,5-dichloro-4-fluoro-phenyl)-5-(trifluoromethyl)-4H-isoxazol-3-yl]oxy]benzoic acid (580 mg, 1.23 mmol) in $SOCl_2$ (6.0 mL, excess) was stirred at 60° C. for 3 h. The mixture was concentrated, dissolved in $CH_2Cl_2$ (6.0 mL), and added into a solution of 3,5-difluoropyridin-2-amine (604 mg, 1.23 mmol) in pyridine (12.0 mL) and $CH_2Cl_2$ (12 mL) dropwise at 0° C. After the addition, the mixture was stirred at 25° C. for 15 h. The mixture was poured into HCl solution (1.0 M in $H_2O$, 50 mL), the aqueous phase was extracted with $CH_2Cl_2$ (3×30 mL), and the combined organic extracts were washed with NaCl solution (sat. aq., 1×30 mL), dried over $Na_2SO_4$, filtered, and concentrated. Purification by column chromatography (petroleum ether/EtOAc=99:1 to 90:10) afforded 2-chloro-5-[[5-(3,5-dichloro-4-fluoro-phenyl)-5-(trifluoromethyl)-4H-isoxazol-3-yl]oxy]-N-(3,5-difluoro-2-pyridyl)benzamide [II-8] (280 mg, 39%) as a light-yellow oil.

$^1$H-NMR (400 MHz, methanol-d4, RT): δ ppm 8.24 (br s, 1H) 7.71-7.77 (m, 1H) 7.71 (s, 2H) 7.57 (br d, J=9.03 Hz, 2H) 7.46 (dd, J=8.91, 2.76 Hz, 1H) 4.01-4.19 (m, 1H) 3.84-3.95 (m, 1H).

Example 38: Synthesis of methyl 3-chloro-5-[[5-(3,5-dichlorophenyl)-5-(trifluoromethyl)-4H-isoxazol-3-yl]-ethyl-amino]thiophene-2-carboxylate Step 1: To a solution of 3-chlorothiophene-2-carboxylic acid (2.00 g, 12.3 mmol) in THF (30 mL) at −60° C. under an atmosphere of $N_2$ was added LiN(i-Pr)$_2$ (2.0 M in THF/heptane/ethylbenzene, 15.4 mL, 30.9 mmol) dropwise, and the mixture was stirred at that temperature for 1 h. Then, a solution of 1,2-Dibromo-1,1,2,2-tetrafluoroethane (6.24 g, 24.7 mmol) in THF (2.0 mL) was added dropwise to the above reaction mixture and stirring was continued for another 1 h. Then the reaction mixture was poured into HCl solution (1.0 N in $H_2O$, 20 mL), the aqueous phase was extracted with EtOAc (3×50 mL), and the combined organic extracts were dried over $Na_2SO_4$, filtered, and concentrated to give crude 5-bromo-3-chloro-thiophene-2-carboxylic acid (2.5 g, 86%) as a yellow solid.

$^1$H-NMR (400 MHz, DMSO-d6, RT): δ 7.47 (s, 1H), 3.07 (s, 1H).

Step 2: 5-bromo-3-chloro-thiophene-2-carboxylic acid (2.2 g, 9.2 mmol) was dissolved in HCl/MeOH (20 mL), and the solution was stirred at 65° C. for 16 h. Then the reaction mixture was concentrated under reduced pressure, quenched with $NaHCO_3$ solution (sat. aq., 50 mL), the aqueous phase was extracted with EtOAc (3×50 mL), and the combined organic extracts were washed with NaCl solution (sat. aq., 1×10 mL), dried over $Na_2SO_4$ filtered, and concentrated. Purification by column chromatography ($SiO_2$, petroleum ether/EtOAc=100:0 to 94:6) afforded methyl 5-bromo-3-chloro-thiophene-2-carboxylate (700 mg, 30%).

$^1H$-NMR (400 MHz, $CDCl_3$, RT): δ 7.04-7.01 (m, 1H), 3.89 (s, 3H).

Step 3: To a solution of methyl 5-bromo-3-chloro-thiophene-2-carboxylate (700 mg, 2.75 mmol) in 1,4-dioxane (8.0 mL) at 20-25° C. under an atmosphere of $N_2$ was added 5-(3,5-dichlorophenyl)-5-(trifluoromethyl)-4H-isoxazol-3-amine (746 mg, 2.5 mmol), $Cs_2CO_3$ (1.63 mg, 5.00 mmol), $Pd_2(dba)_3$ (229 mg, 0.25 mmol), and Xantphos (289 mg, 0.500 mmol), and the resulting mixture was then stirred at 80° C. for 16 h. Then the reaction mixture was filtered, the filtrate concentrated, and the residue purified by column chromatography ($SiO_2$, petroleum ether/EtOAc=100:0 to 84:16) to give methyl 3-chloro-5-[[5-(3,5-dichlorophenyl)-5-(trifluoromethyl)-4H-isoxazol-3-yl]amino]thiophene-2-carboxylate (1.3 g, 70%) as a white solid.

$^1H$-NMR (400 MHz, $CDCl_3$, RT): δ 7.81 (s, 1H), 7.46 (s, 2H), 7.42 (s, 1H), 7.27 (s, 1H), 6.63 (s, 1H), 3.96-3.88 (m, 2H), 3.85 (s, 3H), 3.61-3.52 (m, 1H).

Step 4: To a solution of methyl 3-chloro-5-[[5-(3,5-dichlorophenyl)-5-(trifluoromethyl)-4H-isoxazol-3-yl]amino]thiophene-2-carboxylate (800 mg, 1.69 mmol) in THF (8.0 mL) at 0° C. was added t-BuOK (285 mg, 2.54 mmol) in portions, and the mixture was stirred at that temperature for 0.5 h. Then, EtOTf (360 mg, 2.03 mmol) was added dropwise, and the reaction mixture was stirred at 20-25° C. for 16 h. Then the reaction mixture was quenched with $H_2O$ (20 mL), the aqueous phase was extracted with EtOAc (3×20 mL), and the combined organic extracts were washed with NaCl solution (sat. aq., 1×20 mL), dried over $Na_2SO_4$ filtered, and concentrated. Purification by column chromatography ($SiO_2$, petroleum ether/EtOAc=100:0 to 83:17) afforded the title methyl 3-chloro-5-[[5-(3,5-dichlorophenyl)-5-(trifluoromethyl)-4H-isoxazol-3-yl]-ethyl-amino]thiophene-2-carboxylate (400 mg, 46%) as a yellow solid.

$^1H$-NMR (400 MHz, $CDCl_3$, RT): δ 8.17 (br s, 1H), 8.01 (br d, J=8.6 Hz, 2H), 7.75-7.44 (m, 2H), 7.32 (br d, J=8.4 Hz, 2H), 7.23 (br d, J=8.3 Hz, 2H), 6.94-6.61 (m, 1H), 5.86 (d, J=17.6 Hz, 1H), 5.40 (d, J=10.9 Hz, 1H), 2.97 (s, 1H), 2.89 (s, 1H), 2.20 (s, 3H), 2.05 (s, 4H).

This product could then be transformed further into e.g. the compound I-156, analogously as described in the above examples.

Example 39: Synthesis of ethyl 2-[5-[[5-(3,5-dichloro-4-fluoro-phenyl)-5-(trifluoromethyl)-4H-isoxazol-3-yl]amino]-2-methyl-phenyl]-2,2-difluoro-acetate Step 1: To a solution of 5-(3,5-dichloro-4-fluoro-phenyl)-5-(trifluoromethyl)-4H-isoxazol-3-amine (400 mg, 1.26 mmol) in 1,4-dioxane (10 mL) at 20-25° C. under an atmosphere of Ar was added ethyl 2-(5-bromo-2-methylphenyl)-2,2-difluoroacetate (370 mg, 1.26 mmol), $K_2CO_3$ (523 mg, 3.78 mmol), $Pd_2(dba)_3$ (58 mg, 0.063 mmol), and Xantphos (88 mg, 0.15 mmol), and the resulting mixture was stirred at reflux temperature for 16 h. Then the reaction mixture was quenched with $NH_4Cl$ solution (sat. aq., 15 mL), the aqueous phase was extracted with EtOAc (3×30 mL), and the combined organic extracts were washed with NaCl solution (sat. aq., 1×15 mL), dried over $Na_2SO_4$ filtered, and concentrated. Purification by column chromatography (cyclohexane/EtOAc=100:0 to 60:40) afforded the title ethyl 2-[5-[[5-(3,5-dichloro-4-fluoro-phenyl)-5-(trifluoromethyl)-4H-isoxazol-3-yl]amino]-2-methyl-phenyl]-2,2-difluoro-acetate (267 mg, 40%).

HPLC-MS (method A): retention time=1.483 min, m/z=529 ([M+H]$^+$).

This product could then be transformed further into e.g. the compounds III-3, and III-4, analogously to the above examples.

TABLE I.1 compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-1 | W-9 | $CF_3$ | H | G1, $R^{41}$: Cl, $R^{42}$: H | c-$C_3H_5$ | H | 1.308, 494.0 | A |
| I-2 | W-9 | $CF_3$ | H | G1, $R^{41}$: Cl, $R^{42}$: H | 2,4-$F_2$—$C_6H_3$ | H | 1.430, 566.0 | A |
| I-3 | W-9 | $CF_3$ | H | G1, $R^{41}$: Cl, $R^{42}$: H | (1-CN)-c-$C_3H_4$ | H | 1.292, 517.0 | A |
| I-4 | W-9 | $CF_3$ | H | G1, $R^{41}$: Cl, $R^{42}$: H | 3-$NH_2$,2,4-$F_2$—$C_6H_2$ | H | 1.328, 580.6 | A |
| I-5 | W-9 | $CF_3$ | H | G1, $R^{41}$: Cl, $R^{42}$: H | 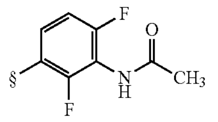 | H | 1.275, 623.0 | A |
| I-6 | W-9 | $CF_3$ | H | G1, $R^{41}$: Cl, $R^{42}$: H | 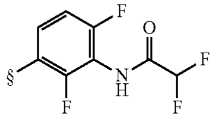 | H | 1.324, 656.9 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-7 | W-9 | $CF_3$ | H | G1, $R^{41}$: Cl, $R^{42}$: H | 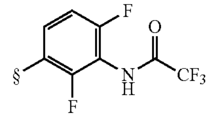 | H | 1.375, 674.9 | A |
| I-8 | W-9 | $CF_3$ | H | G1, $R^{41}$: Cl, $R^{42}$: H | 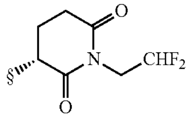 | H | 1.290, 628.0 | A |
| I-9 | W-9 | $CF_3$ | H | G1, $R^{41}$: Cl, $R^{42}$: H | 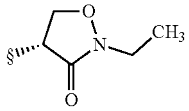 | H | 1.265, 564.8 | A |
| I-10 | W-9 | $CF_3$ | H | G1, $R^{41}$: Cl, $R^{42}$: H | 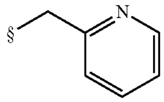 | H | 1.073, 543.0 | A |
| I-11 | W-9 | $CF_3$ | H | G1, $R^{41}$: Cl, $R^{42}$: H | $CH_2CF_3$ | H | 1.309, 533.7 | A |
| I-12 | W-9 | $CF_3$ | H | G1, $R^{41}$: Cl, $R^{42}$: H | $CH_2C(=O)NHCH_2CF_3$ | H | 1.274, 593.0 | A |
| I-13 | W-9 | $CF_3$ | H | G1, $R^{41}$: Cl, $R^{42}$: H | 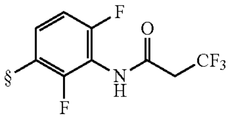 | H | 1.341, 690.9 | A |
| I-14 | W-9 | $CF_3$ | H | G1, $R^{41}$: Cl, $R^{42}$: H | 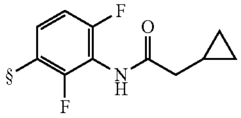 | H | 1.347, 663.0 | A |
| I-15 | W-9 | $CF_3$ | H | G1, $R^{41}$: Cl, $R^{42}$: H | 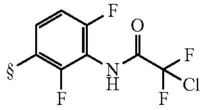 | H | 1.386, 692.9 | A |
| I-16 | W-9 | $CF_3$ | H | 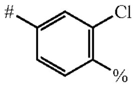 | 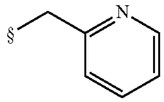 | H | 1.084, 543.0 | A |
| I-17 | W-9 | $CF_3$ | H | 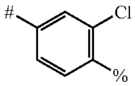 | 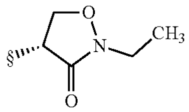 | H | 1.257, 567.0 | A |
| I-18 | W-9 | $CF_3$ | H | G1, $R^{41}$: H, $R^{42}$: Cl | 2,4-$F_2$—$C_6H_3$ | H | 1.407, 563.7 | A |
| I-19 | W-9 | $CF_3$ | H | G1, $R^{41}$: Cl, $R^{42}$: H | $CH_2C(=O)$ $NH(CH_2)_2CF_3$ | H | 1.268, 604.7 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-20 | W-9 | $CF_3$ | H | G1, $R^{41}$: Cl, $R^{42}$: H | 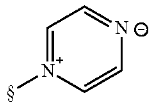 | | 1.179, 531.6 | A |
| I-21 | W-8 | $CF_3$ | H | G1, $R^{41}$: Cl, $R^{42}$: H | 2,4-$F_2$—$C_6H_3$ | H | 1.322, 548.0 | A |
| I-22 | W-9 | $CF_3$ | H | G1, $R^{41}$: Cl, $R^{42}$: H | 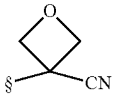 | H | 1.250, 535.0 | A |
| I-23 | W-9 | $CF_3$ | H | G1, $R^{41}$: Cl, $R^{42}$: H | (1-CN)-c-$C_4H_6$ | H | 1.308, 530.8 | A |
| I-24 | W-11 | $CF_3$ | H | G1, $R^{41}$: Cl, $R^{42}$: H | 2,4-$F_2$—$C_6H_3$ | H | 1.397, 583.9 | A |
| I-25 | W-9 | $CF_3$ | $CH_3$ | G1, $R^{41}$: Cl, $R^{42}$: H | 2,4-$F_2$—$C_6H_3$ | H | 1.405, 578.0 | A |
| I-26 | W-9 | $CF_3$ | H | G1, $R^{41}$: Cl, $R^{42}$: H | 6-F-pyrid-3-yl | H | 1.330, 548.6 | A |
| I-27 | W-11 | $CF_3$ | H | G1, $R^{41}$: Cl, $R^{42}$: H | (1-CN)-c-$C_3H_4$ | H | 1.276, 534.7 | A |
| I-28 | W-9 | $CF_3$ | $CH_3$ | G1, $R^{41}$: Cl, $R^{42}$: H | (1-CN)-c-$C_3H_4$ | H | 1.279, 532.6 | A |
| I-29 | W-11 | $CF_3$ | H | G1, $R^{41}$: Cl, $R^{42}$: H | $CH_2CN$ | H | 1.248, 510.5 | A |
| I-30 | W-9 | $CF_3$ | H | G1, $R^{41}$: F, $R^{42}$: F | (1-CN)-c-$C_3H_4$ | H | 1.270, 518.8 | A |
| I-31 | W-8 | $CF_3$ | H | G1, $R^{41}$: Cl, $R^{42}$: H | (3,3-$F_2$)-c-$C_4H_5$ | H | 1.277, 525.7 | A |
| I-32 | W-26 | $CF_3$ | H | G1, $R^{41}$: Cl, $R^{42}$: H | 2,4-$F_2$—$C_6H_3$ | H | 1.357, 582.0 | A |
| I-33 | W-8 | $CF_3$ | H | G1, $R^{41}$: Cl, $R^{42}$: H | (1-$CF_2H$)-c-$C_3H_4$ | H | 1.267, 525.7 | A |
| I-34 | W-11 | $CF_3$ | H | G1, $R^{41}$: Cl, $R^{42}$: H | 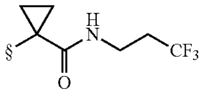 | H | 1.286, 651.0 | A |
| I-35 | W-11 | $CF_3$ | H | G1, $R^{41}$: Cl, $R^{42}$: H | 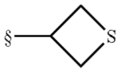 | H | 1.326, 542.1 | A |
| I-36 | W-11 | $CF_3$ | H | G1, $R^{41}$: Cl, $R^{42}$: H | 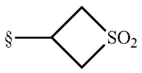 | H | 1.219, 576.1 | A |
| I-37 | W-11 | $CF_3$ | H | G1, $R^{41}$: Cl, $R^{42}$: H | $C(CH_3)_2CH_2SO_2CH_3$ | H | 1.274, 605.5 | A |
| I-38 | W-18 | $CF_3$ | H | G1, $R^{41}$: Cl, $R^{42}$: H | 2,4-$F_2$—$C_6H_3$ | H | 1.330, 564.0 | A |
| I-39 | W-26 | $CF_3$ | H | G1, $R^{41}$: Cl, $R^{42}$: H | (1-CN)-c-$C_3H_4$ | H | 1.216, 535.0 | A |
| I-40 | W-18 | $CF_3$ | H | G1, $R^{41}$: Cl, $R^{42}$: H | (1-CN)-c-$C_3H_4$ | H | 1.198, 517.0 | A |
| I-41 | W-11 | $CF_3$ | H | G1, $R^{41}$: Cl, $R^{42}$: H | 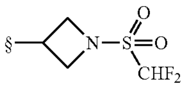 | H | 1.304, 641.1 | A |
| I-42 | W-11 | $CF_3$ | H | G1, $R^{41}$: Cl, $R^{42}$: H | 4-F—$C_6H_4$ | $CH_3$ | 1.403, 579.9 | A |
| I-43 | W-8 | $CF_3$ | H | G1, $R^{41}$: Cl, $R^{42}$: H | (1-$CF_3$)-c-$C_3H_4$ | H | 1.293, 543.9 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-44 | W-8 | $CF_3$ | H | G1, $R^{41}$: Cl, $R^{42}$: H | 2-$CH_3$,4-CF$(CF_3)_2$—$C_6H_3$ | H | 1.501, 694.0 | A |
| I-45 | W-8 | $CF_3$ | H | G1, $R^{41}$: Cl, $R^{42}$: H | 2-F,4-$CF_3$—$C_6H_3$ | H | 1.446, 598.1 | A |
| I-46 | W-9 | $CF_3$ | H | G1, $R^{41}$: Cl, $R^{42}$: H | (1-CN)-c-$C_3H_4$ | $CH_2$-c-$C_3H_5$ | 1.396, 572.9 | A |
| I-47 | W-9 | $CF_3$ | $CH_2$-c-$C_3H_5$ | G1, $R^{41}$: Cl, $R^{42}$: H | (1-CN)-c-$C_3H_4$ | $CH_2$-c-$C_3H_5$ | 1.474, 627.0 | A |
| I-48 | W-9 | $CF_3$ | H | G1, $R^{41}$: H, $R^{42}$: F | 2,4-$F_2$—$C_6H_3$ | H | 1.416, 548.0 | A |
| I-49 | W-8 | $CF_3$ | H | G1, $R^{41}$: Cl, $R^{42}$: H | 4-CN,2-F—$C_6H_3$ | H | 1.331, 554.9 | A |
| I-50 | W-8 | $CF_3$ | H | G1, $R^{41}$: Cl, $R^{42}$: H | 2,6-$F_2$-pyrid-3-yl | H | 1.309, 548.9 | A |
| I-51 | W-11 | $CF_3$ | H | G1, $R^{41}$: Cl, $R^{42}$: H | 6-F-pyridazin-3-yl | H | 1.319, 568.0 | A |
| I-52 | W-11 | $CF_3$ | H | G1, $R^{41}$: Cl, $R^{42}$: H | 2-CN,4-F—$C_6H_3$ | H | 1.368, 591.1 | A |
| I-53 | W-8 | $CF_3$ | H | G1, $R^{41}$: Cl, $R^{42}$: H | 2-Br,4-$CF_3$—$C_6H_3$ | H | 1.497, 659.8 | A |
| I-54 | W-8 | $CF_3$ | H | G1, $R^{41}$: Cl, $R^{42}$: H | (1-$CF_3$)-c-$C_4H_6$ | H | 1.335, 557.9 | A |
| I-55 | W-9 | $CF_3$ | $CH_2$—C≡N | G1, $R^{41}$: Cl, $R^{42}$: H | (1-CN)-c-$C_3H_4$ | H | 1.270, 558.2 | A |
| I-56 | W-8 | $CF_3$ | H | G1, $R^{41}$: Cl, $R^{42}$: H | 4-F,2-$CF_3$—$C_6H_3$ | H | 1.370, 598.0 | A |
| I-57 | W-11 | $CF_3$ | H | G1, $R^{41}$: Cl, $R^{42}$: H | 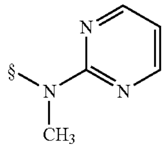 | H | 1.266, 576.9 | A |
| I-58 | W-11 | $CF_3$ | H | G1, $R^{41}$: Cl, $R^{42}$: H | $C(CH_3)_2CN$ | H | 1.295, 538.9 | A |
| I-59 | W-9 | $CF_3$ | H | G1, $R^{41}$: H, $R^{42}$: F | (1-CN)-c-$C_3H_4$ | H | 1.280, 500.9 | A |
| I-60 | W-9 | $CF_3$ | $CH_2$-c-$C_3H_5$ | G1, $R^{41}$: Cl, $R^{42}$: H | (1-CN)-c-$C_3H_4$ | H | 1.363, 571.0 | A |
| I-61 | W-11 | $CF_3$ | H | G1, $R^{41}$: Cl, $R^{42}$: H | 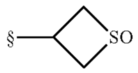 | H | 1.167, 559.9 | A |
| I-62 | W-11 | $CF_3$ | H | G1, $R^{41}$: Cl, $R^{42}$: H | 4-F-pyrid-3-yl | H | 1.205, 566.9 | A |
| I-63 | W-11 | $CF_3$ | H | G1, $R^{41}$: Cl, $R^{42}$: H | 3,5-$F_2$-pyrid-2-yl | H | 1.313, 584.9 | A |
| I-64 | W-9 | $CF_3$ | H | G1, $R^{41}$: $CH_3$, $R^{42}$: H | 2,4-$F_2$—$C_6H_3$ | H | 1.418, 544.0 | A |
| I-65 | W-9 | $CF_3$ | H | G1, $R^{41}$: $OCHF_2$, $R^{42}$: H | $CH_2CF_3$ | H | 1.372, 565.9 | A |
| I-66 | W-9 | $CF_3$ | H | G1, $R^{41}$: $CF_3$, $R^{42}$: H | 2,4-$F_2$—$C_6H_3$ | H | 1.441, 598.0 | A |
| I-67 | W-9 | $CF_3$ | H | G1, $R^{41}$: $OCHF_2$, $R^{42}$: H | c-$C_3H_5$ | H | 1.337, 524.0 | A |
| I-68 | W-9 | $CF_3$ | H | G1, $R^{41}$: $CH_3$, $R^{42}$: H | c-$C_3H_5$ | H | 1.288, 472.0 | A |
| I-69 | W-9 | $CF_3$ | H | G1, $R^{41}$: $CH_3$, $R^{42}$: H | $CH_2CF_3$ | H | 1.347, 514.0 | A |
| I-70 | W-9 | $CF_3$ | H | G1, $R^{41}$: $OCF_3$, $R^{42}$: H | 2,4-$F_2$—$C_6H_3$ | H | 1.482, 614.0 | A |
| I-71 | W-9 | $CF_3$ | H | G1, $R^{41}$: $OCF_3$, $R^{42}$: H | $CH_2CF_3$ | H | 1.403, 584.0 | A |
| I-72 | W-9 | $CF_3$ | H | G1, $R^{41}$: $OCF_3$, $R^{42}$: H | c-$C_3H_5$ | H | 1.373, 542.0 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-73 | W-9 | $CF_3$ | H | G2, $R^{41}$: Cl, $R^{42}$: H | 2,4-$F_2$—$C_6H_3$ | H | 1.381, 564.9 | A |
| I-74 | W-9 | $CF_3$ | H | G1, $R^{41}$: $OCHF_2$, $R^{42}$: H | 2,4-$F_2$—$C_6H_3$ | H | 1.470, 596.0 | A |
| I-75 | W-9 | $CF_3$ | H | G1, $R^{41}$: F, $R^{42}$: H | 2,4-$F_2$—$C_6H_3$ | H | 1.457, 548.0 | A |
| I-76 | W-11 | $CF_3$ | H | G1, $R^{41}$: Cl, $R^{42}$: H | 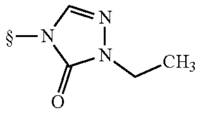 | H | 1.232, 582.9 | A |
| I-77 | W-11 | $CF_3$ | H | G1, $R^{41}$: Cl, $R^{42}$: H | 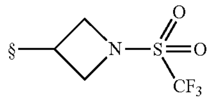 | H | 1.365, 558.5 | A |
| I-78 | W-9 | $CF_3$ | H | G1, $R^{41}$: F, $R^{42}$: H | (1-CN)-c-$C_3H_4$ | H | 1.290, 500.9 | A |
| I-79 | W-9 | $CF_3$ | H | G1, $R^{41}$: $CF_3$, $R^{42}$: H | (1-CN)-c-$C_3H_4$ | H | 1.326, 551.0 | A |
| I-80 | W-9 | $CF_3$ | H | G3, $R^{41}$: Cl | $CH_2CF_3$ | H | 1.282, 534.9 | A |
| I-81 | W-9 | $CF_3$ | H | G2, $R^{41}$: Cl, $R^{42}$: H | (1-CN)-c-$C_3H_4$ | H | 1.245, 517.9 | A |
| I-82 | W-9 | $CF_3$ | H | G1, $R^{41}$: H, $R^{42}$: CN | 2,4-$F_2$—$C_6H_3$ | H | 1.542, 555.0 | A |
| I-83 | W-9 | $CF_3$ | H | G3, $R^{42}$: Cl | (1-CN)-c-$C_3H_4$ | H | 1.218, 519.9 | A |
| I-84 | W-9 | $CF_3$ | H | G2, $R^{41}$: Cl, $R^{42}$: H | $CH_2CF_3$ | H | 1.301, 536.9 | A |
| I-85 | W-9 | $CF_3$ | H | G2, $R^{41}$: Cl, $R^{42}$: H | c-$C_3H_5$ | H | 1.242, 494.9 | A |
| I-86 | W-9 | $CF_3$ | H | G1, $R^{41}$: H, $R^{42}$: CN | $CH_2CF_3$ | H | 1.488, 524.9 | A |
| I-87 | W-9 | $CF_3$ | H | G1, $R^{41}$: $OCF_3$, $R^{42}$: H | (1-CN)-c-$C_3H_4$ | H | 1.346, 566.9 | A |
| I-88 | W-9 | $CF_3$ | H | G1, $R^{41}$: $OCH_3$, $R^{42}$: H | 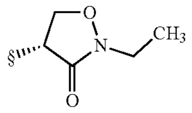 | H | 1.302, 561.0 | A |
| I-89 | W-9 | $CF_3$ | H | G1, $R^{41}$: $OCH_3$, $R^{42}$: H | c-$C_3H_5$ | H | 1.326, 488.0 | A |
| I-90 | W-9 | $CF_3$ | H | G1, $R^{41}$: $OCH_3$, $R^{42}$: H | (1-CN)-c-$C_3H_4$ | H | 1.298, 513.0 | A |
| I-91 | W-9 | $CF_3$ | H | G1, $R^{41}$: $OCH_3$, $R^{42}$: H | 2,4-$F_2$—$C_6H_3$ | H | 1.495, 559.9 | A |
| I-92 | W-9 | $CF_3$ | H | G1, $R^{41}$: $OCH_3$, $R^{42}$: H | $CH_2CF_3$ | H | 1.367, 530.0 | A |
| I-93 | W-9 | $CF_3$ | H | G1, $R^{41}$: H, $R^{42}$: CN | (1-CN)-c-$C_3H_4$ | H | 1.454, 508.0 | A |
| I-94 | W-9 | $CF_3$ | H | G1, $R^{41}$: H, $R^{42}$: CN | c-$C_3H_5$ | H | 1.486, 483.0 | A |
| I-95 | W-9 | $CF_3$ | H | G1, $R^{41}$: $OCHF_2$, $R^{42}$: H | (1-CN)-c-$C_3H_4$ | H | 1.312, 549.0 | A |
| I-96 | W-9 | $CF_3$ | H | G3, $R^{42}$: Cl | c-$C_3H_5$ | H | 1.226, 492.9 | A |
| I-97 | W-11 | $CF_3$ | H | G1, $R^{41}$: Cl, $R^{42}$: H | (1-CN)-c-$C_3H_4$ | $CH_3$ | 1.319, 549.3 | A |
| I-98 | W-11 | $CF_3$ | H | G1, $R^{41}$: Cl, $R^{42}$: H | 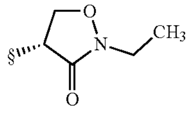 | H | 1.260, 583.2 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-99 | W-11 | $CF_3$ | H | G1, $R^{41}$: Cl, $R^{42}$: H | $C_6H_5$ | $C_2H_5$ | 1.427, 576.2 | A |
| I-100 | W-9 | $CF_3$ | $C(=O)OC_2H_5$ | G1, $R^{41}$: Cl, $R^{42}$: H | (1-CN)-c-$C_3H_4$ | C(O) $OC_2H_5$ | 1.466, 662.9 | A |
| I-101 | W-11 | $CF_3$ | H | G1, $R^{41}$: Cl, $R^{42}$: H | 4-F—$C_6H_4$ | $C_2H_5$ | 1.428, 594.3 | A |
| I-102 | W-9 | $CF_3$ | H | G1, $R^{41}$: $CH_3$, $R^{42}$: H | 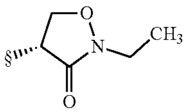 | H | 1.249, 545.3 | A |
| I-103 | W-9 | $CF_3$ | H | G1, $R^{41}$: $OCF_3$, $R^{42}$: H | 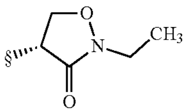 | H | 1.323, 615.3 | A |
| I-104 | W-9 | $CF_3$ | H | G1, $R^{41}$: F, $R^{42}$: H | 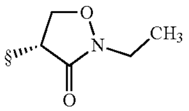 | H | 1.261, 549.3 | A |
| I-105 | W-9 | $CF_3$ | H | G1, $R^{41}$: $OCHF_2$, $R^{42}$: H | 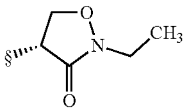 | H | 1.285, 597.3 | A |
| I-106 | W-9 | $CF_3$ | H | G2, $R^{41}$: Cl, $R^{42}$: H | 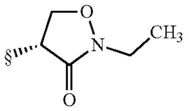 | H | 1.210, 566.2 | A |
| I-107 | W-9 | $CF_3$ | H | G1, $R^{41}$: $CF_3$, $R^{42}$: H | 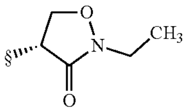 | H | 1.300, 599.3 | A |
| I-108 | W-9 | $CF_3$ | $CH_2OCH_3$ | G1, $R^{41}$: Cl, $R^{42}$: H | (1-CN)-c-$C_3H_4$ | H | 1.274, 528.9 | A |
| I-109 | W-8 | $CF_3$ | H | G1, $R^{41}$: Cl, $R^{42}$: H | 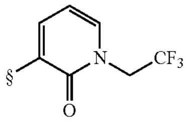 | H | 1.335, 611.3 | A |
| I-110 | W-11 | $CF_3$ | $CH_3$ | G1, $R^{41}$: Cl, $R^{42}$: H | 4-F—$C_6H_4$ | $CH_3$ | 1.418, 592.3 | A |
| I-111 | W-9 | $CF_3$ | $C(=O)OC_2H_5$ | G1, $R^{41}$: Cl, $R^{42}$: H | (1-CN)-c-$C_3H_4$ | H | 1.354, 589.0 | A |
| I-112 | W-8 | $CF_3$ | H | G1, $R^{41}$: Cl, $R^{42}$: H | 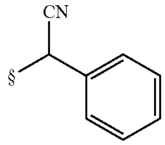 | H | 1.316, 551.1 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-113 | W-8 | $CF_3$ | H | G1, $R^{41}$: Cl, $R^{42}$: H | 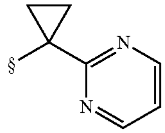 | H | 1.234, 553.9 | A |
| I-114 | W-11 | $CF_3$ | H | G1, $R^{41}$: Cl, $R^{42}$: H | 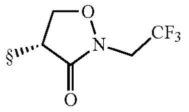 | H | 1.303, 637.3 | A |
| I-115 | W-11 | $CF_3$ | $CH_3$ | G1, $R^{41}$: Cl, $R^{42}$: H | (1-CN)-c-$C_3H_4$ | H | 1.274, 549.2 | A |
| I-116 | W-11 | $CF_3$ | $CH_3$ | G1, $R^{41}$: Cl, $R^{42}$: H | 2,4-$F_2$—$C_6H_3$ | H | 1.409, 598.3 | A |
| I-117 | W-11 | $CF_3$ | $CH_3$ | G1, $R^{41}$: Cl, $R^{42}$: H | $C_6H_5$ | $C_2H_5$ | 1.462, 590.3 | A |
| I-118 | W-9 | $CF_3$ | $CH_2$—$CH(OC_2H_5)_2$ | G1, $R^{41}$: Cl, $R^{42}$: H | (1-CN)-c-$C_3H_4$ | H | 1.375, 587.3 | A |
| I-119 | W-11 | $CF_3$ | $CH_3$ | G1, $R^{41}$: Cl, $R^{42}$: H | 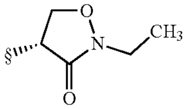 | H | 1.268, 597.3 | A |
| I-120 | W-11 | $CF_3$ | $CH_3$ | G1, $R^{41}$: Cl, $R^{42}$: H | (1-CN)-c-$C_3H_4$ | $CH_3$ | 1.331, 565.3 | A |
| I-121 | W-9 | $CF_3$ | $CH_3$ | G1, $R^{41}$: Cl, $R^{42}$: H | 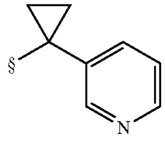 | H | 1.074, 585.3 | A |
| I-122 | W-8 | $CF_3$ | H | G1, $R^{41}$: Cl, $R^{42}$: H | 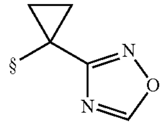 | H | 1.235, 546.0 | A |
| I-123 | W-9 | $CF_3$ | $CH_3$ | G1, $R^{41}$: Cl, $R^{42}$: H | 3-CN-4-F—$C_6H_3$ | H | 1.401, 584.9 | A |
| I-124 | W-9 | $CF_3$ | $CH_3$ | G1, $R^{41}$: Cl, $R^{42}$: H | 4-CN-pyrid-2-yl | H | 1.386, 567.9 | A |
| I-125 | W-9 | $CF_3$ | $CH_3$ | G1, $R^{41}$: Cl, $R^{42}$: H | 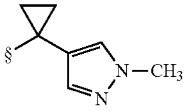 | H | 1.260, 588.0 | A |
| I-126 | W-9 | $CF_3$ | $CH_3$ | G1, $R^{41}$: Cl, $R^{42}$: H | 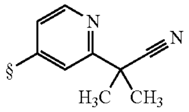 | H | 1.382, 610.0 | A |
| I-127 | W-9 | $CF_3$ | $CH_3$ | G1, $R^{41}$: Cl, $R^{42}$: H | 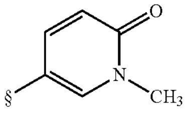 | H | 1.198, 574.9 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-128 | W-9 | $CF_3$ | $CH_3$ | G1, $R^{41}$: Cl, $R^{42}$: H | 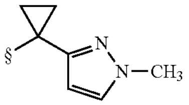 | H | 1.283, 587.9 | A |
| I-129 | W-9 | $CF_3$ | $CH_3$ | G1, $R^{41}$: Cl, $R^{42}$: H | 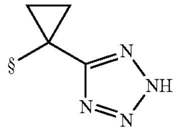 | H | 1.204, 575.9 | A |
| I-130 | W-9 | $CF_3$ | $CH_3$ | G1, $R^{41}$: Cl, $R^{42}$: H | 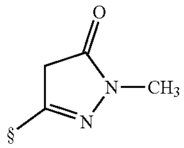 | H | 1.204, 563.9 | A |
| I-131 | W-9 | $CF_2Cl$ | H | G1, $R^{41}$: Cl, $R^{42}$: H | 2,4-$F_2$—$C_6H_3$ | H | 1.417, 580.2 | A |
| I-132 | W-20 | $CF_3$ | H | G1, $R^{41}$: Cl, $R^{42}$: H | (1-CN)-c-$C_3H_4$ | H | 1.278, 551.3 | A |
| I-133 | W-21 | $CF_3$ | H | G1, $R^{41}$: Cl, $R^{42}$: H | (1-CN)-c-$C_3H_4$ | H | 1.288, 597.2 | A |
| I-134 | W-9 | $CF_3$ | $CH_3$ | G1, $R^{41}$: Cl, $R^{42}$: H | 4-Cl-pyrid-2-yl | H | 1.471, 578.9 | A |
| I-135 | W-9 | $CF_3$ | $CH_3$ | G1, $R^{41}$: Cl, $R^{42}$: H | 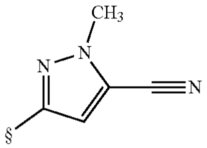 | H | 1.327, 573.3 | A |
| I-136 | W-9 <R> | $CF_3$ | H | G1, $R^{41}$: Cl, $R^{42}$: H | 2,4-$F_2$—$C_6H_3$ | H | 1.423, 564.0 | A |
| I-137 | W-9 <S> | $CF_3$ | H | G1, $R^{41}$: Cl, $R^{42}$: H | 2,4-$F_2$—$C_6H_3$ | H | 1.430, 565.8 | A |
| I-138 | W-9 | $CF_3$ | $CH_3$ | G1, $R^{41}$: Cl, $R^{42}$: H | 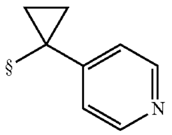 | H | 1.066, 582.9 | A |
| I-139 | W-9 <R> | $CF_3$ | H | G1, $R^{41}$: Cl, $R^{42}$: H | (1-CN)-c-$C_3H_4$ | H | 1.290, 516.9 | A |
| I-140 | W-9 <S> | $CF_3$ | H | G1, $R^{41}$: Cl, $R^{42}$: H | (1-CN)-c-$C_3H_4$ | H | 1.291, 518.9 | A |
| I-141 | W-9 <R> | $CF_3$ | H | G1, $R^{41}$: Cl, $R^{42}$: H | 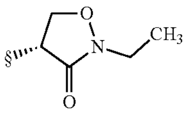 | H | 1.291, 566.9 | A |
| I-142 | W-9 | $CF_3$ | $CH_3$ | G1, $R^{41}$: Cl, $R^{42}$: H | 3-F-pyrid-4-yl | H | 1.248, 560.9 | A |
| I-143 | W-9 <R> | $CF_3$ | $CH_3$ | G1, $R^{41}$: Cl, $R^{42}$: H | (1-CN)-c-$C_3H_4$ | H | 1.322, 532.8 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-144 | W-9 <R> | $CF_3$ | $CH_3$ | G1, $R^{41}$: Cl, $R^{42}$: H | 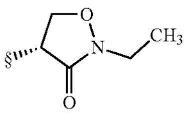 | H | 1.293, 578.9 | A |
| I-145 | W-9 <S> | $CF_3$ | H | G1, $R^{41}$: Cl, $R^{42}$: H | 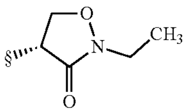 | H | 1.324, 564.9 | A |
| I-146 | W-9 <S> | $CF_3$ | $CH_3$ | G1, $R^{41}$: Cl, $R^{42}$: H | (1-CN)-c-$C_3H_4$ | H | 1.300, 532.9 | A |
| I-147 | W-9 <S> | $CF_3$ | $CH_3$ | G1, $R^{41}$: Cl, $R^{42}$: H | 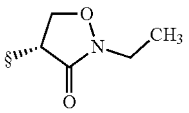 | H | 1.295, 580.9 | A |
| I-148 | W-9 | $CF_3$ | $CH_3$ | G1, $R^{41}$: Br, $R^{42}$: H | (1-CN)-c-$C_3H_4$ | H | 1.285, 577.2 | A |
| I-149 | W-9 | $CF_3$ | H | G1, $R^{41}$: Cl, $R^{42}$: H | 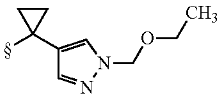 | H | 1.313, 617.9 | A |
| I-150 | W-11 | $CF_3$ | H | G1, $R^{41}$: $CH_3$, $R^{42}$: H | 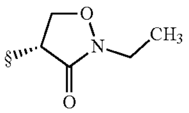 | H | 1.278, 562.9 | A |
| I-151 | W-32 | $CF_3$ | H | G1, $R^{41}$: Cl, $R^{42}$: H | (1-CN)-c-$C_3H_4$ | H | 1.321, 566.9 | A |
| I-152 | W-9 | $CF_3$ | H | G1, $R^{41}$: Cl, $R^{42}$: H | 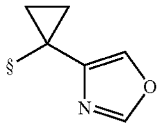 | H | 1.301, 558.9 | A |
| I-153 | W-9 | $CF_3$ | H | G1, $R^{41}$: Cl, $R^{42}$: H | 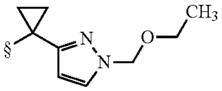 | H | 1.349, 615.9 | A |
| I-154 | W-11 | $CF_3$ | $C_2H_5$ | G1, $R^{41}$: $CH_3$, $R^{42}$: H | 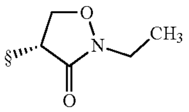 | H | 1.327, 591.4 | A |
| I-155 | W-11 | $CF_3$ | H | G1, $R^{41}$: Cl, $R^{42}$: H | 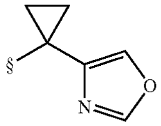 | H | 1.323, 576.9 | A |
| I-156 | W-9 | $CF_3$ | $C_2H_5$ | 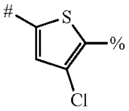 | (1-CN)-c-$C_3H_4$ | H | 1.410, 552.8 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-157 | W-9 | $CF_3$ | 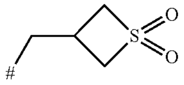 | G1, $R^{41}$: Cl, $R^{42}$: H | (1-CN)-c-$C_3H_4$ | H | 1.221, 637.4 | A |
| I-158 | W-9 | $CF_3$ | 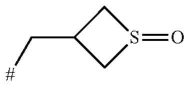 | G1, $R^{41}$: Cl, $R^{42}$: H | (1-CN)-c-$C_3H_4$ | H | 1.170, 620.0 | A |
| I-159 | W-9 | $CF_3$ | 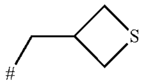 | G1, $R^{41}$: Cl, $R^{42}$: H | (1-CN)-c-$C_3H_4$ | H | 1.339, 605.3 | A |
| I-160 | W-9 | $CF_3$ | 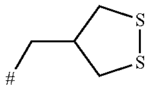 | G1, $R^{41}$: Cl, $R^{42}$: H | (1-CN)-c-$C_3H_4$ | H | 1.383, 637.3 | A |
| I-161 | W-9 | $CF_3$ | H | G1, $R^{41}$: Cl, $R^{42}$: H | 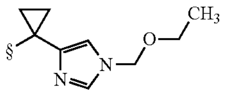 | H | 1.076, 616.4 | A |
| I-162 | W-9 | $CF_3$ | H | G1, $R^{41}$: Cl, $R^{42}$: H | 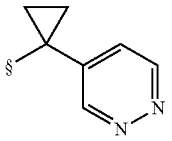 | H | 1.135, 570.3 | A |
| I-163 | W-9 | $CF_3$ | H | G1, $R^{41}$: Cl, $R^{42}$: H | 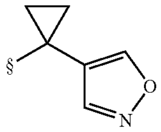 | H | 1.300, 559.3 | A |
| I-164 | W-11 | $CF_3$ | H | G1, $R^{41}$: Cl, $R^{42}$: H | 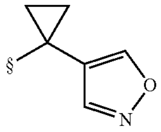 | H | 1.311, 579.3 | A |
| I-165 | W-33 | $CF_3$ | H | G1, $R^{41}$: Cl, $R^{42}$: H | (1-CN)-c-$C_3H_4$ | H | 1.336, 583.3 | A |
| I-166 | W-11 | $CF_3$ | $CH_2OCH_3$ | G1, $R^{41}$: $CH_3$, $R^{42}$: H | 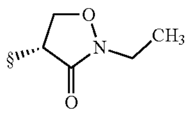 | H | 1.270, 575.4 | A |
| I-167 | W-9 | $CF_3$ | H | G1, $R^{41}$: $OCF_3$, $R^{42}$: H | 3,5-$F_2$-pyrid-2-yl | H | 1.350, 615.4 | A |
| I-168 | W-9 | $CF_3$ | H | G1, $R^{41}$: $CH_3$, $R^{42}$: H | 3,5-$F_2$-pyrid-2-yl | H | 1.302, 544.9 | A |
| I-169 | W-9 | $CF_3$ | H | G1, $R^{41}$: $CH_3$, $R^{42}$: H | 5-F-pyrid-2-yl | H | 1.351, 527.3 | A |
| I-170 | 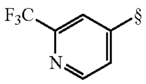 | $CF_3$ | H | G1, $R^{41}$: Cl, $R^{42}$: H | (1-CN)-c-$C_3H_4$ | H | 1.126, 517.9 | A |
| I-171 | W-11 | $CF_3$ | H | G4, $R^{42}$: H | 3,5-$F_2$-pyrid-2-yl | H | 1.323, 549.9 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-172 | W-11 | $CF_3$ | H | G4, $R^{42}$: H | c-$C_3H_5$ | H | 1.176, 478.7 | A |
| I-173 | 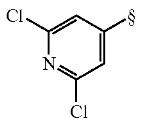 | $CF_3$ | H | G1, $R^{41}$: Cl, $R^{42}$: H | (1-CN)-c-$C_3H_4$ | H | 1.197, 519.8 | A |
| I-174 | W-9 <S> | $CF_3$ | H | G1, $R^{41}$: Cl, $R^{42}$: H | 3,5-$F_2$-pyrid-2-yl | H | 1.303, 566.6 | A |
| I-175 | 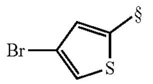 | $CF_3$ | H | G1, $R^{41}$: Cl, $R^{42}$: H | (1-CN)-c-$C_3H_4$ | H | 1.188, 535.0 | A |
| I-176 | W-11 | $CF_3$ | H | G1, $R^{41}$: Cl, $R^{42}$: H | 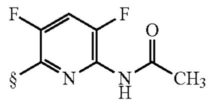 | H | 1.251, 642.1 | A |
| I-177 | 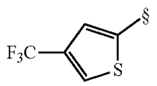 | $CF_3$ | H | G1, $R^{41}$: Cl, $R^{42}$: H | (1-CN)-c-$C_3H_4$ | H | 1.221, 523.1 | A |
| I-178 | 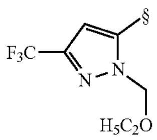 | $CF_3$ | H | G1, $R^{41}$: Cl, $R^{42}$: H | (1-CN)-c-$C_3H_4$ | H | 1.194, 564.9 | A |
| I-179 | W-8 | $CF_3$ | H | G1, $R^{41}$: Cl, $R^{42}$: H | 3,5-$F_2$-pyrid-2-yl | H | 1.239, 548.8 | A |
| I-180 | W-11 | $CF_3$ | $C_2H_5$ | G1, $R^{41}$: Cl, $R^{42}$: H | 5-Cl-pyrid-2-yl | H | 1.520, 609.1 | A |
| I-181 | W-11 | $CF_3$ | $CH_2OCH_3$ | G1, $R^{41}$: Cl, $R^{42}$: H | 5-CN-pyrid-2-yl | H | 1.411, 618.2 | A |
| I-182 | W-11 | $CF_3$ | $C_2H_5$ | G1, $R^{41}$: Cl, $R^{42}$: H | 5-F-pyrimidin-2-yl | H | 1.354, 596.1 | A |
| I-183 | W-11 | $CF_3$ | $C_2H_5$ | G1, $R^{41}$: Cl, $R^{42}$: H | 5-F-pyrid-2-yl | H | 1.470, 595.2 | A |
| I-184 | W-11 | $CF_3$ | $C_2H_5$ | G1, $R^{41}$: $CH_3$, $R^{42}$: H | 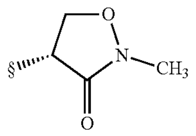 | H | 1.298, 577.2 | A |
| I-185 | W-11 | $CF_3$ | $C_2H_5$ | G1, $R^{41}$: $CH_3$, $R^{42}$: H | 3-F-pyrid-2-yl | H | 1.363, 573.2 | A |
| I-186 | W-11 | $CF_3$ | $C_2H_5$ | G1, $R^{41}$: Cl, $R^{42}$: H | 5-CN-pyrid-2-yl | H | 1.442, 600.2 | A |
| I-187 | W-11 | $CF_3$ | $C_2H_5$ | G1, $R^{41}$: $CH_3$, $R^{42}$: H | 5-CN-pyrid-2-yl | H | 1.445, 580.2 | A |
| I-188 | W-11 | $CF_3$ | $CH_2OCH_3$ | G1, $R^{41}$: Cl, $R^{42}$: H | 5-F-pyrid-2-yl | H | 1.433, 611.1 | A |
| I-189 | W-11 | $CF_3$ | $C_2H_5$ | G1, $R^{41}$: Cl, $R^{42}$: H | (1-CN)-c-$C_3H_4$ | H | 1.352, 563.1 | A |
| I-190 | W-11 | $CF_3$ | $C_2H_5$ | G1, $R^{41}$: Cl, $R^{42}$: H | 2-pyrid-2-yl | $CH_3$ | 1.428, 591.2 | A |
| I-191 | W-11 | $CF_3$ | $C_2H_5$ | G1, $R^{41}$: Cl, $R^{42}$: H | 3-F-pyrid-2-yl | H | 1.367, 595.2 | A |
| I-192 | W-11 | $CF_3$ | $C_2H_5$ | G1, $R^{41}$: Cl, $R^{42}$: H | pyrid-2-yl | H | 1.372, 577.1 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-193 | W-11 | $CF_3$ | $C_2H_5$ | G1, $R^{41}$: $CH_3$, $R^{42}$: H | pyrid-2-yl | H | 1.302, 555.2 | A |
| I-194 | W-11 | $CF_3$ | $C_2H_5$ | G1, $R^{41}$: $CH_3$, $R^{42}$: H | 5-F-pyrid-2-yl | H | 1.473, 573.2 | A |
| I-195 | W-11 | $CF_3$ | $CH_2OCH_3$ | G1, $R^{41}$: Cl, $R^{42}$: H | pyrid-2-yl | $CH_3$ | 1.396, 605.1 | A |
| I-196 | W-11 | $CF_3$ | $CH_2OCH_3$ | G1, $R^{41}$: Cl, $R^{42}$: H | 5-Cl-pyrid-2-yl | H | 1.490, 627.1 | A |
| I-197 | W-11 | $CF_3$ | $C_2H_5$ | G1, $R^{41}$: Cl, $R^{42}$: H | 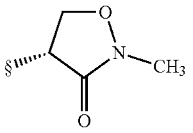 | H | 1.300, 599.1 | A |
| I-198 | W-11 | $CF_3$ | $C_2H_5$ | G1, $R^{41}$: $CH_3$, $R^{42}$: H | (1-CN)-c-$C_3H_4$ | H | 1.359, 543.2 | A |
| I-199 | W-9 | $CF_3$ | $C_2H_5$ | G1, $R^{41}$: $OCF_3$, $R^{42}$: H | c-$C_3H_5$ | H | 1.413, 570.1 | A |
| I-200 | W-9 | $CF_3$ | $C_2H_5$ | G1, $R^{41}$: $OCF_3$, $R^{42}$: H | 5-CN-pyrid-2-yl | H | 1.466, 632.1 | A |
| I-201 | W-11 | $CF_3$ | $CH_2OC_2H_5$ | G1, $R^{41}$: Cl, $R^{42}$: H | 5-F-pyrid-2-yl | H | 1.466, 625.1 | A |
| I-202 | W-11 | $CF_3$ | C(=O)$OC_2H_5$ | G1, $R^{41}$: Cl, $R^{42}$: H | 3-F-pyrid-2-yl | H | 1.382, 639.0 | A |
| I-203 | W-11 | $CF_3$ | C(=O)$OC_2H_5$ | G1, $R^{41}$: Cl, $R^{42}$: H | c-$C_3H_5$ | H | 1.382, 584.1 | A |
| I-204 | W-11 | $CF_3$ | C(=O)$OC_2H_5$ | G1, $R^{41}$: Cl, $R^{42}$: H | pyrid-2-yl | H | 1.373, 621.1 | A |
| I-205 | W-11 | $CF_3$ | C(=O)$OC_2H_5$ | G1, $R^{41}$: Cl, $R^{42}$: H | pyrid-2-yl | $CH_3$ | 1.449, 635.1 | A |
| I-206 | W-9 | $CF_3$ | $C_2H_5$ | G1, $R^{41}$: $OCF_3$, $R^{42}$: H | (1-CN)-c-$C_3H_4$ | H | 1.387, 595.2 | A |
| I-207 | W-11 | $CF_3$ | C(=O)$OC_2H_5$ | G1, $R^{41}$: Cl, $R^{42}$: H | 5-F-pyrid-2-yl | H | 1.473, 637.1 | A |
| I-208 | W-11 | $CF_3$ | C(=O)$OC_2H_5$ | G1, $R^{41}$: Cl, $R^{42}$: H | 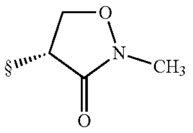 | H | 1.321, 641.2 | A |
| I-209 | W-11 | $CF_3$ | C(=O)$OC_2H_5$ | G1, $R^{41}$: Cl, $R^{42}$: H | (1-CN)-c-$C_3H_4$ | H | 1.368, 609.0 | A |
| I-210 | W-9 | $CF_3$ | $C_2H_5$ | G1, $R^{41}$: $OCF_3$, $R^{42}$: H | pyrid-2-yl | $CH_3$ | 1.466, 621.1 | A |
| I-211 | W-9 | $CF_3$ | $C_2H_5$ | G1, $R^{41}$: $OCF_3$, $R^{42}$: H | 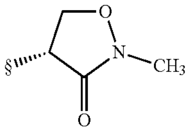 | H | 1.347, 629.1 | A |
| I-212 | W-11 | $CF_3$ | $CH_2OC_2H_5$ | G1, $R^{41}$: Cl, $R^{42}$: H | pyrid-2-yl | H | 1.369, 605.2 | A |
| I-213 | W-11 | $CF_3$ | $CH_2OC_2H_5$ | G1, $R^{41}$: Cl, $R^{42}$: H | pyrid-2-yl | $CH_3$ | 1.442, 621.1 | A |
| I-214 | W-11 | $CF_3$ | C(=O)$OC_2H_5$ | G1, $R^{41}$: Cl, $R^{42}$: H | 5-Cl-pyrid-2-yl | H | 1.520, 655.0 | A |
| I-215 | W-11 | $CF_3$ | $CH_2OC_2H_5$ | G1, $R^{41}$: Cl, $R^{42}$: H | 5-Cl-pyrid-2-yl | H | 1.522, 641.1 | A |
| I-216 | W-9 | $CF_3$ | $C_2H_5$ | G1, $R^{41}$: $OCF_3$, $R^{42}$: H | 3-F-pyrid-2-yl | H | 1.406, 625.1 | A |
| I-217 | W-11 | $CF_3$ | C(=O)$OC_2H_5$ | G1, $R^{41}$: Cl, $R^{42}$: H | 5-CN-pyrid-2-yl | H | 1.451, 646.0 | A |
| I-218 | W-9 | $CF_3$ | $C_2H_5$ | G1, $R^{41}$: F, $R^{42}$: H | 3-F-pyrid-2-yl | H | 1.344, 559.2 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-219 | W-8 | $CF_3$ | $C_2H_5$ | G1, $R^{41}$: Cl, $R^{42}$: H | pyrid-2-yl | $CH_3$ | 1.343, 555.2 | A |
| I-220 | W-9 | $CF_3$ | $C_2H_5$ | G1, $R^{41}$: F, $R^{42}$: H | (1-CN)-c-$C_3H_4$ | H | 1.325, 529.2 | A |
| I-221 | W-8 | $CF_3$ | $C_2H_5$ | G1, $R^{41}$: Cl, $R^{42}$: H | 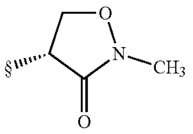 | H | 1.217, 563.1 | A |
| I-222 | W-9 | $CF_3$ | $C_2H_5$ | G1, $R^{41}$: F, $R^{42}$: H | 3,5-$F_2$-pyrid-2-yl | H | 1.376, 577.2 | A |
| I-223 | W-9 | $CF_3$ | $C_2H_5$ | G1, $R^{41}$: F, $R^{42}$: H | 5-Cl-pyrid-2-yl | H | 1.531, 575.1 | A |
| I-224 | W-9 | $CF_3$ | $C_2H_5$ | G1, $R^{41}$: F, $R^{42}$: H | pyrid-2-yl | H | 1.323, 540.9 | A |
| I-225 | W-8 | $CF_3$ | $C_2H_5$ | G1, $R^{41}$: Cl, $R^{42}$: H | 5-F-pyrimidin-2-yl | H | 1.276, 560.1 | A |
| I-226 | W-9 | $CF_3$ | $C_2H_5$ | G1, $R^{41}$: F, $R^{42}$: H | 5-CN-pyrid-2-yl | H | 1.437, 566.2 | A |
| I-227 | W-9 | $CF_3$ | $C_2H_5$ | G1, $R^{41}$: F, $R^{42}$: H | 5-F-pyrid-2-yl | H | 1.465, 559.1 | A |
| I-228 | W-8 | $CF_3$ | $C_2H_5$ | G1, $R^{41}$: Cl, $R^{42}$: H | 5-CN-pyrid-2-yl | H | 1.367, 566.1 | A |
| I-229 | W-8 | $CF_3$ | $C_2H_5$ | G1, $R^{41}$: Cl, $R^{42}$: H | 3-F-pyrid-2-yl | H | 1.293, 559.2 | A |
| I-230 | W-8 | $CF_3$ | $C_2H_5$ | G1, $R^{41}$: Cl, $R^{42}$: H | 5-F-pyrid-2-yl | H | 1.356, 558.9 | A |
| I-231 | W-9 | $CF_3$ | $C_2H_5$ | G1, $R^{41}$: F, $R^{42}$: H | 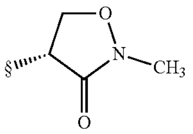 | H | 1.270, 563.2 | A |
| I-232 | W-8 | $CF_3$ | $C_2H_5$ | G1, $R^{41}$: Cl, $R^{42}$: H | 3,5-$F_2$-pyrid-2-yl | H | 1.330, 577.1 | A |
| I-233 | W-8 | $CF_3$ | $C_2H_5$ | G1, $R^{41}$: Cl, $R^{42}$: H | (1-CN)-c-$C_3H_4$ | H | 1.278, 529.2 | A |
| I-234 | W-8 | $CF_3$ | $C_2H_5$ | G1, $R^{41}$: Cl, $R^{42}$: H | 5-Cl-pyrid-2-yl | H | 1.454, 577.1 | A |
| I-235 | W-11 | $CF_3$ | H | G1, $R^{41}$: Cl, $R^{42}$: H | 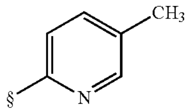 | H | 1.287, 563.1 | A |
| I-236 | W-11 | $CF_3$ | H | G1, $R^{41}$: Cl, $R^{42}$: H | 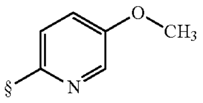 | H | 1.377, 579.0 | A |
| I-237 | W-11 | $CF_3$ | H | G1, $R^{41}$: Cl, $R^{42}$: H | 5-Br,3-F-pyrid-2-yl | H | 1.421, 645.0 | A |
| I-238 | W-11 | $CF_3$ | H | G1, $R^{41}$: Cl, $R^{42}$: H | 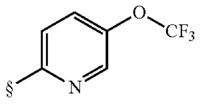 | H | 1.518, 631.1 | A |
| I-239 | W-11 | $CF_3$ | H | G1, $R^{41}$: Cl, $R^{42}$: H | 3-Cl-pyrid-2-yl | H | 1.361, 583.1 | A |
| I-240 | W-11 | $CF_3$ | H | G1, $R^{41}$: Cl, $R^{42}$: H | pyridazin-3-yl | H | 1.303, 548.1 | A |

TABLE I.1-continued compounds of formula I (U = O, X = $NR^3$, Y = direct bond)

| No. | WP | $R^1$ | $R^3$ | G | $R^5$ | $R^6$ | phys. data [HPLC Rt [min], M + H [m/z]] | HPLC meth-od |
|---|---|---|---|---|---|---|---|---|
| I-241 | W-11 | $CF_3$ | H | G1, $R^{41}$: Cl, $R^{42}$: H | pyrazin-2-yl | H | 1.348, 550.1 | A |
| I-242 | W-11 | $CF_3$ | H | G1, $R^{41}$: Cl, $R^{42}$: H | 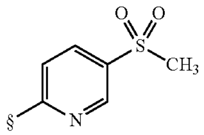 | H | 1.355, 627.1 | A |
| I-243 | W-11 | $CF_3$ | H | G1, $R^{41}$: Cl, $R^{42}$: H | pyrid-2-yl | H | 1.292, 549.0 | A |
| I-244 | W-11 | $CF_3$ | H | G1, $R^{41}$: Cl, $R^{42}$: H | 5-Cl-pyrid-2-yl | H | 1.495, 583.0 | A |
| I-245 | W-11 | $CF_3$ | H | G1, $R^{41}$: Cl, $R^{42}$: H | 5-CN-pyrid-2-yl | H | 1.421, 547.2 | A |
| I-246 | W-11 | $CF_3$ | H | G1, $R^{41}$: Cl, $R^{42}$: H | 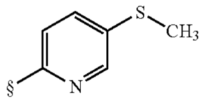 | H | 1.466, 595.0 | A |
| I-247 | W-11 | $CF_3$ | H | G1, $R^{41}$: Cl, $R^{42}$: H | 5-Cl,3-F-pyrid-2-yl | H | 1.413, 601.0 | A |
| I-248 | W-11 | $CF_3$ | H | G1, $R^{41}$: Cl, $R^{42}$: H | 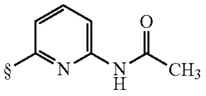 | H | 1.303, 606.1 | A |
| I-249 | W-11 | $CF_3$ | H | G1, $R^{41}$: Cl, $R^{42}$: H | 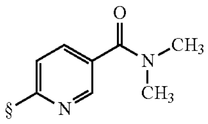 | H | 1.314, 620.1 | A |
| I-250 | W-11 | $CF_3$ | H | G1, $R^{41}$: Cl, $R^{42}$: H | 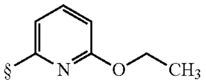 | H | 1.518, 591.1 | A |
| I-251 | W-11 | $CF_3$ | H | G1, $R^{41}$: Cl, $R^{42}$: H | 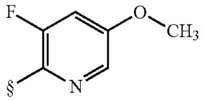 | H | 1.350, 597.1 | A |
| I-252 | W-11 | $CF_3$ | H | G1, $R^{41}$: Cl, $R^{42}$: H | pyrimidin-5-yl | H | 1.292, 550.0 | A |
| I-253 | W-11 | $CF_3$ | H | G1, $R^{41}$: Cl, $R^{42}$: H | 3-F-pyrid-2-yl | H | 1.327, 567.1 | A |

§ = bond to the remainder of the molecule;

# = bond to X;

% = bond to Y

<S> S-Enantiomer (Formula I.A)

<R> R-Enantiomer (Formula I.B)

TABLE I.2 compounds of formula I.2 (formula I with U = O, Y = direct bond)

| No. | W | $R^1$ | X | G | $R^5$ | $R^6$ | phys. data [HPLC Rt [min], M + H [m/z]] | HPLC method |
|---|---|---|---|---|---|---|---|---|
| II-1 | W-9 | $CF_3$ | O | G1, $R^{41}$: Cl, $R^{42}$: H | (1-CN)-c-$C_3H_4$ | H | 1.300, 520.2 | A |
| II-2 | W-9 | $CF_3$ | S | G1, $R^{41}$: Cl, $R^{42}$: H | (1-CN)-c-$C_3H_4$ | H | 1.341, 535.8 | A |
| II-3 | W-9 | $CF_3$ | $SO_2$ | G1, $R^{41}$: Cl, $R^{42}$: H | (1-CN)-c-$C_3H_4$ | H | 1.324, 568.3 | A |
| II-4 | W-11 | $CF_3$ | O | G1, $R^{41}$: Cl, $R^{42}$: H | c-$C_3H_5$ | H | 1.333, 512.8 | A |
| II-5 | W-11 | $CF_3$ | O | G1, $R^{41}$: Cl, $R^{42}$: H | (1-CN)-c-$C_3H_4$ | H | 1.319, 538.9 | A |
| II-6 | W-11 | $CF_3$ | O | G1, $R^{41}$: Cl, $R^{42}$: H | (1-CN)-c-$C_3H_4$ | $CH_3$ | 1.377, 552.0 | A |
| II-7 | W-11 | $CF_3$ | O | G1, $R^{41}$: Cl, $R^{42}$: H | 4-F-$C_6H_4$ | $CH_3$ | 1.457, 579.1 | A |
| II-8 | W-11 | $CF_3$ | O | G1, $R^{41}$: Cl, $R^{42}$: H | 3,5-$F_2$-pyrid-2-yl | H | 1.368, 586.1 | A |
| II-9 | W-11 | $CF_3$ | O | G1, $R^{41}$: Cl, $R^{42}$: H | 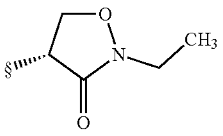 | H | 1.332, 584.1 | A |
| II-10 | W-11 | $CF_3$ | O | G1, $R^{41}$: Cl, $R^{42}$: $OS(=O)_2CH_3$ | (1-CN)-c-$C_3H_4$ | H | 1.238, 595.8 | A |
| II-11 | W-11 | $CF_3$ | O | G1, $R^{41}$: Cl, $R^{42}$: $OCF_3$ | (1-CN)-c-$C_3H_4$ | H | 1.375, 586.1 | A |
| II-12 | W-8 | $CF_3$ | $CH_2$ | G1, $R^{41}$: Cl, $R^{42}$: H | 3,5-$F_2$-pyrid-2-yl | H | 1.272, 548.1 | A |

§ = bond to the remainder of the molecule

TABLE I.3 compounds of formula I.3 (formula I with U = O, Y = $CR^6R^7$)

| No. | W | $R^1$ | X | G | Y | $R^5$ | $R^6$ | phys. data [HPLC Rt [min], M + H [m/z]] | HPLC method |
|---|---|---|---|---|---|---|---|---|---|
| III-1 | W-8 | $CF_3$ | NH | G1, $R^{41}$: $CH_3$, $R^{42}$: H | $CH_2$ | (1-CN)-c-$C_3H_4$ | H | 1.201, 515.3 | A |
| III-2 | W-11 | $CF_3$ | NH | G1, $R^{41}$: F, $R^{42}$: H | (1,1)c-$C_4H_6$ | (1-CN)-c-$C_3H_4$ | H | 1.376, 572.9 | A |
| III-3 | W-11 | $CF_3$ | NH | G1, $R^{41}$: $CH_3$, $R^{42}$: H | $CF_2$ | 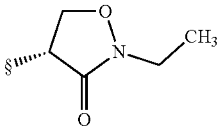 | H | 1.349, 612.9 | A |
| III-4 | W-11 | $CF_3$ | NH | G1, $R^{41}$: $CH_3$, $R^{42}$: H | $CF_2$ | (1-CN)-c-$C_3H_4$ | H | 1.338, 565.3 | A |

§ = bond to the remainder of the molecule

Biological Examples

If not otherwise specified, the test solutions were prepared as follows:

The active compound was dissolved at the desired concentration in a mixture of 1:1 (vol:vol) distilled water: acetone. The test solution was prepared at the day of use.

Test solutions were prepared in general at a concentration of 2500 ppm (wt/vol).

B.1. Boll Weevil (*Anthonomus grandis*)

For evaluating control of boll weevil, the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 µl, using a custom-built micro atomizer, at two replications.

After application, microtiter plates were incubated at about 25±1° C. and about 75±5% relative humidity for 5 days. Egg and larval mortality were then visually assessed.

In this test, compounds I-1, I-2, I-3, I-4, I-5, I-6, I-7, I-8, I-9, I-10, I-11, I-12, I-13, I-14, I-15, I-16, I-18, I-19, I-20, I-21, I-22, I-23, I-24, I-25, I-26, I-27, I-28, I-30, I-31, I-32, I-33, I-34, I-35, I-37, I-38, I-39, I-40, I-41, I-42, I-43, I-44, I-45, I-46, I-47, I-48, I-49, I-50, I-52, I-53, I-55, I-56, I-57, I-58, I-59, I-60, I-61, I-63, I-65, I-66, I-67, I-68, I-69, I-70, I-71, I-72, I-74, I-75, I-76, I-77, I-78, I-79, I-81, I-84, I-85, I-87, I-88, I-89, I-90, I-91, I-95, I-97, I-98, I-99, I-100, I-101, I-102, I-103, I-104, I-105, I-106, I-107, I-108, I-109, I-110, I-111, I-112, I-114, I-115, I-116, I-117, I-118, I-120, I-121, I-122, I-123, I-124, I-125, I-126, I-127, I-128, I-131, I-132, I-133, I-134, I-135, I-136, I-137, I-139, I-140, I-141, I-142, I-143, I-145, I-146, I-147, I-148, I-149, I-150, I-151, I-152, I-153, I-154, I-155, I-157, I-158, I-159, I-160, I-161, I-162, I-163, I-164, I-165, I-167, I-168, I-169, I-170, I-171, I-172, I-173, I-174, I-175, I-177, I-181, I-183, I-184, I-188, I-189, I-190, I-191, I-192, I-194, I-196, I-197, I-198, I-199, I-200, I-204, I-205, I-206, I-207, I-208, I-209, I-210, I-211, I-212, I-214, I-215, I-216, I-219, I-220, I-221, I-222, I-223, I-226, I-227, I-228, I-230, I-231, I-232, I-233, I-234, I-235, I-236, I-238, I-240, I-242, I-243, I-244, I-246, I-248, I-249, I-250, I-251, I-252, II-1, II-4, II-5, II-6, II-7, II-8, II-9, II-11, III-1, and III-4, resp., at 2500 ppm showed at least 75% mortality in comparison with untreated controls.

B.2. Greenhouse Whitefly (*Trialeurodes vaporarirorum*)

For evaluating control of Greenhouse Whitefly, the test unit consisted of 96-well-microtiter plates containing a leaf disk of eggplant leaf disk with Whitefly eggs. The compounds or mixtures were formulated using a solution containing 75% water and 25% DMSO. Different concentrations of formulated were sprayed onto the insect diet at 2.5 µl, using a custom-built micro atomizer, at two replications. After application, microtiter plates were incubated at 23±1° C., 65±5% RH for 6 days. Mortality of hatched crawlers was then visually assessed.

In this test, compounds I-21, I-25, I-34, I-37, I-38, I-42, I-47, I-63, I-67, I-108, I-174, and II-4, resp., at 2500 ppm showed at least 75% mortality in comparison with untreated controls.

B.3. Green Peach Aphid (*Myzus persicae*) (Mixed Life Stages)

For evaluating control of Green Peach Aphid through systemic means the test unit consisted of 96-well-microtiter plates containing liquid artificial diet under an artificial membrane. The compounds were formulated using a solution containing 75% v/v water and 25% v/v DMSO. Different concentrations of formulated compounds were pipetted into the aphid diet, using a custom-built pipette, at two replications. After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compounds I-1, I-2, I-3, I-4, I-5, I-6, I-7, I-8, I-9, I-10, I-11, I-12, I-13, I-14, I-15, I-17, I-19, I-21, I-22, I-23, I-24, I-25, I-26, I-27, I-31, I-32, I-33, I-34, I-35, I-37, I-38, I-39, I-40, I-41, I-42, I-43, I-45, I-46, I-48, I-49, I-50, I-52, I-55, I-56, I-59, I-61, I-63, I-65, I-66, I-67, I-68, I-69, I-71, I-72, I-74, I-75, I-76, I-77, I-78, I-81, I-84, I-85, I-87, I-88, I-90, I-95, I-97, I-98, I-102, I-103, I-104, I-105, I-106, I-107, I-108, I-110, I-112, I-114, I-115, I-116, I-120, I-121, I-122, I-123, I-125, I-126, I-127, I-128, I-131, I-132, I-133, I-135, I-137, I-138, I-140, I-142, I-145, I-146, I-147, I-148, I-150, I-152, I-153, I-154, I-155, I-159, I-164, I-165, I-167, I-168, I-169, I-170, I-173, I-174, I-177, I-181, I-183, I-184, I-188, I-190, I-191, I-192, I-194, I-196, I-197, I-200, I-206, I-210, I-211, I-212, I-215, I-216, I-219, I-220, I-221, I-222, I-226, I-227, I-228, I-230, I-231, I-232, I-233, I-235, I-236, I-238, I-240, I-242, I-243, I-244, I-246, I-248, I-249, I-250, I-251, I-252, II-1, II-4, II-5, II-6, II-7, II-8, II-9, II-11, and III-4, resp., at 2500 ppm showed at least 75% mortality in comparison with untreated controls.

B.4. Tobacco Budworm (*Heliothis virescens*)

For evaluating control of Tobacco Budworm, the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 µl, using a custom-built micro atomizer, at two replications. After application, microtiter plates were incubated at about 28±1° C. and about 80±5% relative humidity for 5 days. Egg and larval mortality was then visually assessed.

In this test, compounds I-1, I-2, I-3, I-4, I-5, I-6, I-7, I-8, I-9, I-10, I-11, I-12, I-13, I-14, I-15, I-16, I-18, I-19, I-21, I-22, I-23, I-24, I-25, I-26, I-27, I-28, I-30, I-31, I-32, I-33, I-34, I-35, I-37, I-38, I-39, I-40, I-41, I-42, I-43, I-44, I-45, I-46, I-47, I-48, I-49, I-50, I-52, I-53, I-55, I-56, I-57, I-58, I-59, I-60, I-61, I-63, I-65, I-66, I-67, I-68, I-69, I-70, I-71, I-72, I-74, I-75, I-76, I-77, I-78, I-79, I-81, I-84, I-85, I-87, I-88, I-89, I-91, I-94, I-95, I-97, I-98, I-99, I-100, I-101, I-102, I-103, I-104, I-105, I-106, I-107, I-108, I-110, I-111, I-112, I-114, I-115, I-116, I-117, I-118, I-120, I-121, I-122, I-123, I-124, I-125, I-126, I-127, I-128, I-131, I-132, I-133, I-134, I-135, I-136, I-137, I-138, I-139, I-140, I-142, I-143, I-145, I-146, I-147, I-148, I-149, I-150, I-151, I-152, I-153, I-154, I-155, I-156, I-157, I-158, I-159, I-160, I-161, I-163, I-164, I-165, I-167, I-168, I-169, I-170, I-171, I-172, I-173, I-174, I-181, I-183, I-184, I-188, I-189, I-190, I-191, I-192, I-194, I-196, I-197, I-198, I-199, I-200, I-204, I-205, I-206, I-207, I-208, I-209, I-210, I-211, I-212, I-214, I-215, I-216, I-219, I-220, I-221, I-222, I-223, I-226, I-227, I-228, I-230, I-231, I-232, I-233, I-234, I-235, I-236, I-238, I-240, I-242, I-243, I-244, I-246, I-248, I-249, I-250, I-251, I-252, II-1, II-4, II-5, II-6, II-7, II-8, II-9, II-11, III-1, III-3, and III-4, resp., at 2500 ppm showed at least 75% mortality in comparison with untreated controls.

B.5. Yellow Fever Mosquito (*Aedes aegypti*)

For evaluating control of Yellow Fever Mosquito, the test unit consisted of 96-well-microtiter plates containing 200 µl of tap water per well and 5-15 freshly hatched *A. aegypti* larvae. The active compounds were formulated using a solution containing 75% (v/v) water and 25% (v/v) DMSO. Different concentrations of formulated compounds or mixtures were sprayed onto the insect diet at 2.5 µl, using a custom-built micro atomizer, at two replications.

After application, microtiter plates were incubated at 28±1° C., 80±5% RH for 2 days. Larval mortality was then visually assessed.

In this test, compounds I-1, I-2, I-3, I-4, I-5, I-6, I-7, I-9, I-10, I-11, I-13, I-14, I-15, I-16, I-17, I-18, I-19, I-20, I-21, I-23, I-24, I-25, I-26, I-27, I-28, I-30, I-31, I-32, I-33, I-34, I-35, I-37, I-39, I-40, I-41, I-42, I-43, I-45, I-46, I-48, I-49, I-50, I-55, I-57, I-59, I-60, I-61, I-63, I-65, I-66, I-67, I-68, I-69, I-70, I-71, I-72, I-74, I-75, I-76, I-78, I-79, I-84, I-85, I-86, I-87, I-89, I-90, I-94, I-95, I-97, I-98, I-99, I-100, I-101, I-102, I-103, I-104, I-106, I-107, I-108, I-110, I-111, I-114, I-115, I-116, I-117, I-118, I-120, I-121, I-122, I-123, I-124, I-126, I-127, I-128, I-130, I-131, I-132, I-133, I-134, I-135, I-136, I-137, I-138, I-140, I-142, I-143, I-144, I-145, I-146, I-147, I-148, I-149, I-150, I-152, I-154, I-155, I-157, I-158, I-160, I-161, I-162, I-163, I-164, I-165, I-168, I-169, I-170, I-172, I-173, I-174, I-177, I-181, I-183, I-184, I-188, I-189, I-190, I-191, I-192, I-194, I-196, I-197, I-198, I-199, I-200, I-204, I-205, I-206, I-207, I-208, I-209, I-210, I-211, I-212, I-214, I-215, I-216, I-219, I-220, I-221, I-222, I-223, I-226, I-227, I-228, I-230, I-231, I-232, I-233, I-234, I-235, I-236, I-238, I-240, I-242, I-243, I-244, I-246, I-248, I-249, I-250, I-251, I-252, II-1, II-4, II-5, II-6, II-7, II-8, II-9, II-11, III-1, III-2, and III-3, resp., at 2500 ppm showed at least 75% mortality in comparison with untreated controls.

B.6. Diamond Back Moth (*Plutella xylostella*)

The active compound was dissolved at the desired concentration in a mixture of 1:1 (vol:vol) distilled water: acetone. Surfactant (Kinetic) was added at a rate of 0.01% (vol/vol). The test solution was prepared at the day of use. Cabbage leaf discs (60 mm in diameter) were dipped in test solution and air-dried. Treated leaves were placed in petri dishes lined with moistened filter paper and inoculated with ten 3rd instar larvae. Mortality was recorded 72 hours after treatment. Feeding damages were also recorded using a scale of 0-100%.

In this test, compounds I-1, I-2, I-3, I-4, I-5, I-6, I-7, I-8, I-9, I-10, I-11, I-12, I-13, I-14, I-15, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-54, I-55, I-56, I-58, I-59, I-60, I-61, I-62, I-63, I-64, I-65, I-66, I-67, I-68, I-69, I-70, I-71, I-72, I-73, I-74, I-75, I-76, I-77, I-78, I-79, I-80, I-81, I-82, I-84, I-85, I-86, I-87, I-88, I-89, I-90, I-91, I-92, I-93, I-94, I-95, I-96, I-97, I-98, I-99, I-100, I-101, I-102, I-103, I-104, I-105, I-106, I-107, I-108, I-109, I-110, I-111, I-112, I-113, I-114, I-115, I-116, I-117, I-118, I-119, I-120, I-121, I-122, I-123, I-124, I-125, I-126, I-127, I-128, I-129, I-130, I-131, I-132, I-133, I-134, I-135, I-136, I-137, I-138, I-139, I-140, I-141, I-142, I-143, I-144, I-145, I-146, I-147, I-148, I-149, I-150, I-151, I-152, I-153, I-154, I-155, I-156, I-157, I-158, I-159, I-160, I-161, I-162, I-163, I-164, I-165, I-166, I-167, I-168, I-169, I-170, I-171, I-172, I-173, I-174, I-175, II-1, II-3, II-4, II-5, II-6, II-7, II-8, III-2, III-3, and III-4, resp., at 300 ppm showed at least 75% mortality in comparison with untreated controls.

B.7. Orchid *Thrips* (*Dichromothrips corbetti*)

*Dichromothrips corbetti* adults used for bioassay were obtained from a colony maintained continuously under laboratory conditions. For testing purposes, the test compound was diluted in a 1:1 mixture of acetone:water (vol:vol), plus Kinetic at a rate of 0.01% v/v.

*Thrips* potency of each compound was evaluated by using a floral-immersion technique. Each orchid petal was dipped into treatment solution and allowed to dry in Petri dishes. Treated petals were placed into individual re-sealable plastic along with about 20 adult *thrips*. All test arenas were held under dark condition and a temperature of about 28° C. for duration of the assay. The percent mortality was recorded 72 hours after treatment.

In this test, compounds I-1, I-2, I-3, I-4, I-5, I-6, I-7, I-8, I-9, I-10, I-11, I-12, I-13, I-14, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, I-51, I-52, I-53, 1-54, I-55, I-56, I-58, I-59, I-60, I-61, I-62, I-63, I-64, I-65, I-66, I-67, I-68, I-69, I-70, I-71, I-72, I-73, I-74, I-75, I-76, I-77, I-78, I-79, I-80, I-81, I-83, I-84, I-85, I-86, I-87, I-88, I-89, I-91, I-92, I-93, I-94, I-95, I-97, I-98, I-99, I-100, I-101, I-102, I-103, I-104, I-105, I-106, I-107, I-108, I-110, I-111, I-112, I-113, I-114, I-115, I-116, I-117, I-118, I-119, I-120, I-121, I-122, I-123, I-124, I-125, I-126, I-127, I-128, I-130, I-131, I-132, I-133, I-134, I-135, I-136, I-137, I-138, I-140, I-142, I-144, I-145, I-146, I-147, I-148, I-149, I-150, I-151, I-152, I-153, I-154, I-155, I-156, I-157, I-158, I-159, I-160, I-161, I-163, I-164, I-165, I-166, I-167, I-168, I-169, I-170, I-171, I-173, I-174, I-175, II-1, II-4, II-5, II-6, II-7, and 11-8, resp., at 300 ppm showed at least 75% mortality in comparison with untreated controls.

B.8. Green Soldier Stink Bug (*Nezara viridula*)

The active compound was dissolved at the desired concentration in a mixture of 1:1 (vol:vol) distilled water: aceteone. Surfactant (Kinetic) was added at a rate of 0.01% (vol/vol). The test solution was prepared at the day of use. Soybean pods were placed in 90×50 mm glass Petri dishes lined with moistened filter paper and inoculated with ten late 3rd instar *N. viridula*. Using a hand atomizer, an approximately 2 ml solution was sprayed into each Petri dish. Treated setup was kept at about 25-26° C. and relative humidity of about 65-70%. Percent mortality was recorded after 5 days.

In this test, compounds, I-1, I-2, I-3, I-4, I-9, I-12, I-21, I-22, I-23, I-24, I-25, I-26, I-27, I-28, I-32, I-38, I-55, I-60, I-63, I-65, I-66, I-67, I-68, I-72, I-76, I-98, I-102, I-104, I-108, I-110, I-111, I-115, I-116, I-119, I-120, I-132, I-135, I-137, I-140, I-145, I-146, I-147, I-150, I-154, I-157, I-158, I-159, I-165, I-166, I-168, I-174, II-4, II-5, II-6, II-7, and 11-8, resp., at 300 ppm showed at least 75% mortality in comparison with untreated controls.

B.9. Rice Green Leafhopper (*Nephotettix virescens*)

Four to five-week old rice seedlings with cut upper leaf portion were cleaned and washed 24 hours before spraying. The active compounds were formulated in 1:1 acetone:water (vol:vol), and 0.01% vol/vol surfactant (Kinetic) was added. Potted rice seedlings were sprayed with 5-6 ml test solution, air dried, covered with Mylar cages and inoculated with 10 adults. Treated rice plants were kept at about 28-29° C. and relative humidity of about 50-60%. Percent mortality was recorded after 72 hours.

In this test, compounds, I-24, I-25, I-28, I-32, I-60, I-63, I-75, I-101, I-108, I-115, I-116, I-118, I-119, I-120, I-126, I-137, I-146, I-170, I-173, I-174, I-175, II-4, II-6, II-7, and 11-8, resp., at 300 ppm showed at least 75% mortality in comparison with untreated controls.

B.10. Red Spider Mite (*Tetranychus kanzawai*)

The active compound was dissolved at the desired concentration in a mixture of 1:1 (vol:vol) distilled water: acetone. Add surfactant (Kinetic) was added at a rate of 0.01% (vol/vol). The test solution was prepared at the day of use. Potted cowpea beans of 4-5 days of age were cleaned with tap water and sprayed with I-2 ml of the test solution using air driven DeVilbiss® hand atomizer at 20-30 psi (≈1,38 to 2,07 bar). The treated plants were allowed to air dry and afterwards inoculated with 30 or more mites by clipping a cassava leaf section from rearing population. Treated plants were placed inside a holding room at about 25-26° C. and about 65-70% relative humidity. Percent mortality was assessed 72 hours after treatment.

In this test, compounds I-9, I-27, I-61, I-98, I-104, I-111, I-132, I-145, I-146, I-150, I-174, II-1, II-4, II-5, II-6, II-7, and 11-8, resp., at 300 ppm showed at least 75% mortality in comparison with untreated controls.

B.11. Southern Armyworm (*Spodoptera eridania*), 2nd Instar Larvae

The active compounds were formulated by a Tecan liquid handler in 100% cyclohexanone as a 10'000 ppm solution supplied in tubes. The 10'000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects. Lima bean plants (variety Sieva) were grown 2 plants to a pot and selected for treatment at the 1st true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. Ten to 11 armyworm larvae were placed into the bag and the bags zipped closed. Test plants were maintained in a growth room at about 25° C. and about 20-40% relative humidity for 4 days, avoiding direct exposure to fluorescent light (14:10 light:dark photo-period) to prevent trapping of heat inside the bags. Mortality and reduced feeding were assessed 4 days after treatment, compared to untreated control plants.

In this test, compounds, I-7, I-12, I-21, I-22, I-23, I-24, I-25, I-26, I-27, I-28, I-30, I-31, I-32, I-33, I-34, I-35, I-36, I-37, I-38, I-39, I-40, I-41, I-42, I-43, I-44, I-45, I-46, I-47, I-48, I-49, I-50, I-52, I-53, I-55, I-56, I-57, I-58, I-59, I-60, I-61, I-63, I-64, I-65, I-67, I-68, I-69, I-70, I-71, I-72, I-73, I-74, I-75, I-76, I-77, I-78, I-79, I-80, I-81, I-82, I-84, I-85, I-86, I-87, I-88, I-89, I-90, I-93, I-94, I-95, I-97, I-98, I-99, I-100, I-101, I-102, I-103, I-104, I-105, I-106, I-107, I-108, I-109, I-110, I-111, I-114, I-115, I-126, I-127, I-128, I-129, I-130, I-131, I-137, I-138, I-139, I-140, I-141, I-143, I-144, I-145, I-146, I-147, I-148, I-149, I-150, I-151, I-152, I-153, I-154, I-155, I-156, I-157, I-159, I-160, I-161, I-162, I-163, I-164, I-165, I-167, I-169, I-170, I-171, I-173, I-174, I-175, I-176, II-1, II-4, II-5, II-6, II-7, and 11-8, resp., at 300 ppm showed at least 75% mortality in comparison with untreated controls.

B.12. Silverleaf Whitefly (*Bemisia argentifolii*) (Adults)

The active compounds were formulated by a Tecan liquid handler in 100% cyclohexanone as a 10,000-ppm solution supplied in tubes. The 10,000-ppm solution was serially diluted in 100% cyclohexanone to make interim solutions. These served as stock solutions for which final dilutions were made by the Tecan in 50% acetone:50% water (v/v) into 5 or 10 ml glass vials. A nonionic surfactant (Kinetic®) was included in the solution at a volume of 0.01% (v/v). The vials were then inserted into an automated electrostatic sprayer equipped with an atomizing nozzle for application to plants/insects. Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (14:10 light:dark photoperiod) to prevent trapping of heat inside the cup. Mortality was assessed 3 days after treatment, compared to untreated control plants.

In this test, compounds I-21, I-24, I-25, I-32, I-47, I-63, I-65, I-69, I-75, I-77, I-78, I-79, I-80, I-87, I-93, I-98, I-100, I-109, I-110, I-111, I-114, I-126, I-128, I-130, I-137, I-140, I-143, I-145, I-153, I-156, I-157, I-160, I-162, I-174, II-1, II-4, II-6, II-7, and II-8, resp., at 300 ppm showed at least 75% mortality in comparison with untreated controls.

The invention claimed is:

1. A compound of formula I

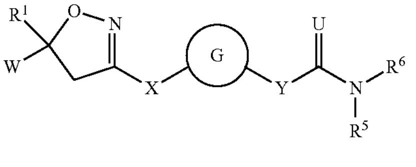

I wherein $R^1$ is $C_1$-$C_2$-haloalkyl;

W is phenyl, or 5- or 6-membered heteroaryl comprising as ring members 1, 2, or 3 heteroatoms selected from N, O, and S; wherein W is unsubstituted, partially or fully substituted with $R^2$;

$R^2$ is halogen, $OR^{21}$, $NR^{22}R^{23}$, CN, $NO_2$, $Si(CH_3)_3$, $SbF_5$, $C_1$-$C_4$-alkyl, $C_1$-$C_4$-haloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_3$-alkoxy, $C_1$-$C_3$-haloalkoxy, $C_1$-$C_3$-alkyl-$S(O)_m$, $C_1$-$C_3$-haloalkyl-$S(O)_m$, $C_1$-$C_3$-alkoxy-$C_1$-$C_4$-alkyl, $C_1$-$C_3$-haloalkoxy-$C_1$-$C_4$-alkyl, $C_1$-$C_3$-alkyl-$S(O)_m$—$C_1$-$C_4$-alkyl, $C_1$-$C_3$-haloalkyl-$S(O)_m C_1$-$C_4$-alkyl, $C_3$-$C_6$-cyclo¬alkyl, $C_3$-$C_6$-halocyclo¬alkyl; which groups are optionally substituted with $R^{211}$;

m is 0, 1, or 2;

$R^{21}$ H, $C_1$-$C_6$-alkyl, $C_2$-$C_6$-alkenyl, $C_2$-$C_6$-alkynyl, $C_3$-$C_8$-cycloalkyl, $C_1$-$C_4$-alkyl-$S(O)_m$, $Si(C_1$-$C_4$-$alkyl)_3$, which groups are unsubstituted, or partially or fully substituted with $R^{211}$;

$R^{211}$ halogen, $C_1$-$C_4$-alkoxy, $C_1$-$C_4$-haloalkoxy, $C_3$-$C_4$-alkenyloxy, $C_3$-$C_4$-haloalkenyloxy, $C_3$-$C_4$-alkynyloxy, $C_3$-$C_4$-haloalkynyloxy, $C_1$-$C_4$-alkyl-$S(O)_m$, $C_1$-$C_4$-haloalkyl-$S(O)_m$, $C_3$-$C_4$-alkenyl-$S(O)_m$, $C_3$-$C_4$-haloalkenyl-$S(O)_m$, $C_3$-$C_4$-alkynyl-$S(O)_m$, $C_3$-$C_4$-haloalkynyl-$S(O)_m$, and oxo; $C_3$-$C_8$-cycloalkyl, $C_3$-$C_8$-halocycloalkyl, $C_3$-$C_8$-cycloalkenyl, $C_3$-$C_8$-halocycloalkenyl;

$R^{22}$, $R^{23}$ H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, which are unsubstituted, or partially or fully substituted with $R^{221}$; or $C_1$-$C_6$-alkyl-C(═O)$OR^{13}$, $C_1$-$C_6$-alkyl-C(═U)N$(R^{12a})R^{12b}$, $C_1$-$C_6$-alkyl-C(═$NR^{12}$)N$(R^{12a})R^{12b}$, $S(O)_m R^{13}$, $S(O)_m N(R^{12a})R^{12b}$, C(═U)$R^{11}$, C(═O)$OR^{13}$, C(═U)N$(R^{12a})R^{12b}$, C(═S)$SR^{13}$, C(═$NR^{12}$)$R^{11}$;

$C_3$-$C_8$-cycloalkyl, $C_3$-$C_8$-halocycloalkyl;

$R^{221}$ CN, $NO_2$, OH, SH, SCN, $SF_5$, $Si(C_1$-$C_4$-$alkyl)_3$, $C_1$-$C_6$-alkoxy, $C_1$-$C_6$-haloalkoxy, $C_1$-$C_6$-alkyl-$S(O)_m$, $C_1$-$C_6$-haloalkyl-$S(O)_m$, C(═O)N$(R^{12a})R^{12b}$;

$C_3$-$C_8$-cycloalkyl which is unsubstituted, or partially or fully halogenated and/or partially or fully substituted with $C_1$-$C_4$-alkyl, $C_3$-$C_4$-cycloalkyl, $C_1$-$C_4$-alkoxy, $C_1$-$C_4$-haloalkoxy, and oxo; or two $R^{221}$ present on the same carbon atom of an alkyl, alkenyl, alkynyl or cycloalkyl group may together be ═O, ═CH($C_1$-$C_4$-alkyl), ═C$(C_1$-$C_4$-$alkyl)_2$, ═N($C_1$-$C_6$-alkyl), or ═NO($C_1$-$C_6$-alkyl); or $R^{22}$ and $R^{23}$ form together with the nitrogen atom they are bonded to a 3-, 4-, 5-, or 6-membered fully unsaturated heterocycle, which heterocycle optionally can contain one heteroatom selected from N, O, and $S(O)_m$ as ring members, and which heterocycle is unsubstituted or partially or fully substituted with $R^{14}$; or $R^{22}$ and $R^{23}$ together form a group ═C$(R^{11})_2$, ═$S(O)_m(R^{13})_2$, ═$S(O)_m R^{13}N(R^{12a})R^{12b}$;

X is $NR^3$, O, $S(O)_m$, or $CH_2$;

$R^3$ is $OR^{21}$, or a group as defined for $R^5$;

G is phenyl, or a 5- or 6-membered heteroaryl comprising as ring members 1, 2, or 3 heteroatoms selected from N, O and S; wherein G is unsubstituted, or partially or fully substituted with $R^4$;

$R^4$ is a group as defined for $R^2$;

U is O or S;

$R^5$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylthio, $C_1$-$C_6$-haloalkylthio, which are unsubstituted, or partially or fully substituted with $R^{51}$; or $C_1$-$C_6$-alkyl-C(=O)OR$^{13}$, $C_1$-$C_6$-alkyl-C(=U)N(R$^{12a}$)R$^{12b}$, $C_1$-$C_6$-alkyl-C(=NR$^{12}$)N(R$^{12a}$)R$^{12b}$, N(R$^{12a}$)R$^{12b}$, S(O)$_m$R$^{13}$, S(O)$_m$N(R$^{12a}$)R$^{12b}$, C(=U)R$^{11}$, C(=O)OR$^{13}$, C(=U)N(R$^{12a}$)R$^{12b}$ C(=S)SR$^{13}$, C(=NR$^{12}$)R$^{11}$;

$C_3$-$C_8$-cycloalkyl, $C_3$-$C_8$-halocycloalkyl, phenyl, a 3-, 4-, 5-, 6- or 7-membered saturated or partially unsaturated heterocycle comprising 1, 2, 3 or 4 heteroatoms selected from N, O, and S(O)$_m$ as ring members, or a 5- or 6-membered hetaryl comprising 1, 2, 3 or 4 heteroatoms selected from N, O, and S(O)$_m$ as ring members, which rings are unsubstituted, or partially or fully substituted with $R^{52}$;

$R^{51}$ halogen, CN, $NO_2$, OH, SH, SCN, $SF_5$, Si($C_1$-$C_4$-alkyl)$_3$, N(R$^{12a}$)R$^{12b}$, $C_1$-$C_6$-alkoxy, $C_1$-$C_6$-haloalkoxy, $C_1$-$C_6$-alkyl-S(O)$_m$, $C_1$-$C_6$-haloalkyl-S(O)$_m$, C(=O)N(R$^{12a}$)R$^{12b}$;

$C_3$-$C_8$-cycloalkyl which is unsubstituted, or partially or fully halogenated and/or partially or fully substituted with CN, $C_1$-$C_4$-alkyl, $C_3$-$C_4$-cycloalkyl, $C_1$-$C_4$-alkoxy, $C_1$-$C_4$-haloalkoxy, and oxo;

N(R$^{12a}$)R$^{12b}$, S(O)$_m$R$^{13}$, S(O)$_m$N(R$^{12a}$)R$^{12b}$, C(=U)R$^{11}$, C(=O)OR$^{13}$, C(=U)N(R$^{12a}$)R$^{12b}$, C(=S)SR$^{13}$, C(=NR$^{12}$)R$^{11}$;

phenyl, benzyl, phenoxy, or 3-, 4-, 5-, 6- or 7-membered saturated, partially or fully unsaturated heterocycle containing 1, 2, or 3 heteroatoms selected from N, O, S(O)$_m$ as ring members, wherein the rings are unsubstituted, or partially or fully substituted with $R^{14}$; or two $R^{51}$ present on the same carbon atom of an alkyl, alkenyl, alkynyl or cycloalkyl group may together be =O, =CH($C_1$-$C_4$-alkyl), =C($C_1$-$C_4$-alkyl)$_2$, =N($C_1$-$C_6$-alkyl), or =NO($C_1$-$C_6$-alkyl);

$R^{52}$ is a group as defined in $R^{51}$ or selected from $C_1$-$C_6$-alkyl, $C_2$-$C_6$-alkenyl, and $C_2$-$C_6$-alkynyl, which groups are unsubstituted, or partially or fully halogenated and/or substituted with one or two CN, $C_3$-$C_4$-cycloalkyl, $C_1$-$C_4$-alkoxy, $C_1$-$C_4$-haloalkoxy, or oxo;

$R^6$ is a group as defined for $R^5$; or $R^5$ and $R^6$ form together with the nitrogen atom they are bonded to a 3-, 4-, 5-, 6-, 7- or 8-membered saturated, or partially or fully unsaturated heterocycle which heterocycle optionally can contain one or two heteroatoms selected from N, O, and S(O)$_m$ as ring members, and which heterocycle is unsubstituted, or partially or fully substituted with $R^{14}$; or $R^5$ and $R^6$ together form a group =C(R$^{11}$)$_2$, =S(O)$_m$(R$^{13}$)$_2$, =S(O)$_m$N(R$^{12a}$)R$^{12b}$, =NR$^{12}$, or =NOR$^{13}$; or $R^5$ and $R^6$ together with the nitrogen they are bound to form a mesoionic entity;

Y having at G one or two ring atoms of G between connection points of G to X and Y; Y being a direct bond or CR$^7$R$^8$;

$R^7$, $R^8$ are each independently selected from H, halogen, CN, $C_1$-$C_6$-alkyl, $C_3$-$C_8$-cycloalkyl, $C_2$-$C_6$-alkenyl, and $C_2$-$C_6$-alkynyl, which groups may be partially or fully halogenated and/or may be substituted by one or more $R^{81}$;

$R^{81}$ is CN, $N_3$, $NO_2$, SCN, $SF_5$, $C_3$-$C_8$-cycloalkyl, $C_3$-$C_8$-halocycloalkyl; Si($C_1$-$C_4$-alkyl)$_3$, OR$^{13}$, OSO$_2$R$^{13}$, S(O)$_m$R$^{13}$, NR$^{22}$R$^{23}$, C(=O)NR$^{22}$R$^{23}$; or $R^7$ and $R^8$, together with the carbon atom they are bonded to, form a 3-, 4-, 5-, 6-, 7- or 8-membered saturated or partially unsaturated carbocycle or heterocycle, wherein the heterocycle comprises 1, 2, 3, or 4 heteroatoms or heteroatom groups independently selected from N, O, and S(O)$_m$ as ring members, which rings are unsubstituted or substituted with 1 or 2 groups $R^{14}$;

$R^{11}$ is CN, $NO_2$, OH, SH, SCN, $SF_5$, $C_1$-$C_6$-alkoxy, $C_1$-$C_6$-haloalkoxy, $C_1$-$C_6$-alkyl-S(O)$_m$, $C_1$-$C_6$-haloalkyl-S(O)$_m$, Si($C_1$-$C_4$-alkyl)$_3$, C(=O)N(R$^{12a}$)R$^{12b}$, $C_3$-$C_8$-cycloalkyl which is unsubstituted, or partially or fully halogenated and/or substituted with 1 or 2 $C_1$-$C_4$-alkyl, $C_3$-$C_4$-cycloalkyl, $C_1$-$C_4$-alkoxy, $C_1$-$C_4$-haloalkoxy, and oxo;

phenyl, benzyl, phenoxy, a 3-, 4-, 5-, 6- or 7-membered saturated, partially or fully unsaturated heterocycle containing 1, 2, or 3 heteroatoms N, O, and S(O)$_m$ as ring members, which rings are unsubstituted, or partially or fully halogenated and/or substituted with $R^{14}$; or two $R^{11}$ present on the same carbon atom of an alkyl, alkenyl, alkynyl or cycloalkyl may together form =O, =CH($C_1$-$C_4$-alkyl), =C($C_1$-$C_4$-alkyl)$C_1$-$C_4$-alkyl, =N($C_1$-$C_6$-alkyl), or =NO($C_1$-$C_6$-alkyl); and $R^{11}$ bonded to a cycloalkyl ring is additionally $C_1$-$C_6$-alkyl, $C_2$-$C_6$-alkenyl, and $C_2$-$C_6$-alkynyl, which are unsubstituted, or partially or fully halogenated and/or substituted with 1 or 2 groups CN, $C_3$-$C_4$-cycloalkyl, $C_1$-$C_4$-alkoxy, $C_1$-$C_4$-haloalkoxy, and oxo; and $R^{11}$ in groups =C(R$^{11}$)$_2$, N=C(R$^{11}$)$_2$, C(=U)R$^{11}$, and C(=NR$^{12}$)R$^{11}$ is additionally selected from H, halogen, $C_1$-$C_6$-alkyl, $C_2$-$C_6$-alkenyl, and $C_2$-$C_6$-alkynyl, which are unsubstituted, or partially or fully halogenated and/or substituted with 1 or 2 groups CN, $C_3$-$C_4$-cycloalkyl, $C_1$-$C_4$-alkoxy, $C_1$-$C_4$-haloalkoxy, and oxo;

$R^{12}$ is H, $C_1$-$C_6$-alkoxy, $C_1$-$C_6$-haloalkoxy, S(O)$_m$—$C_1$-$C_4$-alkyl, S(O)$_m$—$C_1$-$C_4$-haloalkyl, Si($C_1$-$C_4$-alkyl)$_3$, $C_1$-$C_6$-alkyl, $C_3$-$C_6$-alkenyl, $C_3$-$C_6$-alkynyl, which are unsubstituted, or partially or fully halogenated and/or substituted with CN, $C_1$-$C_4$-alkoxy, $C_1$-$C_4$-haloalkoxy, S(O)$_m$—$C_1$-$C_4$-alkyl, S(O)$_m$—$C_1$-$C_4$-haloalkyl, $C_3$-$C_6$-cycloalkyl which is unsubstituted or substituted with 1 or 2 halogen and/or CN; and oxo;

$C_3$-$C_8$-cycloalkyl which is unsubstituted, or partially or fully halogenated and/or substituted with CN, $C_1$-$C_4$-alkyl, $C_1$-$C_4$-alkoxy, $C_1$-$C_4$-haloalkoxy, $C_1$-$C_4$-alkylthio, $C_3$-$C_4$-cycloalkyl, $C_3$-$C_4$-cycloalkyl-$C_1$-$C_4$-alkyl which rings optionally are substituted with 1 or 2 halogen and/or CN; and oxo;

phenyl, benzyl, pyridyl, phenoxy, which are unsubstituted, or partially or fully halogenated and/or substituted with halogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, and ($C_1$-$C_6$-alkoxy)carbonyl;

and a 3-, 4-, 5- or 6-membered saturated, partially or fully unsaturated heterocycle comprising 1, 2, or 3 heteroatoms selected from N, O, and S(O)$_m$ as ring members, where the heterocycle is optionally substituted with one or more $R^{14}$;

$R^{12a}$ and $R^{12b}$ have the meanings given for $R^{12}$; or $R^{12a}$ and $R^{12b}$, together with the nitrogen atom to which they are bound, form a 3-, 4-, 5-, 6- or 7-membered saturated, or partially unsaturated or maximally unsaturated heterocyclic ring, wherein the heterocyclic ring optionally can contain 1 or 2 heteroatoms or heteroatom groups selected from N, O, and $S(O)_m$ as ring members, which heterocycle is unsubstituted or substituted with one or more substituents halogen, $C_1$-$C_4$-alkyl, $C_1$-$C_4$-haloalkyl, $C_1$-$C_4$-alkoxy, $C_1$-$C_4$-haloalkoxy, and oxo; or $R^{12a}$ and $R^{12}$, together with the nitrogen atoms to which they are bound in the group $C(=NR^{12})N(R^{12a})R^{12b}$, form a 3-, 4-, 5-, 6- or 7-membered saturated, or partially unsaturated or maximally unsaturated heterocyclic ring, wherein the heterocyclic ring optionally can contain 1 or 2 heteroatoms or heteroatom groups selected from N, O, and $S(O)_m$ as ring members, which heterocycle is unsubstituted or substituted with one or more substituents halogen, $C_1$-$C_4$-alkyl, $C_1$-$C_4$-haloalkyl, $C_1$-$C_4$-alkoxy, $C_1$-$C_4$-haloalkoxy, and oxo;

$R^{13}$ is H, $Si(C_1$-$C_4$-alkyl$)_3$, $C_1$-$C_6$-alkyl, $C_2$-$C_6$-alkenyl, $C_2$-$C_6$-alkynyl, which are unsubstituted, or partially or fully halogenated and/or substituted with $C_3$-$C_4$-cycloalkyl, $C_1$-$C_4$-alkoxy, $C_1$-$C_4$-haloalkoxy, $S(O)_m$—$C_1$-$C_4$-alkyl, and oxo;

$C_3$-$C_8$-cycloalkyl which is unsubstituted, or partially or fully halogenated and/or substituted with $C_1$-$C_4$-alkyl, $C_3$-$C_4$-cycloalkyl, $C_1$-$C_4$-alkoxy, $C_1$-$C_4$-haloalkoxy, $S(O)_m$—$C_1$-$C_4$-alkyl, and oxo;

phenyl, benzyl, pyridyl and phenoxy, which are unsubstituted, or partially or fully halogenated and/or substituted with $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, and ($C_1$-$C_6$-alkoxy)carbonyl;

$R^{14}$ is halogen, $NO_2$, CN, OH, SH, $C_1$-$C_6$-alkoxy, $C_1$-$C_6$-haloalkoxy, $S(O)_m$—$C_1$-$C_4$-alkyl, $S(O)_mC_1$-$C_4$-haloalkyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C(=O)NR^{12a}R^{12b}$, $Si(C_1$-$C_4$-alkyl$)_3$;

$C_1$-$C_4$-alkyl, $C_2$-$C_6$-alkenyl, $C_2$-$C_6$-alkynyl, which are unsubstituted, or partially or fully halogenated and/or substituted with $C_3$-$C_4$-cycloalkyl, $C_1$-$C_4$-alkoxy, $C_1$-$C_4$-haloalkoxy, $S(O)_mC_1$-$C_4$-alkyl, and oxo;

$C_3$-$C_8$-cycloalkyl which is unsubstituted, or partially or fully halogenated and/or substituted with $C_1$-$C_4$-alkyl, $C_3$-$C_4$-cycloalkyl, $C_1$-$C_4$-alkoxy, $C_1$-$C_4$-haloalkoxy, $S(O)_m$—$C_1$-$C_4$-alkyl, and oxo;

phenyl, benzyl, pyridyl and phenoxy, which are unsubstituted, or partially or fully halogenated and/or substituted with $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, and ($C_1$-$C_6$-alkoxy)carbonyl; or two $R^{14}$ present together on the same atom of an unsaturated, or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl; or two $R^{14}$ on two adjacent carbon atoms form together with the carbon atoms they are bonded to a 4-, 5-, 6-, 7- or 8-membered saturated, partially unsaturated or maximally unsaturated ring, wherein the ring optionally can contain 1 or 2 heteroatoms or heteroatom groups selected from N, O, and $S(O)_m$ as ring members, and wherein the ring is optionally substituted with one or more groups $C_1$-$C_4$-alkyl, $C_1$-$C_4$-haloalkyl, $C_1$-$C_4$-alkoxy, and/or $C_1$-$C_4$-haloalkoxy;

and N-oxides, stereoisomers and agriculturally or veterinarily acceptable salts thereof.

2. The compound of formula I according to claim 1, wherein X is $NR^3$, O, or $S(O)_m$.

3. The compound of formula I according to claim 1, wherein U is O.

4. The compound of formula I according to claim 1, wherein Y is a direct bond.

5. The compound of formula I according to claim 1, wherein

W is phenyl, which is substituted with one to three groups selected from the group consisting of halogen, halomethyl, halomethoxy, and halomethyl-$S(O)_m$.

6. The compound of formula I according to claim 1, wherein

X is $NR^3$, and $R^3$ is H, alkoxy-carbonyl, $C_1$-$C_6$-alkyl, which alkyl is unsubstituted or substituted with CN, cycloalkyl or alkoxy.

7. The compound of formula I according to claim 1, wherein G is a group G1, G2, G3, or G4,

G1

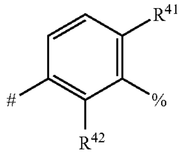

G2

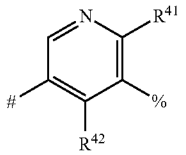

G3

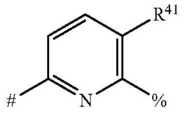

G4

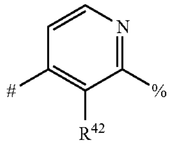

wherein # is the bond to X, % is the bond to Y, and $R^{41}$ and $R^{42}$ are H or a group $R^4$.

8. The compound of formula I according to claim 7, wherein G is G1 and $R^{42}$ is H.

9. The compound of formula I according to claim 1, wherein $R^5$, $R^6$ are independently from each other H, $C_1$-$C_6$-alkyl, $C_1$-$C_6$-haloalkyl, which are unsubstituted, or partially or fully substituted with $R^{51}$; or $N(R^{12a})R^{12b}$, $S(O)_mR^{13}$, $C(=O)OR^{13}$, $C(=U)N(R^{12a})R^{12b}$, $C_3$-$C_8$-cycloalkyl, $C_3$-$C_8$-halocycloalkyl, phenyl, or a 3-, 4-, 5-, 6- or 7-membered saturated, or partially or fully unsaturated heterocycle comprising 1, 2, 3, or 4 heteroatoms selected from N, O, and S(O)m as ring members, which rings are unsubstituted, or partially or fully substituted with $R^{52}$;

$R^{51}$ halogen, CN, $N(R^{12a})R^{12b}$, $C(=O)N(R^{12a})$, or $R^{12b}$;

$C_3$-$C_8$-cycloalkyl which is unsubstituted, partially or fully halogenated and/or partially or fully substituted with CN;

$S(O)_mR^{13}$, $C(=U)N(R^{12a})R^{12b}$;

phenyl or a 5-, 6-, or 7-membered saturated, partially or fully unsaturated heterocycle containing 1, 2, or 3 heteroatoms selected from N, O, $S(O)_m$ as ring members, wherein the rings are unsubstituted, or partially or fully substituted with $R^{14}$; or two $R^{51}$ present on the same carbon atom of an alkyl, alkenyl, alkynyl or cycloalkyl group may together be =O, =CH($C_1$-$C_4$-alkyl), =C($C_1$-$C_4$-alkyl)$_2$, =N($C_1$-$C_6$-alkyl), or =NO($C_1$-$C_6$-alkyl);

$R^{52}$ is a group as defined in $R^{51}$ or selected from $C_1$-$C_6$-alkyl, $C_2$-$C_6$-alkenyl, and $C_2$-$C_6$-alkynyl, which groups are unsubstituted, or partially or fully halogenated and/or substituted with one or two CN, $C_3$-$C_4$-cycloalkyl, $C_1$-$C_4$-alkoxy, $C_1$-$C_4$-haloalkoxy, or oxo.

10. The compound of formula I according to claim 1, which correspond to formula I.A

I.A

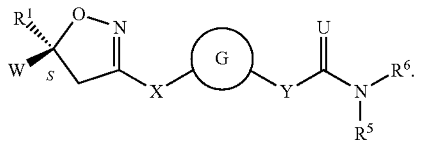

11. An agricultural or veterinary composition comprising at least one compound according to claim 1 and/or at least one agriculturally or veterinarily acceptable salt thereof, and at least one inert liquid and/or solid agriculturally or veterinarily acceptable carrier.

12. An agricultural composition for combating animal pests comprising at least one compound as defined in claim 1 and at least one inert liquid and/or solid acceptable carrier and, optionally, at least one surfactant.

13. A method for combating or controlling invertebrate pests, comprising contacting said pest or its food supply, habitat or breeding grounds with a pesticidally effective amount of at least one compound as defined in claim 1.

14. A method for protecting growing plants from attack or infestation by invertebrate pests, comprising contacting a plant, or soil or water in which the plant is growing, with a pesticidally effective amount of at least one compound as defined in claim 1.

15. A seed comprising a compound as defined in claim 1, or the enantiomers, diastereomers, or salts thereof, in an amount of from 0.1 g to 10 kg per 100 kg of seed.

16. A method for treating or protecting an animal from infestation or infection by invertebrate pests comprising bringing the animal into contact with a pesticidally effective amount of at least one compound of the formula I as defined in claim 1, a stereoisomer thereof, and/or at least one veterinarily acceptable salt thereof.

17. The compound of formula I according to claim 7 wherein $R^4$ is H, halogen, halomethyl, or halomethoxy.

* * * * *